US010017549B2

(12) United States Patent
Baum et al.

(10) Patent No.: US 10,017,549 B2
(45) **Date of Patent: *Jul. 10, 2018**

(54) **HEMIPTERAN AND COLEOPTERAN ACTIVE TOXIN PROTEINS FROM *BACILLUS THURINGIENSIS***

(71) Applicant: Monsanto Technology LLC, St. Louis, MO (US)

(72) Inventors: James A. Baum, Webster Groves, MO (US); Stanislaw Flasinski, Chesterfield, MO (US); Gregory R. Heck, Crystal Lake Park, MO (US); Stephen R. Penn, Chesterfield, MO (US); Uma Rao Sukuru, St. Charles, MO (US); Xiaohong Shi, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1239 days.

This patent is subject to a terminal disclaimer.

(21) Appl. No.: 13/950,439

(22) Filed: Jul. 25, 2013

(65) Prior Publication Data

US 2013/0305416 A1 Nov. 14, 2013

Related U.S. Application Data

(62) Division of application No. 12/549,512, filed on Aug. 28, 2009, now Pat. No. 8,513,493.

(60) Provisional application No. 61/093,084, filed on Aug. 29, 2008.

(51) Int. Cl.

| | |
|---|---|
| *C07K 14/325* | (2006.01) |
| *A01N 63/00* | (2006.01) |
| *C12N 15/82* | (2006.01) |

(52) U.S. Cl.
CPC ............ *C07K 14/325* (2013.01); *A01N 63/00* (2013.01); *C12N 15/8286* (2013.01); *Y02A 40/162* (2018.01)

(58) Field of Classification Search
None
See application file for complete search history.

(56) References Cited

U.S. PATENT DOCUMENTS

| | | | |
|---|---|---|---|
| 5,723,440 A | 3/1998 | Stockhoff et al. | |
| 5,885,963 A | 3/1999 | Stockhoff et al. | |
| 5,942,658 A | 8/1999 | Donovan et al. | |
| 8,513,493 B2 * | 8/2013 | Baum .................... | A01N 63/00 435/252.3 |
| 2006/0021087 A1 | 1/2006 | Baum et al. | |
| 2006/0191034 A1 | 8/2006 | Baum et al. | |
| 2006/0242732 A1 | 10/2006 | Carozzi et al. | |
| 2008/0295207 A1 | 11/2008 | Baum et al. | |
| 2010/0064394 A1 | 3/2010 | Baum et al. | |

FOREIGN PATENT DOCUMENTS

| | | | |
|---|---|---|---|
| WO | 9314205 | A1 | 7/1993 |
| WO | 9639843 | A1 | 12/1996 |
| WO | 9717600 | A2 | 5/1997 |
| WO | 0171042 | A2 | 9/2001 |
| WO | 2005/110068 | A2 | 11/2005 |
| WO | 2006/107761 | A2 | 10/2006 |
| WO | 2007/027776 | A2 | 3/2007 |
| WO | 2008/134072 | A2 | 11/2008 |
| WO | 2010/025320 | A1 | 3/2010 |

OTHER PUBLICATIONS

Argolo-Filho et al 2014, Insects 5: 62-91.*
Huang et al 2007, Journal of Invertebrate Pathology 95: 175-180.*
Baum et al., "Binary Toxins from Bacillus thuringiensis Active against the Western Corn Rootworm, Diabrotica virgifera virgifera LeConte", Applied and Environmental Microbiology, Aug. 2004, pp. 889-4898, vol. 70 No. 8.
Brown et al., "Molecular Characterization of Two Novel Crystal Protein Genes from *Bacillus thuringiensis* subsp. *thompsoni*", Journal of Bacteriology, Jan. 1992, pp. 549-557, vol. 174 No. 2.
Chan et al., "Unusual Amino Acid Determinants of Host Range in the Mtx2 Family of Mosquitocidal Toxins", The Journal of Biological Chemistry, Jun. 14, 1996, pp. 14183-14187, vol. 271 No. 24.
Crickmore et al., "Revision of the Nomenclature for the Bacillus thuringiensis Pesticidal Crystal Proteins", Microbiology and Molecular Biology Review, Sep. 1998, pp. 807-813, vol. 62, No. 3.
EBI Accession No. GSP: ABB68459, "*Drosophila melanogaster* Polypeptide SEQ ID No. 32169. DYDERPSKRP RGKPTAGGTAG RKISPRKPGR VEERRSNFNED RPLGRRRSEK ERTTPSSALD", Mar. 2002, Database Geneseq.
EMBL; Accession DQ836184, Bacillus thuringiensis strain F14-1 Cry51Aa1 (cry51Aa1)gene complete CDs, srs.ebi.ac.uk/srsbin/cgi-bin/wgetz?-e+[EMBL:DQ836184]-1—newId, created Aug. 1, 2007, 2 pp.
EMBL; XP002558781 retrieved from Accession BX560037, "*Glossina morsitans morsitans* (Tseatse fly) EST from Adult Infected Midgut Library, Clone Tse47e08_p1c", created Jul. 15, 2003.
EMBL; XP002558782 retrieved from Accession BX553088, "*Glossina morsitans morsitans* (Tseatse fly) EST from Adult Infected Midgut Library, Clone Tse127c03_p1c", created Jul. 16, 2003.
EMBL; XP002558783 retrieved from Accession BX551977, "*Glossina morsitans morsitans* (Tseatse fly) EST from Adult Infected Midgut Library, Clone Tse120h04_p1c", created Jul. 16, 2003.
EMBL; XP002558784 retrieved from Accession BX556938, "*Glossina morsitans morsitans* (Tseatse fly) EST from Adult Infected Midgut Library, Clone Tse2d02_p1c", created Jul. 16, 2003.

(Continued)

*Primary Examiner* — David H Kruse
(74) *Attorney, Agent, or Firm* — Timothy K. Ball; Carine M. Doyle; Arnold & Porter Kaye Scholer LLP

(57) ABSTRACT

A novel *Bacillus thuringiensis* crystal protein exhibiting insect inhibitory activity is disclosed. Growth of *Lygus* insects is significantly inhibited by providing the novel crystal protein in *Lygus* insect diet. Polynucleotides encoding the crystal protein, transgenic plants and microorganisms that contain the polynucleotides, isolated peptides derived from the crystal protein, and antibodies directed against the crystal protein are also provided. Methods of using the crystal protein and polynucleotides encoding the crystal protein to control Hemipteran insects are also disclosed.

15 Claims, No Drawings

(56) References Cited

OTHER PUBLICATIONS

EMBL; XP002558785 retrieved from Accession FC540005, "AlAl-aad47a09.g1 Anclostoma_caninum_EST_L3_Activated Ancylostoma caninum cDNA, mRNA Sequence", created Dec. 13, 2007.

EMBL; XP002558786 retrieved from Accession FC553861, "AlAl-aad15a09.g1 Anclostoma_caninum_EST_L3_Activated Ancylostoma caninum cDNA, mRNA Sequence", created Dec. 13, 2007.

EMBL; XP002558787 retrieved from Accession FF6822172, "HTAL-aad03d03.g1 Heterorhabditis_Bacteriophora_EST_L4+bagge dworms_pSMART Heterorhabditis Bacteriophora cDNA, mRNA Sequence", created Apr. 20, 2008.

Hofte et al., "Insecticidal Crystal Proteins of Bacillus thuringiensis", Microbiological Reviews, Jun. 1989, pp. 242-255, vol. 53, No. 2, American Society for Microbiology.

Huang et al., "Microbial Control and Biotechnology Research on Bacillus Thuringiensis in China"; Journal of Invertebrate Pathology; Mar. 31, 2007, pp. 175-180, vol. 95, No. 3.

International Search Report and Written Opinion dated Nov. 24, 2008 for PCT/US2008/005542 filed Apr. 25, 2008.

International Search Report and Written Opinion for PCT/US2009/055293 dated Dec. 18, 2009.

Lehane et al., "Adult Midgut Expressed Gene Sequence Tags from the Tsetse Fly Glossina Morsitans and Expression Analysis of Putative Immune Response Genes", Genome Biology, Sep. 2003, p. R63, vol. 4, No. 10, BioMed Central Ltd., London.

Liu et al., "New Gene from Nine Bacillus sphaericus Strains Encoding Highly Conserved 35.8-Kilodalton Mosquitocidal Toxins", Applied and Environmental Microbiology, Jun. 1996, pp. 2174-2176, vol. 62 No. 6.

New England Biolabs, Random Primer 12, Jun. 2004, web.archive.org/web/20040618195247/http:neb.com/nebcomm/products/productS1256.asp, 1 pg.

New England Biolabs, Random Primer 12, Jun. 2004, web.archive.org/web/20040619083054/http:neb.com/nebcomm/products/productS1255.asp, 1 pg.

Thanabalu et al., "A Bacillus Sphaericus Gene Encoding a Novel Type of Mosquitocidal Toxin of 31.8 kDa, Gene", 1996, pp. 85-89, vol. 170 No. 1.

Wellman-Desbiens et al., "Development of a Bacillus thuringiensis-Based Assay on Lygus Hesperus", Journal of Economic Entomology, Oct. 2005, pp. 1469-1479, vol. 98 No. 5.

Chen et al., "Site-Directed Mutations in a Highly Conserved Region of Bacillus thuringiensis delta-endotoxin Affect Inhibition of Short Circuit Current Across Bombyx mori Midguts", Proceeding of the National Academy of Sciences, Oct. 1993, pp. 9041-9045, vol. 90.

Schurter et al., "Efficient Transformation of Bacillus thuringiensis and B. cereus via Electroporation: Transformation of Acrystalliferous Strains with a Cloned delta-Endotoxin Gene", Journal of Molecular and General Genetics, 1989, pp. 177-181, vol. 218.

Guo et al., "Protein Tolerance to Random Amino Acid Change", Proceeding of the National Academy of Sciences, Jun. 2004, pp. 9205-9210, vol. 101, No. 25.

* cited by examiner

HEMIPTERAN AND COLEOPTERAN ACTIVE TOXIN PROTEINS FROM *BACILLUS THURINGIENSIS*

CROSS-REFERENCE TO RELATED APPLICATIONS

This patent application is a divisional of co-pending U.S. patent application Ser. No. 12/549,512, filed Aug. 28, 2009, which claims the benefit of U.S. Provisional Patent Application No. 61/093,084, filed Aug. 29, 2008, each of which is incorporated herein by reference in its entirety.

STATEMENT REGARDING FEDERALLY SPONSORED RESEARCH OR DEVELOPMENT

Not Applicable.

APPENDIX

Not Applicable.

INCORPORATION OF SEQUENCE LISTING

A computer readable form of the sequence listing is provided herein, containing the file named "38-21(55961) B_ST25.txt", which is 108563 bytes in size (measured in MS-DOS), and is incorporated herein by reference in its entirety. This Sequence Listing consists of SEQ ID NOs:1-55.

BACKGROUND OF THE INVENTION

Field of the Invention

This invention relates generally to the field of insect inhibitory *Bacillus thuringiensis* proteins and, more particularly, to *B. thuringiensis* crystal proteins that inhibit Hemipteran and Coleopteran insects. Isolated polynucleotides and proteins, transgenic cells, parts, and plants and related methods that provide for inhibition of Hemipteran and Coleopteran insects are described. Also described are methods for combining the *B. thuringiensis* crystal proteins that inhibit Hemipteran and Coleopteran insects with distinct insect control agents to obtain increased levels of Hemipteran and Coleopteran insect inhibition, Hemipteran and Coleopteran insect resistance management, or an expanded spectrum of insect pest control.

Related Art

*Bacillus thuringiensis* Crystal Proteins

The Gram-positive soil bacterium *Bacillus thuringiensis* is well known for its production of proteinaceous parasporal crystals, or δ-endotoxins, that are toxic to a variety of Lepidopteran, Coleopteran, and Dipteran larvae. *B. thuringiensis* produces crystal proteins during sporulation which are specifically toxic to certain species of insects. Many different strains of *B. thuringiensis* have been shown to produce insecticidal crystal proteins, and compositions comprising *B. thuringiensis* strains which produce proteins having insecticidal activity have been used commercially as environmentally-acceptable insecticides because of their toxicity to the specific target insect, and non-toxicity to plants and other non-targeted organisms.

Commercial formulations of naturally occurring *B. thuringiensis* isolates have long been used for the biological control of agricultural insect pests. In commercial production, the spores and crystals obtained from the fermentation process are concentrated and formulated for topical foliar application according to conventional agricultural practices.

Several first toxins have been used commercially in plants. Unfortunately, the toxins that are currently available do not provide for control of all insect pests that continue to plague crop production. In particular, Hemipteran insects still must be controlled by use of chemical, (topically applied or soil applied) insecticides. The Hemipteran or "piercing/sucking" insects are especially damaging to plants in that they are also known to transmit damaging plant viruses and cause plants to be more susceptible to bacterial and fungal infection. There is thus a need for additional materials and methods that would permit inhibition of Hemipteran insect pests in crops. There is also a need to obtain several different types of Hemipteran insect control agents with distinct modes of action for use in transgenic plants as Hemipteran insect resistance management tools.

Additionally, there remains a need for compositions and methods useful in producing transgenic plants which express two or more different *B. thuringiensis* toxins toxic to the same insect species and which confer a level of resistance management for delaying the onset of resistance of any particular susceptible insect species to one or more of the insecticidal agents expressed within the transgenic plant. Alternatively, expression of a *B. thuringiensis* insecticidal protein toxic to a particular target insect pest along with a different agent toxic to the same insect pest but which confers toxicity by a different mode of action from that exhibited by the *B. thuringiensis* toxin is desirable. Such other different agents comprise *Xenorhabdus* sp. or *Photorhabdus* sp. insecticidal proteins, deallergenized and deglycosylated patatin proteins or permuteins thereof, *B. thuringiensis* vegetative insecticidal proteins, lectins, approaches such as dsRNA-mediated gene suppression, and the like. One method for achieving this result would be to produce two different transgenic events, each event expressing a different insecticidal agent, and breeding the two traits together into a hybrid plant. Another method for achieving this result would be to produce a single transgenic event expressing both insecticidal agents. This can be accomplished by transformation with a nucleotide sequence that encodes two or more insecticidal agents, but another method would be to produce a single event that was transformed to express a first insecticidal agent, and then transform that event to produce a progeny event that expresses both the first and the second insecticidal agents.

SUMMARY OF THE INVENTION

It is in view of the above problems that the present invention was developed.

The invention first relates to an isolated polynucleotide which encodes a protein comprising a polypeptide sequence exhibiting at least 88% sequence identity to the amino acid sequence as set forth in SEQ ID NO:6 over a length of at least 300 amino acids. In other embodiments, an isolated polynucleotide which encodes a TIC853 insect inhibitory protein or an insect inhibitory protein fragment derived therefrom, wherein the insect inhibitory protein or protein fragment comprises a polypeptide sequence that has at least about 88% sequence identity over a length of at least 300 amino acids of a corresponding polypeptide sequence contained within SEQ ID NO:6 is provided. In certain embodiments, the isolated polynucleotide encodes a TIC853 protein of at least 300 amino acids that has at least 95% sequence identity over a length of at least 300 amino acids of a corresponding polypeptide sequence contained within SEQ ID NO:6 and displays insect inhibitory activity. In other embodiments, the isolated polynucleotide encodes a TIC853 protein of at least 306 amino acids that have at least 88% sequence identity over a length of at least 306 amino acids of a corresponding polypeptide sequence contained within SEQ ID NO:6 and displays insect inhibitory activity. In still other embodiments, the isolated polynucleotide encodes a TIC853 protein of 306 amino acids that have at least 95% or at least 99% sequence identity over a length of 306 amino acids of a corresponding polypeptide sequence of SEQ ID NO:6 and display insect inhibitory activity. The polynucleotide sequences of the invention can also encode insect inhibitory polypeptide sequences with at least about 90%, 95%, 98%, 99%, or 100% sequence identity to the corresponding polypeptide sequence of at least 302, at least 304, or at least 305 amino acids contained within SEQ ID NO:6. In certain embodiments, the polynucleotide encodes the polypeptide sequence of SEQ ID NO:6. In still other embodiments, the polynucleotide encodes TIC852 (SEQ ID NO:2). In still other embodiments, the isolated polynucleotide encodes a polypeptide that has less than 88% sequence identity over a length of at least 300 amino acids of a corresponding polypeptide contained within SEQ ID NO:11 or SEQ ID NO:15. In certain embodiments, the polynucleotide sequence has been optimized for expression in plants. In certain embodiments, the polynucleotide can be selected from the group consisting of SEQ ID NO:1, SEQ ID NO:5, SEQ ID NO:7, SEQ ID NO:16, SEQ ID NO:17, SEQ ID NO:18, and SEQ ID NO:19.

Isolated polynucleotides of the invention can encode a TIC853 insect inhibitory protein or insect inhibitory protein fragment derived therefrom that inhibits a Hemipteran insect, a Heteropteran insect, Coleopteran insect or a Homopteran insect. The Hemipteran insect can be a *Lygus* insect and the Homopteran insect can be an aphid, a hopper, or a whitefly. The encoded TIC853 insect inhibitory protein or insect inhibitory protein fragment derived therefrom inhibits *Lygus* at a *Lygus* diet concentration of at least about 5 ppm, 50 ppm, 250 ppm, or 500 ppm (parts per million) of the TIC853 protein or protein fragment in the *Lygus* diet. The TIC853 insect inhibitory protein fragment encoded by the polynucleotide comprises a peptide sequence of at least 300 amino acid residues. This isolated polynucleotide encoding the TIC853 protein can be modified for improved expression in plants compared to the native coding sequence. Embodiments of a TIC853 encoding polynucleotide that are designed for expression in plants are provided as SEQ ID NOs:16, 17, 18 and 19. In other embodiments, the polynucleotide designed for expression in plants encodes a TIC853 protein with an N-terminal chloroplast or plastid targeting peptide. Embodiments comprising plastid targeted TIC853 proteins are provided in SEQ ID NOs: 20, 21, 22, 23 and 24, each of which comprises a polynucleotide designed for expression of the TIC853 insect inhibitory protein in plants that is also linked in frame to a nucleotide sequence encoding a plastid targeting peptide. The plastid targeting peptide is operably linked to TIC853 upon expression and functions to direct the insertion of the TIC853 insect inhibitory protein into the plant plastid.

Other isolated polynucleotides of the invention include polynucleotides that hybridize under high stringency conditions with either the native *Bacillus thuringiensis* TIC853 gene (SEQ ID NO:5) or with any of the genes designed for improved plant expression of TIC853, which has an enriched G+C content (SEQ ID NOs:16, 17, 18 and 19) compared to the native coding sequence set forth at SEQ ID NO:5. Polynucleotides that hybridize under stringent conditions can be selected from the group consisting of SEQ ID NO:5, SEQ ID NO:16, SEQ ID NO:17, SEQ ID NO:18, and SEQ ID NO:19.

The invention further provides for transgenic plants or plant parts derived therefrom comprising a TIC853 insect inhibitory protein or an insect inhibitory protein fragment derived therefrom, wherein the TIC853 insect inhibitory protein or protein fragment comprises a polypeptide sequence that has at least about 88% sequence identity over a length of at least 300 amino acids to a corresponding polypeptide sequence contained within SEQ ID NO:6. The transgenic plant or plant part comprises the TIC853 protein or protein fragment at a concentration from at least about 5 µg to about 250 µg of the TIC853 protein or protein fragment per gram fresh weight plant tissue, or any amount in between. The TIC853 insect inhibitory protein fragment encoded by the polynucleotide comprises a peptide sequence of at least 300 amino acid residues. The transgenic plant part can be selected from a leaf, a stem, a flower, a sepal, a fruit, a root, or a seed.

The invention also provides for transformed host cells comprising a polynucleotide which encodes a TIC853 insect inhibitory protein or an insect inhibitory protein fragment derived therefrom, wherein the insect inhibitory protein or protein fragment comprises a polypeptide sequence that has at least about 88% sequence identity over a length of at least 300 amino acids of a corresponding polypeptide sequence contained within SEQ ID NO:6. The TIC853 insect inhibitory protein fragment encoded by the polynucleotide comprises a peptide sequence of at least 300 amino acid residues. The transformed host cell can be a microorganism selected from the group consisting of a bacterial cell, a yeast cell, and a plant cell. Transformed plant cells of the invention can be selected from the group consisting of barley, corn, oat, rice, rye, sorghum, turf grass, sugarcane, wheat, alfalfa, banana, broccoli, bean, cabbage, canola, carrot, cassava, cauliflower, celery, citrus, cotton, a cucurbit, eucalyptus, flax, garlic, grape, onion, lettuce, pea, peanut, pepper, potato, poplar, pine, sunflower, safflower, soybean, strawberry, sugar beet, sweet potato, tobacco, tomato, ornamental, shrub, nut, chickpea, pigeonpea, millets, hops, and pasture grass plant cells. In certain embodiments, the transformed plant cell is a cotton plant cell. Plants derived from the transformed plant host cells, seeds produced from the plants derived from the transformed host cell, and progeny plants from that seed are also contemplated by the invention. Transformed bacterial host cells of the invention can be selected from the group consisting of an *Agrobacterium*, a *Bacillus*, an *Escherichia*, a *Salmonella*, a *Pseudomonas*, and a *Rhizobium* bacterial cell. In certain embodiments, the transformed bacterial cell is a *Bacillus thuringiensis* cell. Another embodiment of the invention relates to a biologically-pure or isolated culture of an *Escherichia coli* strain K12 harboring vector pMON102351, deposited on Mar. 28, 2008 with the Agricultural Research Culture Collection, Northern Regional Research Laboratory (NRRL), Peoria, Ill., USA, and having Accession No. NRRL B-50129. Another embodiment of the invention relates to a biologically-pure or isolated culture of an *Escherichia coli* strain K12 harboring vector pMON102352, deposited on Mar. 28, 2008 with the Agricultural Research Culture Collection, Northern Regional Research Laboratory (NRRL), Peoria, Ill., USA, and having Accession No. NRRL B-50130.

The invention further provides methods for controlling *Lygus* comprising the steps of: (a) providing a *Lygus* inhibitory amount of a TIC853 insect inhibitory protein or an insect inhibitory protein fragment derived therefrom, wherein the insect inhibitory protein or protein fragment comprises a polypeptide sequence that has at least about 88% sequence identity over a length of at least 300 amino acids of a corresponding polypeptide sequence contained within SEQ ID NO:6; and (b) contacting the *Lygus* with the inhibitory amount of the polypeptide sequence, thereby controlling a *Lygus* insect. The polypeptide sequence used in this method can also have at least about 90%, 95%, 98%, 99%, or 100% sequence identity to the corresponding polypeptide sequence contained within SEQ ID NO:6. The TIC853 insect inhibitory protein fragment encoded by the polynucleotide comprises a peptide sequence of at least 300 amino acid residues. In one embodiment of this method, the *Lygus* inhibitory amount of the polypeptide sequence can be provided in a *Lygus* diet in step (a) and the *Lygus* can be contacted in step (b) by permitting the *Lygus* to feed on the diet. In a more particular embodiment of the method, the *Lygus* diet is a transgenic plant. When the *Lygus* diet of this method is a transgenic plant, the *Lygus* inhibitory amount of the polypeptide sequence is from at least about 5 μg to about 250 μg per gram fresh weight tissue of the transgenic plant. In other embodiments of this method, the *Lygus* inhibitory amount of the polypeptide sequence is provided in step (a) by spraying a composition comprising the polypeptide on a plant. The composition used in this embodiment of the method comprises bacterial cells or bacterial spores that express the polypeptide. In particular embodiments of the method, the bacterial cells or bacterial spores are *Bacillus* cells or *Bacillus* spores. The composition used in this method can also comprise parasporal crystals containing the polypeptide. In any of these methods of controlling *Lygus*, the plant can be infested with *Lygus*.

The invention also provides for isolated oligonucleotides comprising at least 12 contiguous nucleotides of a sequence contained within SEQ ID NO:5 or contained within the complement of SEQ ID NO:5 that are not identical to any 12 contiguous nucleotides of SEQ ID NO:10 or SEQ ID NO:14 or to any 12 contiguous nucleotides of the complements of SEQ ID NO:10 or SEQ ID NO:14. Such isolated oligonucleotides are useful for detecting either SEQ ID NO:5 or related polynucleotides that encode insect inhibitory proteins related to TIC853. Isolated oligonucleotides comprising at least 12 contiguous nucleotides of a sequence contained within SEQ ID NOs:16, 17, 18, or 19 or contained within the complement of SEQ ID NOs:16, 17, 18, or 19 that are not identical to any 12 contiguous nucleotides of SEQ ID NO:54 or to any 12 contiguous nucleotides of the complements of SEQ ID NO:54 are also provided by the invention. These isolated oligonucleotides are useful for detecting either (i) SEQ ID NOs:16, 17, 18, or 19, (ii) a polynucleotide designed for use in plants encoding a TIC853 protein, or (iii) related polynucleotides that encode TIC853 proteins. Kits for detection of a polynucleotide sequence in a sample that comprise an oligonucleotide that specifically hybridizes to a polynucleotide sequence of SEQ ID NOs:16, 17, 18, or 19 or a complement thereof and a control polynucleotide that hybridizes to the oligonucleotide are also provided by this invention. In the context of these kits, an oligonucleotide is said to specifically hybridize to SEQ ID NOs:16, 17, 18, or 19 when the oligonucleotide would form an imperfect hybrid containing at least one mismatched base pair with SEQ ID NO:54 or the complement of SEQ ID NO:54. These oligos can also be used to shuffle a sequence encoding a portion of a TIC853 protein, make redundant oligos encoding eight base amino acid sequences, and identify iterative improvements to the existing protein.

Other embodiments of the invention include compositions comprising at least two degenerate oligonucleotide primers of at least 12 nucleotides, wherein nucleotide sequences of the degenerate oligonucleotide primers are derived from the polypeptide sequence of SEQ ID NO:6 and wherein the degenerate oligonucleotide primers would not hybridize under stringent conditions to SEQ ID NO:10 or SEQ ID NO:14 or to any 12 contiguous nucleotides of the complements of SEQ ID NO:10 or SEQ ID NO:14. These oligonucleotide primer compositions are useful for detecting polynucleotide sequences in either plant or bacterial samples that encode TIC853 proteins.

The invention further provides methods for detecting or isolating a polynucleotide that encodes a TIC853 protein or a TIC853 related protein in a sample that comprise the steps of: (a) selecting a pair of degenerate oligonucleotide primers capable of producing an amplicon, wherein nucleotide sequences of the degenerate oligonucleotide primers are derived from a TIC853 polypeptide sequence of SEQ ID NO:6 and wherein the degenerate oligonucleotide primers would not hybridize under stringent conditions to SEQ ID NO:10 or SEQ ID NO:14 or to any 12 contiguous nucleotides of the complements of SEQ ID NO:10 or SEQ ID NO:14; (b) producing an amplicon from the polynucleotide sequence in the sample; and (c) detecting or isolating the amplicon, thereby detecting or isolating a polynucleotide that encodes a TIC853 protein or a TIC853 related protein in a sample. In this method the detected or isolated amplicon can encode a polypeptide that has at least 45%, 70%, or 90% sequence identity to TIC853 (SEQ ID NO:6). Other methods for detecting or isolating a polynucleotide that encodes a TIC853 protein in a sample provided herein comprise the steps of: (a) selecting a degenerate oligonucleotide or collection of degenerate oligonucleotides, wherein nucleotide sequences of the degenerate oligonucleotide primers are derived from a TIC853 polypeptide sequence of SEQ ID NO:6; (b) hybridizing the degenerate oligonucleotide or collection of degenerate oligonucleotides to the sample; (c) detecting hybridization in the sample to a polynucleotide, thereby detecting polynucleotide that encodes a TIC853 protein in a sample, and (d) isolating the polynucleotide detected by hybridization in step (c). In this method, the detected polynucleotide can encode a polypeptide that has at least 45%, 70%, or 90% sequence identity to TIC853 (SEQ ID NO:6).

The invention also provides methods for expressing an insect inhibitory TIC853 protein in a plant that comprise the steps of: (a) inserting into a plant cell genome a nucleic acid sequence comprising in the 5' to 3' direction a recombinant, double-stranded DNA molecule, wherein the recombinant, double-stranded DNA molecule comprises: (i) a promoter that functions in the plant cell; (ii) a polynucleotide sequence encoding a polypeptide comprising a TIC853 insect inhibitory protein or an insect inhibitory protein fragment derived therefrom, wherein the insect inhibitory protein or protein fragment comprises a polypeptide sequence that has at least about 88% sequence identity over a length of at least 300 amino acids of a corresponding polypeptide sequence contained within SEQ ID NO:6; and (iii) a 3' non-translated nucleotide sequence that functions in the cells of the plant to cause polyadenylation, wherein said promoter, said polynucleotide sequence, and said 3' non-translated nucleotide sequence are operably linked (b) obtaining a transformed plant cell containing the nucleic acid sequence of step (a); and (c) regenerating from the transformed plant cell a transformed plant that expresses the TIC853 protein. In this method, the polynucleotide sequence of step (a) can encode either a TIC853 protein that has at least 88%, 90%, 95% or 99% sequence identity to SEQ ID NO:6 or can encode the TIC853 protein of SEQ ID NO:6. This polynucleotide sequence can be SEQ ID NOs:16, 17, 18, or 19 or another plant optimized sequence that encodes a TIC853 protein. The TIC853 insect inhibitory protein fragment encoded by the polynucleotide can comprise a peptide sequence of at least 300 amino acid residues. In other embodiments of this method, the polynucleotide sequence of step (a) that encodes a TIC853 protein is operably linked to a polynucleotide sequence that encodes a plastid targeting polypeptide. The polynucleotides of SEQ ID NOs:20, 21, 22, and 23 encode a TIC853 protein that is operably linked to the plastid targeting polypeptide that can be used in certain embodiments of this method.

The invention further provides recombinant DNA vectors comprising in the 5' to 3' direction: (i) a promoter that functions in the plant cell; (ii) a polynucleotide sequence encoding a polypeptide comprising a TIC853 insect inhibitory protein or an insect inhibitory protein fragment derived therefrom, wherein said insect inhibitory protein or protein fragment comprises a polypeptide sequence that has at least about 88% sequence identity over a length of at least 300 amino acids to a corresponding polypeptide sequence contained within SEQ ID NO:6; and (iii) a 3' non-translated nucleotide sequence that functions in the cells of the plant to cause polyadenylation, where the promoter, said polynucleotide sequence, and said 3' non-translated nucleotide sequence are operably linked. In these vectors, the polynucleotide sequence can also encode either a TIC853 protein that has at least 90%, 95%, 98% or 99% sequence identity over a length of at least 300 amino acids of SEQ ID NO:6 or can encode the TIC853 protein of SEQ ID NO:6. The TIC853 insect inhibitory protein fragment encoded by the polynucleotide comprises a peptide sequence of at least 300 amino acid residues. The polynucleotide sequence encoding the TIC853 protein is preferably a sequence that is optimized for expression in plants, such as the sequence of SEQ ID NOs:16, 17, 18, or 19. In other embodiments, the polynucleotide sequence that encodes a TIC853 protein is operably linked to a polynucleotide sequence that encodes a plastid targeting polypeptide. A vector of the invention can comprise a polynucleotide sequence of any of SEQ ID NOs:20, 21, 22, or 23 that encode a polypeptide comprising a plastid targeting peptide that is operably linked to a TIC853 protein. Vectors of the invention can further comprise a polynucleotide that encodes a selectable marker gene. A selectable marker gene that confers resistance to AMPA, atrazine, bromoxynil, dalapon, dicamba, glyphosate, hygromycin, methotrexate, neomycin, phosphinotricin, a sulfonylurea or 2,4-D or combinations thereof can be used in the vectors of the invention.

Also provided by this invention are commodity products produced from a plant or seed wherein the commodity product contains a detectable amount of a TIC853 protein or a polynucleotide that encodes a TIC853 protein. This commodity product can be derived from a cotton plant or cotton plant seed, or similarly from corn, rice, wheat, soy, chickpea, pigeonpea, sugarcane, sugarbeet, and the like. For example, when the commodity product is derived from a cotton plant or cotton plant seed, the commodity product can be lint, oil, meal, or hulls.

In certain embodiments, the commodity product comprises a processed product of at least one plant part and the commodity product contains a detectable amount of a TIC853 protein that has at least about 88% sequence identity over a length of at least 300 amino acids of a corresponding polypeptide sequence contained within SEQ ID NO:6. This commodity product can be obtained from a cotton, corn, rice, wheat, soy, chickpea, pigeonpea, sugarcane, or sugarbeet plant part. In certain embodiments where this commodity product is obtained from a cotton plant or a cotton seed, the commodity product can comprise lint, oil, meal, or hulls.

In certain embodiments, the commodity product comprises a processed product of at least one plant part and the commodity product contains a detectable amount of a polynucleotide that encodes a polypeptide sequence exhibiting at least 88% sequence identity to the amino acid sequence as set forth in SEQ ID NO:6 over a length of at least 300 amino acids. This commodity product can be obtained from a cotton, corn, rice, wheat, soy, chickpea, pigeonpea, sugarcane, or sugarbeet plant part. In certain embodiments where this commodity product is obtained from a cotton plant or a cotton seed, the commodity product can comprise lint, oil, meal, or hulls.

In certain embodiments, the commodity product comprises a processed product of at least one plant part and the commodity product contains a detectable amount of a polynucleotide comprising any of: i) at least 12 contiguous nucleotides of a sequence contained within SEQ ID NO:5 or contained within the complement of SEQ ID NO:5, wherein said polynucleotide is not identical to any 12 contiguous nucleotides of SEQ ID NO:10 or SEQ ID NO:14 or to any 12 contiguous nucleotides of the complements of SEQ ID NO:10 or SEQ ID NO:14; or, ii) at least 12 contiguous nucleotides of a sequence contained within SEQ ID NOs:16, 17, 18, or 19 or contained within the complement of SEQ ID NOs:16, 17, 18, or 19, wherein said polynucleotide is not identical to any 12 contiguous nucleotides of SEQ ID NO:54 or to any 12 contiguous nucleotides of the complement of SEQ ID NO:54. This commodity product can be obtained from a cotton, corn, rice, wheat, soy, chickpea, pigeonpea, sugarcane, or sugarbeet plant part. In certain embodiments where this commodity product is obtained from a cotton plant or a cotton seed, the commodity product can comprise lint, oil, meal, or hulls.

The invention also provides a method for controlling at least one insect pest comprising the steps of: (a) providing at least two different insect pest inhibitory agents in a composition, the composition comprising (i) an insect inhibitory amount of a TIC853 protein, where the insect inhibitory TIC853 protein comprises a polypeptide sequence has at least 88% sequence identity over a length of at least 300 amino acids of a corresponding polypeptide sequence contained within SEQ ID NO:6, and an insect inhibitory amount of (ii) at least one ribonucleotide sequence that functions upon ingestion by the insect pest to inhibit a biological function within the insect pest and/or (iii) an insect inhibitory amount of at least one insect inhibitory protein other than a TIC853 protein; and (b) contacting the insect pest or pests with an inhibitory amount of the composition. In this method, the insect pest controlled can be a Hemipteran insect, a Heteropteran insect or a Homopteran insect. One Hemipteran insect controlled by the method is a *Lygus* insect. A Homopteran insect controlled by the method is an aphid, a hopper or a whitefly. In this method, a TIC853 insect inhibitory protein comprises a polypeptide sequence that has at least about 88% sequence identity over a length of at least 300 amino acids of a corresponding polypeptide sequence contained within SEQ ID NO:6. A TIC853 protein used in the method can also comprise a TIC853 insect inhibitory protein fragment of at least 300 amino acid residues in length. When a biological function is inhibited by a ribonucleotide, the biological function within the insect pest in (ii) can be an essential biological function. The essential biological function inhibited by the method can be provided by an essential protein or ribonucleic acid of the insect pest, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis. The essential biological function can be inhibited in *Lygus* by a ribonucleotide sequence that comprises from about 50 to about 5000 contiguous nucleotides exhibiting from about 80 to about 100% sequence identity to a nucleotide coding sequence selected from the group consisting of SEQ ID NO:28 through SEQ ID NO:43. In other embodiments of this method, the one insect inhibitory protein other than a TIC853 protein can be derived from *Bacillus thuringiensis*. This insect inhibitory protein other than a TIC853 protein can be selected from the group consisting of AXMI-027, AXMI-036, AXMI-038, AXMI-018, AXMI-020, AXMI-021, AXMI-010, AXMI-003, AXMI-008, AXMI-006, AXMI-007, AXMI-009, AXMI-014, ET29, ET37, AXMI-004, AXMI-028, AXMI-029, AXMI-007, AXMI-008, AXMI-0080rf2, AXMI-009, AXMI-014, TIC807, TIC809, TIC810, TIC812, TIC127 and TIC128. In other embodiments where two *Lygus* inhibitory proteins other than a TIC853 protein are expressed in the plant, the two *Lygus* inhibitory proteins can comprise TIC809 and TIC810. In other embodiments of the method, both a first and a second insect pest can be controlled by the composition. In these embodiments of the method, the second insect pest can be inhibited by either the ribonucleotide sequence of the composition or by the protein other than a TIC853 protein of the composition. This second insect pest can be a lepidopteran insect pest. The second insect pest can be inhibited by a protein selected from the group consisting of a Cry1A protein, a Cry1B protein, a Cry1C, a Cry1A/Cry1F chimeric protein, and a Cry2Ab protein. In certain embodiments of the method of controlling at least one insect pest, the composition provides for a synergistic insect inhibitory effect. In other embodiments of the method of controlling at least one insect pest, the composition provides for an additive insect inhibitory effect. In the methods of controlling at least one insect pest, the composition can be a transgenic plant such as corn event MIR604 (U.S. Pat. No. 7,361,813 and published PCT application, WO 05/103301A2) which expresses a modified variant of Cry3Aa, corn event MON88017 (Published PCT application, WO 05/059103A2) which expressed a modified variant of Cry3Bb1, Corn event PV-ZMIR13 (MON863) (Published PCT application, WO 04/011601A2) which expressed a modified variant of Cry3Bb1, or any transgenic plant expressing an insect toxin such as a Cry1, a Cry2, a Cry3, a TIC807, a TIC127, a TIC128, a TIC810, a TIC851, a CryET70, ET29, a binary insecticidal protein CryET33 and CryET34, a binary insecticidal protein CryET80 and CryET76, a binary insecticidal protein ET29 and TIC810, a binary insecticidal protein TIC809 and TIC810, a binary insecticidal protein TIClOO and TIClOl, and a binary insecticidal protein PS149B1.

The invention also provides a method for protecting a plant from *Lygus* infestation comprising expressing a *Lygus* inhibitory amount of at least two different *Lygus* inhibitory agents in the plant, where the *Lygus* inhibitory agents comprise (i) a *Lygus* inhibitory amount of a TIC853 protein, where the TIC 853 protein comprises a polypeptide sequence has at least 88% sequence identity over a length of at least 300 amino acids of a corresponding polypeptide sequence contained within SEQ ID NO:6; (ii) a *Lygus* inhibitory amount of at least one *Lygus* inhibitory protein other than a TIC853 protein and/or (iii) a *Lygus* inhibitory amount of at least one ribonucleotide sequence that functions upon ingestion by the *Lygus* to inhibit a biological function within the *Lygus*. This essential biological function in *Lygus* can be provided by an essential protein or ribonucleic acid of the *Lygus*, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis. This essential biological function in *Lygus* can be inhibited by a ribonucleotide sequence that comprises from about 50 to about 5000 contiguous nucleotides exhibiting from about 80 to about 100% sequence identity to a nucleotide coding sequence selected from the group consisting SEQ ID NO:28 through SEQ ID NO:43. In certain embodiments of this method, the *Lygus* inhibitory protein other than a TIC853 protein is derived from *Bacillus thuringiensis*. The *Lygus* inhibitory protein other than TIC853 can be selected from the group consisting of AXMI-027, AXMI-036, AXMI-038, AXMI-018, AXMI-020, AXMI-021, AXMI-010, AXMI-003, AXMI-008, AXMI-006, AXMI-007, AXMI-009, AXMI-014, ET29, ET37, AXMI-004, AXMI-028, AXMI-029, AXMI-007, AXMI-008, AXMI-0080rf2, AXMI-009, AXMI-014, TIC807, TIC809, TIC810, TIC812, TIC127 and TIC128. In other embodiments where two *Lygus* inhibitory proteins other than a TIC853 protein are expressed in the plant, the two *Lygus* inhibitory proteins can comprise TIC809 and TIC810. In this method, a TIC853 insect inhibitory protein or protein fragment comprises a polypeptide sequence that has at least about 88% sequence identity over a length of at least 300 amino acids of a corresponding polypeptide sequence contained within SEQ ID NO:6. A TIC853 protein used in the method can also comprise a TIC853 insect inhibitory protein fragment of at least 300 amino acid residues in length. In certain embodiments of this method, expression of the *Lygus* inhibitory agents provides for a synergistic *Lygus* inhibitory effect. In other embodiments of this method, expression of the *Lygus* inhibitory agents provides for an additive *Lygus* inhibitory effect. By using this method, the plant can be protected from *Lygus hesperus* or *Lygus lineolaris*.

The invention further provides for isolated proteins, wherein the isolated protein comprises a polypeptide sequence of at least 9 amino acids in length that is contained within SEQ ID NO:6 and is not identical to a corresponding polypeptide sequence of at least 9 contiguous amino acids in length that is contained in TIC807 (SEQ ID NO:11) or Cry51Aa1 (SEQ ID NO:15). The isolated protein can have a polypeptide sequence at least 12, 16, 32, 50, 100, 150, 200, 250, or less than 300 amino acids in length. The isolated protein of at least 12, 16, 32, 50, 100, 150, 200, 250, or less than 300 amino acids in length can have a polypeptide sequence at least about 90%, 95%, or 99% sequence identity to a corresponding polypeptide sequence of equal length contained within SEQ ID NO:6. In certain embodiments, the polypeptide sequence of less than 300 amino acids has less than 88% sequence identity to a corresponding polypeptide sequence of less than 300 amino acids in length that is contained in TIC807 (SEQ ID NO:11) or Cry51Aa1 (SEQ ID NO:15). Isolated TIC853 proteins can also comprise one or more non-conserved amino acid residues selected from the group consisting of Y28, A125, S147, V213, R214, R216, E231, A265, and combinations thereof, where the indicated amino acid residues are found in a corresponding position of SEQ ID NO:6.

Isolated proteins of the invention also comprise insect inhibitory proteins of at least 300 amino acids in length that have at least about 88% sequence identity over a length of at least 300 amino acids of a corresponding polypeptide sequence contained within SEQ ID NO:6. In other embodiments, the insect inhibitory protein is at least 302, 304, 305, or 306 amino acids in length and has at least 88%, 90%, 95%, 98%, 99%, or 100% sequence identity to a corresponding amino acid sequence of equal length in SEQ ID NO:6. The isolated insect inhibitory protein of at least 300 amino acids can inhibit Lygus. In certain embodiments, the isolated insect inhibitory protein of at least 300 amino acids inhibits Lygus at a Lygus diet concentration of the protein of at least about 5 ppm, 50 ppm, 250 ppm, or 500 ppm. The isolated protein can also be the protein of SEQ ID NO:2 or SEQ ID NO:6. The isolated protein can further comprise a carrier protein. This carrier protein can be an albumin or a KLH protein. Isolated proteins of the invention can also further comprise a covalent modification selected from the group consisting of an indicator reagent, an amino acid spacer, an amino acid linker, a signal sequence, a chloroplast transit peptide sequence, a vacuolar targeting sequence, a stop transfer sequence, a transmembrane domain, a protein purification ligand, or a combination thereof. Isolated insect inhibitory TIC853 proteins can also comprise one or more non-conserved amino acid residues selected from the group consisting of Y28, A125, S147, V213, R214, R216, E231, A265, and combinations thereof, where the indicated amino acid residues are found in a corresponding position of SEQ ID NO:6.

The invention also provides for antibodies that specifically bind to a TIC853 protein or peptide epitope derived therefrom, where the TIC853 protein or epitope comprising at least 9 contiguous amino acids of SEQ ID NO:6 is not identical to a polypeptide sequence of at least 9 contiguous amino acids in length that is contained in SEQ ID NO:11 or SEQ ID NO:15 and where the antibody will not bind to a polypeptide of SEQ ID NO:11, SEQ ID NO:15, or a peptide epitope derived therefrom.

The invention further provides kits for detection of a TIC853 protein in a sample that comprises: (a) an antibody that specifically binds to a TIC853 protein or peptide epitope derived therefrom, where the protein or epitope comprises at least 9 contiguous amino acids of SEQ ID NO:6; and is not identical to a polypeptide sequence of at least 9 contiguous amino acids in length that is contained in SEQ ID NO:11 or SEQ ID NO:15 and where the antibody will not bind to a polypeptide of SEQ ID NO:11, SEQ ID NO:15, or a peptide epitope derived therefrom and (b) a control TIC853 protein or peptide epitope derived therefrom that comprises at least 9 contiguous amino acids of SEQ ID NO:6.

DETAILED DESCRIPTION OF THE PREFERRED EMBODIMENTS

I. Definitions

As used herein, the phrase "additive effect", in reference to insect inhibition, refers to an inhibitory effect obtained by combining at least two distinct insect inhibitory agents that is either: (a) quantitatively equivalent to the predicted additive effect of the combination of the two agents and/or is (b) qualitatively equivalent to the combination of effects obtained from each agent administered on its own. Examples of quantitative effects include, but are not limited to, changes in $LC_{50}$, $EC_{50}$, $IC_{50}$, percent mortality, or percent stunting values indicative of increased insect inhibitory activity against a known insect target of both insect inhibitory agents. Examples of additive qualitative effects include, but are not limited to, an expanded spectrum of insect inhibition (i.e., Hemipteran and lepidopteran insects) that reflects the simple combination of the spectrum exhibited by each insect inhibitory agent (i.e., the combination of Hemipteran insect inhibition provided by one agent and lepidopteran insect inhibition provided by another agent).

The term "Construct" as used herein refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e., operably linked.

The phrase "biological functional equivalents" as used herein refers to peptides, polypeptides and proteins that contain a sequence or structural feature similar to a TIC853 protein of the present invention, and which exhibit the same or similar insect inhibitory activity of a TIC853 protein of the present invention. Biological functional equivalents also include peptides, polypeptides and proteins that react with (i.e., specifically bind) to monoclonal and/or polyclonal antibodies raised against a TIC853 protein and that exhibit the same or similar insect inhibitory activity as a TIC853 protein.

As used herein, the phrase "corresponding polypeptide sequence contained within SEQ ID NO:6" refers to a polypeptide sequence within SEQ ID NO:6 that will yield the highest percent identity when aligned with the other polypeptide sequence.

As used herein, a "comparison window" refers to a conceptual segment of at least 6 contiguous positions, usually about 50 to about 100, more usually about 100 to about 150, in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Those skilled in the art should refer to the detailed methods used for sequence alignment in the Wisconsin Genetics Software Package Release 7.0, Genetics Computer Group, 575 Science Drive Madison, Wis., USA or refer to Ausubel et al., (1998) for a detailed discussion of sequence analysis.

The phrase "DNA construct" as used herein refers to any DNA molecule in which two or more ordinarily distinct DNA sequences have been covalently linked. Examples of DNA constructs include but are not limited to plasmids, cosmids, viruses, BACs (bacterial artificial chromosome), YACs (yeast artificial chromosome), plant minichromosomes, autonomously replicating sequences, phage, or linear or circular single-stranded or double-stranded DNA sequences, derived from any source, that are capable of genomic integration or autonomous replication. DNA constructs can be assembled by a variety of methods including, but not limited to, recombinant DNA techniques, DNA synthesis techniques, PCR (Polymerase Chain Reaction) techniques, or any combination of techniques.

The phrase "a heterologous promoter", as used herein in the context of a DNA construct, refers to either: (i) a promoter that is derived from a source distinct from the operably linked structural gene or (ii) a promoter derived from the same source as the operably linked structural gene, where the promoter's sequence is modified from its original form.

The phrase "high stringency hybridization conditions" refers to nucleic acid hybridization conditions comprising a salt concentration of about 1×SSC, a detergent concentration of about 0.1% SDS, and a temperature of about 50 degrees Celsius, or equivalents thereof.

The term "homolog" as used herein refers to a gene related to a second gene by identity of either the DNA sequences or the encoded protein sequences. Genes that are homologs can be genes separated by the event of speciation (see "ortholog"). Genes that are homologs may also be genes separated by the event of genetic duplication (see "paralog"). Homologs can be from the same or a different organism and may perform the same biological function in either the same or a different organism.

The term "insect" as used herein refers to any embryonic, larval, nymph or adult form of an Arachnid, Coleopteran, Ctenophalides, Dipteran, Hemipteran, Homopteran, Heteropteran, Hymenopteran or Lepidopteran insect.

The phrase "an insect inhibitory agent' as used herein refers to any molecule that when presented to the insect in the insect diet causes a stunting of growth or mortality to the insect. The "agent" can be a toxin protein, dsRNA, protein belonging to a class other than an insect toxin, a molecule that causes stunting or mortality in the insect that is produced through the expression of a transgene or transgenes in a bacteria, fungi or plant or a chemical seed treatment.

The phrase "an insect inhibitory amount", refers to an amount of an agent, a TIC853 polypeptide, a ribonucleotide, or a protein other than a TIC853 protein that results in any measurable inhibition of insect growth, insect development, insect reproduction, insect feeding behavior, insect mating behavior and/or any measurable decrease in the adverse effects caused by insect feeding on a plant. Similarly, a "Lygus inhibitory amount" refers to an amount of a TIC853 polypeptide, a ribonucleotide, or a protein other than a TIC853 protein that results in any measurable inhibition of Lygus growth, Lygus development, Lygus reproduction, Lygus feeding behavior, Lygus mating behavior and/or any measurable decrease in the adverse effects caused by Lygus feeding on a plant. The phrase is similarly applicable when referring to activity of the applicable protein upon Colorado potato beetle (CPB).

The phrase "processed product of at least one plant part", refers to a composition that comprises a feed, a meal, a flour, an extract, a homogenate, wherein the feed, meal, flour, extract, or homogenate is obtained from at least one plant part. In certain embodiments, the commodity product can comprise lint, oil, meal, or hulls. In certain embodiments, the processed plant product can be obtained from at least one plant part that is a stem, a leaf, a root, a flower, a tuber, or a seed.

The phrase "related protein" refers to a protein sequence which is a homolog (derived from a gene related to a second gene by descent from a common ancestral DNA sequence), an ortholog (derived from genes in different species that evolved from a common ancestral gene by speciation which retain the same function in the course of evolution) or a paralog (derived from genes related by duplication within a genome which evolve new functions such as genes encoding related insect toxin proteins with different target species profiles, for example). The coding sequence or protein sequence of a related protein will share substantial homology with respect to sequences encoding the TIC853 toxin protein or the protein sequence of the TIC853 toxin.

The term "regeneration" as used herein refers to any method of obtaining a whole plant from any one of a seed, a plant cell, a group of plant cells such as embryos and meristems, plant callus tissue, or an excised piece of a plant.

The phrase "ribonucleotide sequence that functions upon ingestion by the insect pest to inhibit a biological function" refers to RNA sequence that comprises a sequence that is substantially homologous to an RNA molecule encoded by a nucleotide sequence within the genome of the insect, that provides for inhibition of the insect.

As used herein, the term "substantially homologous" or "substantial homology", with reference to a nucleic acid or polypeptide sequence, refers to a nucleotide or polypeptide sequence that has about 65% to about 70% sequence identity, or more preferably from about 80% to about 85% sequence identity, or most preferable from about 90% to about 95% sequence identity, to about 99% or 100% sequence identity, with another nucleotide or polypeptide sequence.

As used herein, the phrase "synergistic effect", in reference to insect inhibition, refers to an inhibitory effect obtained by combining at least two distinct insect inhibitory agents that is either: (a) quantitatively greater than the predicted additive effect of the combination of the two agents and/or is (b) qualitatively distinct from any effects obtained from either agent administered on its own. Examples of quantitative effects include, but are not limited to, changes in $LC_{50}$, $EC_{50}$, $IC_{50}$, percent mortality, or percent stunting values indicative of increased insect inhibitory activity against a known insect target of both insect inhibitory agents. Examples of synergistic qualitative effects include, but are not limited to, an expanded spectrum of insect inhibition (i.e., Hemipteran, Homopteran, Coleopteran, and Lepidopteran insects inhibition) that does not reflect the simple combination of the spectrum exhibited by each insect inhibitory agent alone (i.e., the combination of Hemipteran insect inhibition provided by one agent and lepidopteran insect inhibition provided by another agent).

The phrase "TIC853 protein" as used herein refers to proteins comprising at least 9 to 306 amino acids that display at least 88% sequence identity to a corresponding polypeptide sequence of equal length that is contained within SEQ ID NO:6.

The phrase "TIC853 related protein" as used herein refers to an insect inhibitory protein of at least 265 amino acids that display at least 45% sequence identity to a corresponding polypeptide sequence contained within SEQ ID NO:6.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. Nucleic acid sequences that can be operably linked include, but are not limited to, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions (i.e., T-DNA border sequences, site specific recombinase recognition sites, integrase recognition sites), sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences) and sequences that provide replication functions (i.e., bacterial origins of replication, autonomous replication sequences, centromeric sequences).

As used herein, the phrases or terms "sequence identity", "sequence similarity" or "homology" is used to describe sequence relationships between two or more nucleotide or two or more protein sequences. The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence.

The term "transformation" as used herein refers to a process of introducing an exogenous DNA sequence (e.g., a vector, a recombinant DNA molecule) into a cell or protoplast in which that exogenous DNA is incorporated into a chromosome or is capable of autonomous replication.

The phrase "transgenic plant" refers to a plant or progeny thereof derived from a transformed plant cell or protoplast, wherein the plant DNA contains an introduced exogenous DNA molecule not originally present in a native, non-transgenic plant of the same species.

The phrases "stabilized RNA", "stabilized dsRNA", and "stabilized siRNA" refer to combinations of sense-oriented and anti-sense-oriented, transcribed RNA separated by short sequences that permit formation of a hairpin or stem loop structure in the RNA molecule.

The phrase "vascular tissue" as used herein refers to any tissues or cells contained within the vascular bundle of a plant, including, but not limited to, phloem, protophloem, metaphloem, xylem, protoxylem, or metaxylem cells or tissues.

The term "vector" as used herein refers to any recombinant polynucleotide construct that may be used for the purpose of transformation, i.e., the introduction of heterologous DNA into a host cell.

II. Polynucleotides of the Invention

A variety of polynucleotides that encode TIC853 insect inhibitory proteins are contemplated by this invention. Such polynucleotides are useful for production of TIC853 insect inhibitory proteins in host cells when operably linked to suitable promoter, transcription termination and/or polyadenylation sequences. Such polynucleotides are also useful as probes for isolating homologous or substantially homologous polynucleotides that encode TIC853 proteins.

One source of polynucleotides that encode a TIC853 protein is the *Bacillus thuringiensis* strain which contains the TIC853 polynucleotide of SEQ ID NO:5 that encodes the TIC853 polypeptide of SEQ ID NO:6. This polynucleotide sequence was originally isolated from a *Bacillus thuringiensis* host and is thus suitable for expression of the encoded TIC853 polypeptide in other bacterial hosts. For example, SEQ ID NO:5 can be used to express TIC853 protein in bacterial hosts that include but are not limited to, *Agrobacterium*, a *Bacillus*, an *Escherichia*, a *Salmonella*, a *Pseudomonas*, and a *Rhizobium* bacterial host cells. The SEQ ID NO:5 probes are also useful as probes for isolating homologous or substantially homologous polynucleotides that encode TIC853 proteins. Such probes can be used to identify homologous or substantially homologous polynucleotides derived from *Bacillus* strains. Alternatively, other polynucleotides that encode TIC853 proteins can be obtained by PCR amplification of nucleic acids obtained from a *Bacillus thuringiensis* strain which contains the TIC853 polynucleotide of SEQ ID NO:5 or a variant thereof. TIC853 proteins obtained by PCR amplification of nucleic acids obtained from a *Bacillus thuringiensis* strain which contains a TIC853 polynucleotide of SEQ ID NO:5 or a variant thereof including, but are not limited to, the TIC852 protein of SEQ ID NO:2. Polynucleotides that encode the TIC852 protein of SEQ ID NO:2 include, but are not limited to, SEQ ID NO:1.

Another source of polynucleotides that encode TIC853 or TIC852 polynucleotides are deposited *E. coli* strains. *Escherichia coli* strain K12 harbors the vector pMON102351 containing a polynucleotide that encodes the TIC852 polypeptide of SEQ ID NO:2, was deposited on Mar. 28, 2008 with the Agricultural Research Culture Collection, Northern Regional Research Laboratory (NRRL), Peoria, Ill., USA, and has Accession No. NRRL B-50129. *Escherichia coli* strain K12 harbors the vector pMON102352 containing a polynucleotide that encodes the TIC853 polypeptide of SEQ ID NO:6, was deposited on Mar. 28, 2008 with the Agricultural Research Culture Collection, Northern Regional Research Laboratory (NRRL), Peoria, Ill., USA, and has Accession No. NRRL B-50130.

Polynucleotides that encode TIC853 proteins can also be synthesized de novo from a TIC853 polypeptide sequence. The sequence of the polynucleotide gene can be deducted from a TIC853 polypeptide sequence through use of the genetic code. Computer programs such as "BackTranslate" (GCG™ Package, Acclerys, Inc. San Diego, Calif.) can be used to convert a peptide sequence to the corresponding nucleotide sequence that encodes the peptide. Examples of a TIC853 polypeptide sequences that can be used to obtain corresponding nucleotide encoding sequences include, but are not limited to, the TIC853 polypeptide sequence of SEQ ID NO:6.

Furthermore, synthetic TIC853 polynucleotide sequences of the invention can be designed so that they will be expressed in plants. U.S. Pat. No. 5,500,365 describes a method for synthesizing plant genes to improve the expression level of the protein encoded by the synthesized gene. This method relates to the modification of the structural gene sequences of the exogenous transgene, to cause them to be more efficiently transcribed, processed, translated and expressed by the plant. Features of genes that are expressed well in plants include elimination of sequences that can cause undesired intron splicing or polyadenylation in the coding region of a gene transcript while retaining substantially the amino acid sequence of the toxic portion of the insecticidal protein. A similar method for obtaining enhanced expression of transgenes in monocotyledonous plants is disclosed in U.S. Pat. No. 5,689,052. Synthetic TIC853 polynucleotide sequences that encode a TIC853 protein include, but are not limited to, the polynucleotides of SEQ ID NOs:16, 17, 18, and 19.

III. Isolated Oligonucleotides, Kits and Methods for Isolation and/or Detection of Polynucleotides that Encode TIC853 Proteins Isolated oligonucleotides for identifying, detecting, or isolating polynucleotides that encode TIC853 proteins are also provided by the present invention.

In one embodiment, the isolated oligonucleotides comprise at least 12 contiguous nucleotides of a sequence contained within the *Bacillus thuringiensis* TIC853 encoding gene of SEQ ID NO:5 or contained within the complement of SEQ ID NO:5 are not identical to any 12 contiguous nucleotides of SEQ ID NO:10 or SEQ ID NO:14 or to any 12 contiguous nucleotides of the complements of SEQ ID NO:10 or SEQ ID NO:14. Such oligonucleotides can be used in hybridization or PCR based methods for identifying or isolating polynucleotides that encode TIC853 proteins from strains of *Bacillus thuringiensis*. Such oligonucleotides can also be used to confirm the presence or absence of a TIC853-encoding polynucleotide in a host cell. It is further recognized that the oligonucleotides can be used to mutagenize SEQ ID NO:5 when they comprise additional sequences that comprise mismatches to SEQ ID NO:5. Such "mutagenesis" oligonucleotides are useful for identification of TIC853 variants with enhanced insect inhibitory activity.

In another embodiment, the isolated oligonucleotides comprise at least 12 contiguous nucleotides of a sequence contained within the polynucleotide of SEQ ID NOs:16, 17, 18, or 19 or contained within the complement of SEQ ID NOs:16, 17, 18, or 19 that are not identical to any 12 contiguous nucleotides of SEQ ID NO:54 or to any 12 contiguous nucleotides of the complements of SEQ ID NO:54. The polynucleotide of SEQ ID NOs:16, 17, 18, or 19 is specifically designed for expression in transgenic plants and encode the TIC853 protein of SEQ ID NO:6. Such oligonucleotides can be used in hybridization or PCR based methods for detecting SEQ ID NOs:16, 17, 18, or 19 polynucleotides in samples derived from transgenic plants. When the sample is a ribonucleic acid sample, the oligonucleotides can be used in hybridization or PCR based methods to quantitate levels of TIC853 transgene expression. When the sample is a deoxyribonucleic acid sample, the oligonucleotides can be used in hybridization or PCR based methods to determine the presence or absence of the TIC853 transgene in the sample. It is also anticipated that the SEQ ID NOs:16, 17, 18, or 19 derived oligonucleotides can be used to determine the presence or absence of a TIC853 transgene in a deoxyribonucleic acid sample derived from a commodity product. Given the exquisite sensitivity of certain nucleic acid detection methods that employ oligonucleotides, it is anticipated that the SEQ ID NOs:16, 17, 18, or 19 derived oligonucleotides can also be used to detect a TIC853 transgene in commodity products derived from pooled sources where only a fraction of the commodity product is derived from a transgenic plant containing SEQ ID NOs:16, 17, 18, or 19. It is further recognized that the oligonucleotides can be used to mutagenize SEQ ID NOs: 16, 17, 18, or 19 when they comprise additional sequences that comprise mismatches to SEQ ID NOs:16, 17, 18, or 19. Such "mutagenesis" oligonucleotides are useful for identification of TIC853 variants with enhanced insect inhibitory activity and/or enhanced expression in transgenic plant host cells.

It is of course understood that the oligonucleotides of the invention can further comprise additional sequences that are not identical or complementary to the polynucleotide sequences that encode TIC853 proteins. Additional sequences may include but are not limited to, sequences used as adapters that facilitate cloning, mutagenesis, or detection. The oligonucleotides of the invention can further comprise additional covalent modifications. Covalent modifications would include, but are not limited to, detectable labels such as isotopes, fluorophores, and haptens. Biotin is one particularly useful hapten.

Kits for detection of a TIC853 polynucleotide sequence in a sample that comprise at least one oligonucleotide that specifically hybridizes to the polynucleotide sequence of SEQ ID NOs: 16, 17, 18, or 19 or a complement thereof are further contemplated by this invention. In the context of the kits of this invention, the term "specifically hybridize" means that the oligonucleotides will hybridize and detect SEQ ID NOs:16, 17, 18, or 19 in a sample from a transgenic cell or plant transformed with one or more copies of SEQ ID NOs:16, 17, 18, or 19 but will not specifically hybridize and detect any sequences in a control non-transgenic cell or plant that (i) does not contain SEQ ID NOs:16, 17, 18, or 19 and will not specifically hybridize and detect any sequences in a transgenic plant comprising SEQ ID NO:54. These kits can also comprise a control polynucleotide that hybridizes to said oligonucleotide, instructions for use, and/or reagents for hybridizing or detecting hybridization of the oligonucleotides to SEQ ID NOs:16, 17, 18, or 19. In certain applications, including but not limited to those application that use a Polymerase Chain Reaction, the kits will naturally comprise more than one oligonucleotide that specifically hybridizes to the polynucleotide sequence of SEQ ID NOs: 16, 17, 18, or 19. The kit can further comprise instructions describing how to use the kit contents to detect a TIC853 encoding polynucleotide sequence. The kit instructions can be provided in any manner, including but not limited to, being provided within the packaging of the kit, on the packaging of the kit, on a website referred to in the kit, and/or any combination thereof.

IV. Degenerate Oligonucleotides, Degenerate Oligonucleotide Compositions and Methods of Use Degenerate oligonucleotides, compositions comprising degenerate oligonucleotides, and methods of using such oligonucleotides to identify, detect or isolate TIC853 protein encoding polynucleotides are also contemplated by this invention. Although such degenerate oligonucleotides are derived from SEQ ID NO:6, those skilled in the art appreciate that such oligonucleotides can be used to identify a variety of TIC853 proteins and TIC853-related proteins. Such TIC853 proteins are anticipated to have at least 88%, at least 90%, at least 95%, at least 98%, at least 99%, or 100% amino acid identity over a length of at least 300 amino acids of a corresponding polypeptide sequence contained in SEQ ID NO:6 and to have insect inhibitory activity. The TIC853 related proteins have at least 45% sequence identity to SEQ ID NO:6 and have insect inhibitory activity.

The design of degenerate oligonucleotide sequences based on particular peptide sequences is accomplished through use of the genetic code, whereby codons corresponding to each of the encoded amino acids are synthesized. Degenerate oligonucleotides can comprise either pool of oligonucleotides comprising all of the potential sequences that encode a given peptide sequence. Considerations involved in the design and use of degenerate oligonucleotide primers or probes are well known to those skilled in the art (see Molecular Cloning: A Laboratory Manual (Third Edition), Sambrook and Russell, Cold Spring Harbor Press, 2001).

Compositions comprising at least two degenerate oligonucleotide primers of at least 12 nucleotides from the polypeptide sequence of SEQ ID NO:6 where the degenerate oligonucleotide primers would not hybridize under stringent conditions to SEQ ID NO:10 or SEQ ID NO:14 or to any 12 contiguous nucleotides of the complements of SEQ ID NO:10 or SEQ ID NO:14 are provided herein. Such compositions can be used in either hybridization or polymerase chain reaction based methods for isolation or detection of polynucleotides that encode TIC853 proteins or TIC853 related proteins. The degenerate oligonucleotides of this composition can further comprise additional sequences that are not identical or complementary to the polynucleotide sequences that encode TIC853 proteins. Additional sequences may include but are not limited to, sequences used as adapters that facilitate cloning, mutagenesis, or detection. The degenerate oligonucleotides of the invention can further comprise additional covalent modifications. Covalent modifications would include, but are not limited to, detectable labels such as an isotopes, fluorophores, and haptens. Biotin is one particularly useful hapten.

Use of the degenerate oligonucleotide primers in PCR based methods of isolating or detecting polynucleotides that encode a TIC853 protein or a TIC853 related protein in a sample is specifically contemplated. In brief, a pair of degenerate oligonucleotide primers capable of producing an amplicon is selected and used in a polymerase chain reaction with a sample that contains a polynucleotide that encodes a TIC853 protein or a TIC853 related protein. A suitable source of samples for this method includes, but is not limited to, various Bacillus thuringiensis strains. The degenerate oligonucleotides are capable of producing an amplicon when the oligonucleotides correspond to predicted sense and antisense strand sequences and are in a 5' to 3' orientation that will prime DNA polymerase-mediated synthesis of a DNA strand that is complementary to the other opposing oligonucleotide. The degenerate oligonucleotide primers are derived from a TIC853 polypeptide sequence of SEQ ID NO:6. This amplicon can be detected by use of an intercalating dye to produce an amplicon. The amplicon can also be isolated by cloning the isolated amplicon fragment into a plasmid, cosmid, bacteriophage, or other cloning vector. Once cloned, this amplicon can be further characterized by sequencing to determine the percent identity of the amplicon-encoded protein to TIC853 (SEQ ID NO:6). It is anticipated that polynucleotides encoding TIC853 proteins of at least 88%, at least 95% identity, or at least 98% to SEQ ID NO:6 and TIC853-related proteins of at least 45% identity to SEQ ID NO:6 can be detected or isolated by these methods. Such TIC853 proteins or a TIC853 related proteins can subsequently be screened for insect inhibitory activity.

The degenerate TIC853 oligonucleotides can also be used as probes in hybridization based methods of detecting or isolating polynucleotides that encode TIC853 proteins or a TIC853 related proteins. Methods for detecting a polynucleotide that encodes a TIC853 protein in a sample first comprise selecting a degenerate oligonucleotide or collection of degenerate oligonucleotide derived from a TIC853 polypeptide sequence of SEQ ID NO:6. These degenerate oligonucleotides may further comprise detectable labels such as isotopes, fluorophores, and haptens. Biotin is one particularly useful hapten. The samples include, but are not limited to, samples derived from various Bacillus thuringiensis strains. The sample can be a library of plasmid, cosmid or bacteriophage clones derived from one or more Bacillus thuringiensis strains. The degenerate oligonucleotide or collection of degenerate oligonucleotides are hybridized to the sample under suitable hybridization stringency conditions. These conditions are related to the length of the degenerate oligonucleotide(s), the degree of degeneracy, their G+C content, the desired or projected percent sequence identity of target sequences in the sample and other factors. Hybridization to a polynucleotide is detected by methods including, but not limited to, radiometric, fluorometric, luminometric, and/or ELISA-based methods. Following detection, the polynucleotide can be isolated by serial dilution and re-hybridization. All of the above listed steps of degenerate oligonucleotide design, oligonucleotide labeling, library preparation, hybridization, detection and isolation are well know to those skilled in the art (see Molecular Cloning: A Laboratory Manual (Third Edition), Sambrook and Russell, Cold Spring Harbor Press, 2001). It is anticipated that polynucleotides encoding TIC853 proteins of at least 88% or at least 95% identity to SEQ ID NO:6 and TIC853-related proteins of at least 45% identity to SEQ ID NO:6 can be detected or isolated by these methods. Such TIC853 proteins or a TIC853 related proteins can subsequently be screened for insect inhibitory activity following expression in an acrystallifeorus Bacillus thuringiensis strain. The TIC853 or TIC853 related proteins can inhibit a Hemipteran pest such as Lygus. Alternatively, the TIC853 or TIC853 related proteins can inhibit other insect pests including Arachnid, Coleopteran, Ctenophalides, Dipteran, Hymenopteran or Lepidopteran pests, or can inhibit both Hemipteran pests and other families of insect pests.

V. DNA Constructs Comprising TIC853 Bacterial Expression Cassettes

To express TIC853 proteins in bacterial hosts, polynucleotides that encode TIC853 are operably linked to suitable promoters and transcriptional termination sequences that function in bacterial hosts to yield bacterial expression cassettes. Promoters and termination signals that function in bacterial cells can be derived from bacterial genes, bacteriophage genes or synthetic methods. These expression cassettes can then be transferred to suitable bacterial vectors that comprise replication origins and selectable markers via standard recombinant DNA techniques. Polynucleotides that can be used to express TIC853 proteins in bacteria include, but are not limited to, the TIC852 nucleotide sequence (SEQ ID NO:1), the TIC853 nucleotide sequence of SEQ ID NO:5 or the non-native TIC853 nucleotide sequence of SEQ ID NO:7.

In the practice of this invention, bacterial promoters, termination signals and vectors that function in *Bacillus* hosts are particularly useful for expression of TIC853 polypeptides. In many instances, the TIC853 gene comprising its endogenous promoter and termination sequences can be used for expression of TIC853 proteins in *Bacillus* host cells that include but are not limited to, *Bacillus thuringiensis* hosts. For such experiments, use of a shuttle vector that functions in both *E. coli* and *Bacillus* hosts is particularly useful. Examples of such shuttle vectors include, but are not limited to, vectors such as pEG854 described in U.S. Pat. No. 5,650,308. These shuttle vectors include antibiotic resistance marker genes permitting transformation of *Bacillus* hosts. Preferred *Bacillus thuringiensis* hosts include, but are not limited to, acrystalliferous (Cry protein deficient) *B. thuringiensis* host strains such as EG10368 and EG10650 (described in U.S. Pat. No. 5,759,538). When the TIC853 protein is expressed in a acrystalliferous (Cry protein deficient) *B. thuringiensis* host strains, the TIC853 protein is easily isolated as a parasporal crystal following induction of sporulation in the host cells. This facile *Bacillus thuringiensis* expression system can thus be used to test large numbers of TIC853 protein variants for insect inhibitory activity.

VI. DNA Constructs Comprising TIC853 Plant Expression Cassettes

The construction of expression cassettes for use in monocotyledonous plants or dicotyledonous plants is well established. Expression cassettes are DNA constructs where various promoter, coding, and polyadenylation sequences are operably linked. In general, expression cassettes typically comprise a promoter that is operably linked to a sequence of interest which is operably linked to a polyadenylation or terminator region. In certain instances including, but not limited to, the expression of transgenes in monocot plants, it may also be useful to include an intron sequence. When an intron sequence is included, it is typically placed in the 5' untranslated leader region of the transgene. In certain instances, it may also be useful to incorporate specific 5' untranslated sequences in a transgene to enhance transcript stability or to promote efficient translation of the transcript.

A variety of promoters can be used in the practice of this invention. One broad class of useful promoters is referred to as "constitutive" promoters in that they are active in most plant organs throughout plant development. For example, the promoter can be a viral promoter such as a CaMV35S or FMV35S promoter. The CaMV35S and FMV35S promoters are active in a variety of transformed plant tissues and most plant organs (e.g., callus, leaf, seed and root). Enhanced or duplicate versions of the CaMV35S and FMV35S promoters are particularly useful in the practice of this invention (U.S. Pat. No. 5,378,619, incorporated herein by reference in its entirety). Other useful nopaline synthase (NOS) and octopine synthase (OCS) promoters (which are carried on tumor-inducing plasmids of *A. tumefaciens*), the cauliflower mosaic virus (CaMV) 19S promoters, a maize ubiquitin promoter (U.S. Pat. No. 5,510,474), the rice Act1 promoter and the Figwort Mosaic Virus (FMV) 35S promoter (see e.g., U.S. Pat. No. 5,463,175; incorporated herein by reference in its entirety). It is understood that this group of exemplary promoters is non-limiting and that one skilled in the art could employ other promoters that are not explicitly cited here in the practice of this invention.

Promoters that are active in certain plant tissues (i.e., tissue specific promoters) can also be used to drive expression of TIC853 proteins or other insect inhibitory agents. Since certain Hemipteran insect pests are "piercing/sucking" insect that typically feed by inserting their proboscis into the vascular tissue of host plants, promoters that direct expression of insect inhibitory agents in the vascular tissue of the transgenic plants are particularly useful in the practice of this invention. Various Caulimovirus promoters, including but not limited to the CaMV35S, CaMV19S, FMV35S promoters and enhanced or duplicated versions thereof, typically deliver high levels of expression in vascular tissues and are thus useful for expression of TIC853 proteins or other insect inhibitory agents. Phloem-limited viruses such as the rice tungro virus (Bhattacharyya-Pakrasi et al., Plant J. 4[1] 71-79, 1993) and the commelina yellow mottle virus (Medberry et al., Plant Cell 4:185-192, 1992) also contain useful promoters that are active in vascular tissues. For control of Hemipteran insects that feed on phloem, phloem cell-specific or phloem-preferred promoters can be used to express TIC853 proteins or other insect inhibitory agents in phloem of transgenic plants. Examples of useful phloem specific promoters include, but are not limited to, PP2-type gene promoters (U.S. Pat. No. 5,495,007), sucrose synthase promoters (Yang and Russell, Proc. Natl. Acad. Sci. USA 87:4144-4148, 1990), glutamine synthetase promoters (Edwards et al., Proc. Natl. Acad. Sci. USA 87:3459-3463, 1990), and phloem-specific plasma membrane H+-ATPase promoters (DeWitt et al., Plant J. 1[1]: 121-128, 1991), prunasin hydrolase promoters (U.S. Pat. No. 6,797,859), and a rice sucrose transporter (U.S. Pat. No. 7,186,821). For control of Hemipteran pests that feed on xylem tissue, a variety of promoters that are active in xylem tissue including, but not limited to, protoxylem or metaxylem can be used. Promoters active in xylem tissue include, but are not limited to, promoters associated with phenylpropanoid biosynthetic pathways, such as the phenylalanine ammonia-lyase (PAL) promoters, cinnamate 4-hydroxylase (C4H) promoters, coumarate 3-hydroxylase promoters, O-methyl transferase (OMT) promoters, 4-coumarate:CoA ligase (4CL) promoters (U.S. Pat. No. 6,831,208), cinnamoyl-CoA reductase (CCR) promoters and cinnamyl alcohol dehydrogenase (CAD) promoters.

Transcriptional enhancer elements can also be used in conjunction with any promoter that is active in a plant cell or with any basal promoter element that requires an enhancer for activity in a plant cell. Transcriptional enhancer elements can activate transcription in various plant cells and are usually 100-200 base pairs long. The enhancer elements can be obtained by chemical synthesis or by isolation from regulatory elements that include such elements, and can comprise additional flanking nucleotides that contain useful restriction enzyme sites to facilitate subsequence manipulation. Enhancer elements can be typically placed within the region 5' to the mRNA cap site associated with a promoter, but can also be located in regions that are 3' to the cap site (i.e., within a 5' untranslated region, an intron, or 3' to a polyadenylation site) to provide for increased levels of expression of operably linked genes. Enhancer elements can also be multimerized (provided in any finite number of linked copies) to provide for increased expression of operably linked genes. Multimerized enhancers include, but are not limited to, duplicate, triplicate, or quadruplicate copies of enhancers in any orientation or combination of orientations. Enhancers are often derived from plant viral promoters, particularly those of the double-stranded DNA Cauli-moviridae group comprising the caulimoviruses and the badnaviruses. The plant viral promoters or derived plant viral enhancers can provide strong constitutive expression of operably linked genes in transgenic plants. Enhancers derived from fragments of these promoters have been demonstrated to effectively enhance the performance of promoters driving the expression of transgenes in plants. Examples of plant viruses useful for isolating enhancers include, but are not limited to, the cauliflower mosaic virus (CaMV) (see, e.g., Odel et al., Nature 313:810, 1985), the figwort mosaic virus (U.S. Pat. No. 5,378,619), the carnation etched ring virus (CERV) (Hull et al., (1986) EMBO Journal 5:3083-3090), the cassava vein mosaic virus (CsVMV) (Calvert et al., (1995) J. Gen. Virol. 76: 1271-1278 and U.S. Pat. No. 6,963,021), the mirabilis mosaic virus (MMV) (Dey et al., (1999) Plant Mol. Biol. 40:771-82), the Cestrum yellow leaf curling virus (CmYLCV) (Stavolone et al., (2003) Plant Mol. Biol. 53:663-73), the cotton leaf curl Multan virus (CLCuMV) (Xie et al., (2003) Plant Mol. Biol. 53:1-14), the commelina yellow mottle virus (CoYMV) (U.S. Pat. No. 6,963,021) and the peanut chlorotic streak caulimovirus (PCLSV) (U.S. Pat. No. 5,850,019). Duplications of enhancers are used in enhanced versions of the CaMV 35S and FMV 35S promoters.

Various 5' untranslated leader sequences can also be operably linked to a coding sequence of interest in a plant expression cassette. Thus the plant expression cassette can contain one or more 5' non-translated leader sequences which serve to increase expression of operably linked nucleic acid coding sequences encoding either TIC853 or other proteins of interest. Without seeking to be limited by theory, such 5' untranslated leader sequences can increase the translational efficiency of the resultant mRNA and/or increase the stability of the resultant mRNA to provide increased levels of the operably linked and encoded protein of interest in the transgenic plant. Examples of other useful 5' leader sequences include, but are not limited to, the dSSU 5', PetHSP70 5', and GmHSP17.9 5' untranslated leader sequences. A translational enhancer sequence derived from the untranslated leader sequence from the mRNA of the coat protein gene of alfalfa mosaic virus coat protein gene can be placed between the promoter and the gene of interest to increase translational efficiency of the operably linked gene of interest (U.S. Pat. No. 6,037,527).

An intron may also be included in the DNA expression construct, especially in instances when the sequence of interest is to be expressed in monocot plants. For monocot plant use, introns such as the maize hsp70 intron (U.S. Pat. No. 5,424,412; incorporated by reference herein in its entirety), the maize ubiquitin intron, the Adh intron 1 (Callis et al., 1987 Genes Dev. 1: 1183-1200), the sucrose synthase intron (Vasil et al., 1989, Plant Physiol., 91, 1575-1579) or the rice Act1 intron (McElroy et al., 1991, MGG, 231, 150-160.) can be used. Dicot plant introns that are useful include introns such as the CAT-1 intron (Cazzonnelli and Velten, 2003, Plant Molecular Biology Reporter, 21, 271-280), the pKANNIBAL intron (Wesley et al., 2001 Plant Journal, 27, 581-590), the PIV2 intron (Mankin et al., 1997, Plant Molecular Biology Reporter, 15, 186-196) and the "Super Ubiquitin" intron (U.S. Pat. No. 6,596,925) that have been operably integrated into transgenes. It is understood that this group of exemplary introns is non-limiting and that one skilled in the art could employ other introns that are not explicitly cited here in the practice of this invention.

In other embodiments of the invention, sequences encoding peptides that provide for the localization of a TIC853 protein in subcellular organelles can be operably linked to the sequences that encode the TIC853 polypeptide. TIC853 polypeptides that are operably linked to a signal peptide are expected to enter the secretion pathway and can be retained by organelles such as the endoplasmic reticulum (ER) or targeted to the vacuole by operably linking the appropriate retention or targeting peptides to the C-terminus of the TIC853 polypeptide. Examples of vacuolar targeting peptides include, but are not limited to, a CTPP vacuolar targeting signal from the barley lectin gene. Examples of ER targeting peptides include, but are not limited to, a peptide comprising a KDEL amino acid sequence. Without seeking to be limited by theory, localization of TIC853 polypeptides in either the endoplasmic reticulum or the vacuole can provide for desirable properties such as increased expression in transgenic plants and/or increased efficacy in inhibiting insects in transgenic plants.

Localization of TIC853 proteins to plant plastids including, but not limited to, chloroplasts is specifically contemplated herein. Plastid localization is typically accomplished by the operable linkage of a chloroplast transit peptide sequence to the N-terminus of the TIC853 protein. Chloroplast transit peptides (or CTPs) that can be used to localize TIC853 proteins in transgenic plants can be derived from nuclear encoded plant proteins that are targeted to plastids. Nuclear encoded plant proteins that are targeted to plastids include, but are not limited to, proteins involved in lipid, starch, or amino acid biosynthesis, as well as proteins involved in photosynthesis. Specific chloroplast transit peptides that can be used include, but are not limited to, CTPs from nuclear encoded Granule Bound Starch Synthase genes, plastidial Fatty Acid Desaturase genes, EPSPS genes, and RUBISCO small subunit genes. An exemplary CTP is the *Arabidopsis* EPSPS CTP. Nucleic acids encoding an *Arabidopsis* EPSPS CTP that is operably linked to a TIC853 protein include, but are not limited to, SEQ ID NOs:20, 21, 22, and 23. Without seeking to be limited by theory, localization of TIC853 polypeptides in plastids can provide for desirable properties such as increased expression in transgenic plants and/or increased efficacy in inhibiting insects in transgenic plants. Without being limited by theory, increased expression of TIC853 protein in a transgenic plant can provide for increased levels of insect inhibition, an expanded spectrum of insect pest inhibition, and/or an increased degree of insect pest resistance management.

As noted above, the sequence of interest can also be operably linked to a 3' non-translated region containing a polyadenylation signal. This polyadenylation signal provides for the addition of a polyadenylate sequence to the 3' end of the RNA. The *Agrobacterium* tumor-inducing (Ti) plasmid nopaline synthase (NOS) gene 3' and the pea ssRUBISCO E9 gene 3' un-translated regions contain polyadenylate signals and represent non-limiting examples of such 3' untranslated regions that can be used in the practice of this invention. It is understood that this group of exemplary polyadenylation regions is non-limiting and that one skilled in the art could employ other polyadenylation regions that are not explicitly cited here in the practice of this invention.

Illustrative and non-limiting TIC853 plant expression cassettes comprising an enhanced CaMV35S promoter that is operably linked to an Hsp17.9 5' untranslated leader, a TIC853 coding region appropriate for expression in plants and a CaMV 35S polyadenylation region are provided herein as SEQ ID NOs:24, 25, 26, and 27.

It is anticipated that any of the aforementioned plant expression cassettes can be used with a polynucleotide designed so that they will express a TIC853 protein in plants. Plant expression cassettes comprising SEQ ID NOs:16, 17, 18, 19, or an insect inhibitory protein encoding portion thereof, that will provide for expression of a TIC853 protein in a plant are provided herein. A preferred plant expressable polynucleotide sequence can be evaluated for optimal expression in protoplast cells derived from the plant species of interest or a related plant species. After selection of those designed polynucleotide sequences which give the best expression, the selected sequences are then transformed into stable plants for continued selection. The plant expression cassette shown as SEQ ID NO:16 was designed for optimal expression in monocot plants that include, but are not limited to, corn, wheat, sugar cane and rice. The plant expression cassette shown as SEQ ID NO:17 was designed for optimal expression in *Arabidopsis* and other Cruciferous plants. The plant expression cassette shown as SEQ ID NO:19 was designed for optimal expression in cotton. The plant expression cassette shown as SEQ ID NO:19 was designed for optimal expression in soybean and other Leguminous plants. Each of these sequences are evaluated for expression in plant protoplasts derived from the crop plant of interest in which control of an insect pest is desired such as cotton, for example in controlling a Hemipteran pest. A sequence designed for optimal expression in one plant type or species may also be expressed in a different plant type or species.

The DNA constructs that comprise the plant expression cassettes described above are typically maintained in various vectors. Vectors contain sequences that provide for the replication of the vector and covalently linked sequences in a host cell. For example, bacterial vectors will contain origins of replication that permit replication of the vector in one or more bacterial hosts. *Agrobacterium*-mediated plant transformation vectors typically comprise sequences that permit replication in both *E. coli* and *Agrobacterium* as well as one or more "border" sequences positioned so as to permit integration of the expression cassette into the plant chromosome. Such *Agrobacterium* vectors can be adapted for use in either *Agrobacterium tumefaciens*, *Agrobacterium rhizogenes*, *Rhizobium*, *Mesorhizobium*, or *Sinorhizobium*. Selectable markers encoding genes that confer resistance to antibiotics are also typically included in the vectors to provide for their maintenance in bacterial hosts.

VII. Insect Inhibitory Transgenic Plants and Methods for Obtaining Insect Inhibitory Transgenic Plants Methods of obtaining a transgenic plant capable of inhibiting insects are also provided by this invention. First, expression vectors suitable for expression of the TIC853 protein in various dicot and monocot plants are introduced into a plant, a plant cell or plant tissue using transformation techniques as described herein. Next a transgenic plant containing or comprising the TIC853 expression vector is obtained by regenerating that transgenic plant from the plant, plant cell or plant tissue that received the expression vector. The final step is to obtain a transgenic plant that expresses an insect inhibitory amount of the TIC853 polypeptide. Transgenic plants expressing insect inhibitory amounts of TIC853 proteins contemplated herein include, but not limited to, barley, corn, oat, rice, rye, sorghum, turf grass, sugarcane, wheat, alfalfa, banana, broccoli, bean, cabbage, canola, carrot, castor, cassava, cauliflower, celery, chickpea, citrus, clover, coconut, coffee, cotton, a cucurbit, Douglas fir, egg plant, eucalyptus, flax, garlic, grape, olive, onion, lettuce, Loblolly pine, melons, palm, pea, peanut, pepper, potato, poplar, pine, radish, sunflower, safflower, soybean, strawberry, sugar beet, sweet gum, sweet potato, switch grass, tea, tobacco, tomato, triticale, turf grass, watermelon, ornamental, shrub, nut, chickpea, pigeonpea, millets, hops, and pasture grass plants.

TIC853 expression vectors can be introduced into the chromosomes of a host plant via methods such as *Agrobacterium*-mediated transformation, *Rhizobium*-mediated transformation, *Sinorhizobium*-mediated transformation, particle-mediated transformation, DNA transfection, DNA electroporation, or "whiskers"-mediated transformation. Suitable methods for transformation of plants include any method by which DNA can be introduced into a cell, such as by electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184, etc. Aforementioned methods of introducing transgenes are well known to those skilled in the art and are described in U.S. Patent Application Publication No. 20050289673 (*Agrobacterium*-mediated transformation of corn), U.S. Pat. No. 7,002,058 (*Agrobacterium*-mediated transformation of soybean), U.S. Pat. No. 6,365,807 (particle mediated transformation of rice), and U.S. Pat. No. 5,004,863 (*Agrobacterium*-mediated transformation of cotton). Through the application of techniques such as these, the cells of virtually any plant species may be stably transformed, and these cells developed into transgenic plants. Other techniques that may be particularly useful in the context of cotton transformation are disclosed in U.S. Pat. Nos. 5,846,797, 5,159,135, 6,624,344, U.S. Patent Application Nos. 2009/0138985 and 2008/0256667; and techniques for transforming *Brassica* plants in particular are disclosed, for example, in U.S. Pat. No. 5,750,871; and techniques for transforming soybean are disclosed in for example in Zhang et al., 1999 (Plant Cell, Tissue and Organ Culture, 56, 37-46) and U.S. Pat. No. 6,384,301; techniques for transforming corn are disclosed in WO9506722; techniques for transforming sugarcane are disclosed in U.S. Patent Application Publication 2004/0123342. Methods of using bacteria such as *Rhizobium* or *Sinorhizobium* to transform plants are described in Broothaerts, et al., Nature, 2005, 433:629-33 and US Patent Application No. US2007/0271627. Methods for transforming other plants can be found in Compendium of Transgenic Crop Plants, 2009. Blackwell Publishing. It is further understood that the TIC853 expression vector can comprise cis-acting site-specific recombination sites recognized by site-specific recombinases, including Cre, Flp, Gin, Pin, Sre, pinD, Int-B13, and R. Methods of integrating DNA molecules at specific locations in the genomes of transgenic plants through use of site-specific recombinases can then be used (U.S. Pat. No. 7,102,055). Those skilled in the art will further appreciate that any of these gene transfer techniques can be used to introduce the expression vector into the chromosome of a plant cell, a plant tissue or a plant.

The use of plant transformation vectors comprising two separate T-DNA molecules, one T-DNA containing the gene or genes of interest (i.e., one or more insect inhibitory genes of interest) and another T-DNA containing a selectable and/or scoreable marker gene are also contemplated. In these two T-DNA vectors, the plant expression cassette or cassettes comprising the gene or genes of interest are contained within one set of T-DNA border sequences and the plant expression cassette or cassettes comprising the selectable and/or scoreable marker genes are contained within another set of T-DNA border sequences. In preferred embodiments, the T-DNA border sequences flanking the plant expression cassettes comprise both a left and a right T-DNA border sequence that are operably oriented to provide for transfer and integration of the plant expression cassettes into the plant genome. When used with a suitable *Agrobacterium* host in *Agrobacterium*-mediated plant transformation, the two T-DNA vector provides for integration of one T-DNA molecule containing the gene or genes of interest at one chromosomal location and integration of the other T-DNA containing the selectable and/or scoreable marker into another chromosomal location. Transgenic plants containing both the gene(s) of interest and the selectable and/or scoreable marker genes are first obtained by selection and/or scoring for the marker gene(s) and screened for expression of the genes of interest. Distinct lines of transgenic plants containing both the marker gene(s) and gene(s) of interest are subsequently outcrossed to obtain a population of progeny transgenic plants segregating for both the marker gene(s) and gene(s) of interest. Progeny plants containing only the gene(s) of interest can be identified by any combination of DNA, RNA or protein analysis techniques. Methods for using two T-DNA vectors have been described in U.S. Pat. No. 6,265,638, U.S. Pat. No. 5,731,179, U.S. Patent Application Publication No. 2003/110532A1, and U.S. Patent Application Publication No. 2005/0183170A1.

Methods of introducing plant minichromosomes comprising plant centromeres that provide for the maintenance of the recombinant minichromosome in a transgenic plant can also be used in practicing this invention (U.S. Pat. No. 6,972,197). In these embodiments of the invention, the transgenic plants harbor the minichromosomes as extrachromosomal elements that are not integrated into the chromosomes of the host plant.

Transgenic plants are typically obtained by linking the gene of interest (i.e., in this case a TIC853 expression cassette) to a selectable marker gene, introducing the linked transgenes into a plant cell, a plant tissue or a plant by any one of the methods described above, and regenerating or otherwise recovering the transgenic plant under conditions requiring expression of said selectable marker gene for plant growth. The selectable marker gene can be a gene encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, dicamba monooxygnese protein, and an aminoethylcysteine insensitive octopine synthase protein. The corresponding selective agents used in conjunction with each gene can be: neomycin (for neomycin phosphotransferase protein selection), phosphinotricin (for phosphinothricin acetyltransferase protein selection), glyphosate (for glyphosate resistant 5-enol-pyruvylshikimate-3-phosphate synthase (EPSPS) protein selection), hygromycin (for hygromycin phosphotransferase protein selection), sulfadiazine (for a dihydropteroate synthase protein selection), chlorsulfuron (for a sulfonylurea insensitive acetolactate synthase protein selection), atrazine (for an atrazine insensitive Q protein selection), bromoxinyl (for a nitrilase protein selection), dalapon (for a dehalogenase protein selection), 2,4-dichlorophenoxyacetic acid (for a 2,4-dichlorophenoxyacetate monoxygenase protein selection), methotrexate (for a methotrexate insensitive dihydrofolate reductase protein selection), dicamba (for dicamba monooxygnese protein selection), or aminoethylcysteine (for an aminoethylcysteine insensitive octopine synthase protein selection).

Transgenic plants can also be obtained by linking a gene of interest (i.e., in this case an TIC853 expression cassette) to a scoreable marker gene, introducing the linked transgenes into a plant cell by any one of the methods described above, and regenerating the transgenic plants from transformed plant cells that test positive for expression of the scoreable marker gene. The scoreable marker gene can be a gene encoding a beta-glucuronidase protein, a green fluorescent protein, a yellow fluorescent protein, a red fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein or a chloramphenicol acetyl transferase protein.

When the expression vector is introduced into a plant cell or plant tissue, the transformed cells or tissues are typically regenerated into whole plants by culturing these cells or tissues under conditions that promote the formation of a whole plant (i.e., the process of regenerating leaves, stems, roots, and, in certain plants, reproductive tissues). The development or regeneration of transgenic plants from either single plant protoplasts or various explants is well known in the art (Horsch, R. B. et al., 1985, Science, 227, 1229-1231). This regeneration and growth process typically includes the steps of selection of transformed cells and culturing selected cells under conditions that will yield rooted plantlets. The resulting transgenic rooted shoots are thereafter planted in an appropriate plant growth medium such as soil. Alternatively, transgenes can also be introduced into isolated plant shoot meristems and plants regenerated without going through callus stage tissue culture (U.S. Pat. No. 7,002,058). When the transgene is introduced directly into a plant, or more specifically into the meristematic tissue of a plant, seed can be harvested from the plant and selected or scored for presence of the transgene. In the case of transgenic plant species that reproduce sexually, seeds can be collected from plants that have been "selfed" (self-pollinated) or outcrossed (i.e., used as a pollen donor or recipient) to establish and maintain the transgenic plant line. Transgenic plants that do not sexually reproduce can be vegetatively propagated to establish and maintain the transgenic plant line. As used here, transgenic plant line refers to transgenic plants derived from a transformation event where the transgene has inserted into one or more locations in the plant genome. In a related aspect, the present invention also encompasses a seed produced by the transformed plant, a progeny from such seed, and a seed produced by the progeny of the original transgenic plant, produced in accordance with the above process. Such progeny and seeds will have a TIC853 protein-encoding transgene stably incorporated into their genome, and such progeny plants can inherit the traits in Mendelian fashion. All such transgenic plants having incorporated into their genome transgenic DNA segments encoding one or more TIC853 proteins or polypeptides are aspects of this invention. It is further recognized that transgenic plants containing the DNA constructs described herein, and materials derived therefrom, may be identified through use of PCR or other methods that can specifically detect the sequences in the DNA constructs.

Once a transgenic plant is regenerated or recovered, a variety of methods can be used to identify or obtain a transgenic plant that expresses a insect inhibitory amount of TIC853. One general set of methods is to perform assays that measure the amount of TIC853 that is produced. For example, various antibody-based detection methods employing antibodies that recognize TIC853 can be used to quantitate the amount of TIC853 produced. Examples of such antibody based assays include, but are not limited to, ELISAs, RIAs, or other methods wherein a TIC853-recognizing antibody is detectably labelled with an enzyme, an isotope, a fluorophore, a lanthanide, and the like. By using purified or isolated TIC853 protein as a reference standard in such assays (i.e., providing known amounts of TIC853), the amount of TIC853 present in the plant tissue in a mole per gram of plant material or mass per gram of plant material can be determined. The TIC853 protein will typically be expressed in the transgenic plant at the level of "parts per million" or "ppm" where microgram levels of TIC853 protein are present in gram amounts of fresh weight plant tissue. In this case, 1 microgram of TIC853 protein per 1 gram of fresh weight plant tissue would represent a TIC853 concentration of 1 ppm. An insect inhibitory amount of TIC853 protein is at least 5 ppm (i.e., 5 µg TIC853 protein per gram fresh weight plant tissue). In preferred embodiments, an insect inhibitory amount of TIC853 protein is at least 50 ppm (i.e., 50 µg TIC853 protein per gram fresh weight plant tissue). In more preferred embodiments, the amount of TIC853 is at least 250 ppm (i.e. 50 µg TIC853 protein per gram fresh weight plant tissue).

Alternatively, the amount of TIC853 mRNA produced by the transgenic plant can be determined to identify plants that express insect inhibitory amounts of TIC853 protein. Techniques for relating the amount of protein produced to the amount of RNA produced are well known to those skilled in the art and include methods such as constructing a standard curve that relates specific RNA levels (i.e., TIC853 mRNA) to levels of the TIC853 protein (determined by immunologic or other methods). Methods of quantitating TIC853 mRNA typically involve specific hybridization of a polynucleotide to either the TIC853 mRNA or to a cDNA (complementary DNA) or PCR product derived from the TIC853 RNA. Such polynucleotide probes can be derived from either the sense and/or antisense strand nucleotide sequences of the TIC853 protein-encoding transgene. Hybridization of a polynucleotide probe to the TIC853 mRNA or cDNA can be detected by methods including, but not limited to, use of probes labelled with an isotope, a fluorophore, a lanthanide, or a hapten such as biotin or digoxigenin. Hybridization of the labelled probe may be detected when the TIC853 RNA is in solution or immobilized on a solid support such as a membrane. When quantitating TIC853 RNA by use of a quantitative reverse-transcriptase Polymerase Chain Reaction (qRT-PCR), the TIC853-derived PCR product can be detected by use of any of the aforementioned labelled polynucleotide probes, by use of an intercalating dye such as ethidium bromide or SYBR green, or use of a hybridization probe containing a fluorophore and a quencher such that emission from the fluorophore is only detected when the fluorophore is released by the 5' nuclease activity of the polymerase used in the PCR reaction (i.e., a TaqMan™ reaction; Applied Biosystems, Foster City, Calif.) or when the fluorophore and quencher are displaced by polymerase mediated synthesis of the complementary strand (i.e., Scorpion™ or Molecular Beacon™ probes). Various methods for conducting qRT-PCR analysis to quantitate mRNA levels are well characterized (Bustin, *Journal of Molecular Endocrinology* 29: 23-39, 2002). Fluorescent probes that are activated by the action of enzymes that recognize mismatched nucleic acid complexes (i.e., Invader™, Third Wave, Technologies, Madison, Wis.) can also be used to quantitate RNA. Those skilled in the art will also understand that RNA quantitation techniques such as Quantitative Nucleic Acid Sequence Based Amplification (Q-NASBA™) can be used to quantitate TIC853 protein-encoding mRNA and identify expressing plants.

Transgenic plants that express insect inhibitory amounts of TIC853 can also be identified by directly assaying such plants for insect inhibition. Since *Lygus* is a phytophagous, piercing-sucking insect, in planta expression and testing of toxin proteins must be presented in a manner that will permit feeding by the insect from the plant and its associated tissues. Several factors are critical in selecting a plant species for transformation that will allow for testing of the toxin proteins. The plant must be easily transformable and the tissue derived from the plant must be of the type that is preferred by the insect pest. For this purpose, it is preferable to use a plant that has leaves or other organs that have a large enough surface area to attach a barrier that inhibits the mobility of the insect pest and forces the organism to feed from the plant organ. In addition, the vascular tissue of the plant organ must be close enough to the surface of the organ to allow for the insect pest to probe, penetrate and subsequently feed. It is also preferable that the plant used in transformation be of the type that can easily be induced to develop from undifferentiated callus.

Insect pests such as *Lygus*, when feeding on a cotton plant, typically feed primarily at the flower buds or bolls. Cotton transformation is well known in the art; however the time it takes to go from transformation of plant cells to a fully developed cotton plant is too long to be practical for screening purposes. Therefore, undifferentiated cotton callus tissue would be the preferred initial transgenic plant testing material when studying *Lygus* feeding on cotton cells transformed with TIC853 proteins. Cotton cells are transformed with constructs containing the TIC853 protein encoding gene. Callus tissue is allowed to develop in tissue culture after transformation in a Petri dish. The *Lygus* nymphs are then placed into the Petri dish containing the callus. The secured lid of the Petri dish prevents the escape of the *Lygus* nymphs. Any material that will prevent *Lygus* escape but allow gas exchange in the Petri dish, for example, Parafilm® can be used to secure the Petri dish lid. A percentage of *Lygus* nymphs will find the callus tissue and feed. Scores for mortality and stunting are then calculated taking into account the background death that will occur from those insects which fail to feed on the callus tissue. *Lygus* nymphs would also be presented with control callus tissue that is not transformed with a TIC853 encoding gene as a control for normal nymph growth on callus tissue.

An alternate tissue for TIC853 protein mediated inhibition is leaf tissue. Any plant that possesses leaf tissue with a surface area sufficient to place a barrier preventing *Lygus* escape could be used. For example, alfalfa, corn, soybean or lettuce cells can be transformed with constructs containing the toxin protein encoding gene or genes of interest that have been optimized for monocot or dicot expression. The transformed cells are allowed to develop into callus tissue and then subsequently regenerated into plants. Insect pests such as *Lygus* nymphs are then allowed to feed when the plant has reached a sufficient level of maturity, such as when the leaves have grown to a size permitting the use of a physical barrier to prevent *Lygus* escape. The barrier to prevent escape of the *Lygus* nymphs can be any commercially available or home made device that permits contact of the *Lygus* nymphs with the leaf tissue and allows the insect to probe and feed from the vascular tissue of the leaf. Clip cages similar to those described by Mowry (1993) (J. Agric. Entomol. 10:181-184) would be sufficient to contain the *Lygus* nymphs for feeding. Mortality and stunting scores are then determined with respect to the background death that will occur from those insects which fail to feed on the leaf tissue. *Lygus* nymphs would also be presented with control leaf that is not transformed with a TIC853 encoding gene as a control for normal nymph growth on callus tissue.

The in planta insect inhibition assays can be used to identify transgenic plants that inhibit any of the large variety of insect pests that pierce and/or suck the fluids from the cells and tissues of plants that must be restricted to the assay tissue. In particular, such insect inhibition assays can be used to test plants expressing TIC853 and/or other insect inhibitory agents. Other insect inhibitory agents include, but are not limited to, (i) ribonucleotide sequences that functions upon ingestion by said insect pest to inhibit a biological function within said insect and (ii) non-TIC853 proteins that are insect inhibitory. The insect pests include those insect pests that pierce and then suck the phloem sap or cell contents as well as those that macerate the cells in the vicinity of the feeding zone and then take up the fluid that is released from the macerated cells through there proboscis. Insects targeted by the TIC853 proteins and other insect inhibitory agents described herein include various Hemipteran, Homopteran, and Heteropteran insects. Inhibition of insects such as *Lygus*, whiteflies, hoppers and aphids is specifically contemplated by use of TIC853 and other insect inhibitory agents as described herein.

VIII. Transgenic Plant Insect Control Methods

Transgenic plants of the present invention comprising polynucleotides encoding TIC853 or insecticidal fragments thereof can be used in methods of controlling insect infestations. Transgenic barley, corn, oat, rice, rye, sorghum, turf grass, sugarcane, wheat, alfalfa, banana, broccoli, bean, cabbage, canola, carrot, castor, cassava, cauliflower, celery, chickpea, citrus, clover, coconut, coffee, cotton, a cucurbit, Douglas fir, egg plant, eucalyptus, flax, garlic, grape, olive, onion, lettuce, Loblolly pine, melons, palm, pea, peanut, pepper, potato, poplar, pine, radish, sunflower, safflower, soybean, strawberry, sugar beet, sweet gum, sweet potato, switch grass, tea, tobacco, tomato, triticale, turf grass, watermelon, ornamental, shrub, nut, pigeonpea, millets, hops, and pasture grass plants can be used in these methods. Transgenic plants such as alfalfa, canola, cotton, lettuce and strawberry plants that are attacked by Hemipteran insect pests inhibited by TIC853 proteins are specifically contemplated by this invention. Even more specifically contemplated by the present invention are transgenic cotton plants comprising polynucleotides encoding TIC853 or insecticidal fragments thereof that are protected from *Lygus* species insect infestation. Transgenic plants of the present invention are particularly effective for controlling species of insects that pierce and/or suck the fluids from the cells and tissues of plants, including but not limited to, plant bugs in the Miridae family such as western tarnished plant bugs (*Lygus hesperus* species), tarnished plant bugs (*Lygus lineolaris* species), and pale legume bugs (*Lygus elisus*) and stink bugs (Pentatomidae family species).

It is also contemplated that transgenic plants expressing TIC853 proteins of the invention can be used to control Coleopteran insects. Coleopteran insects controlled by TIC853 proteins of the invention include, but are not limited to, Colorado potato beetle, wire worm and boll weevil.

Although the TIC853 protein exhibits similarity to Cry51Aa1 which has been shown to have Lepidopteran activity, TIC853 protein did not exhibit significant Lepidopteran activity. TIC853 protein displayed activity against Colorado Potato Beetle.

Specific types of transgenic plants expressing TIC853 proteins that inhibit specific insect pests are contemplated by this invention. Transgenic cotton plants expressing insect inhibitory TIC853 proteins that inhibit Hemipteran insects including *Lygus*, hoppers and aphids are specifically contemplated. Transgenic cotton plants that express the TIC853 protein of SEQ ID NO:6 are anticipated to inhibit *Lygus hesperus* or *Lygus lineolaris*. Transgenic alfalfa, canola, lettuce and strawberry plants that express the TIC853 protein of SEQ ID NO:6 and that inhibit *Lygus* are also specifically contemplated.

The transgenic plants expressing insect inhibitory amounts of the insect inhibitory TIC853 proteins are first identified by any one of the methods described herein. Initial insect inhibition can be conducted in controlled environmental conditions (i.e., in enclosed growth chambers or green houses). Transgenic plants can also be subjected to insect infestation in field tests and compared against non-transgenic control plants. Typically, the non-transgenic control plants will include both plants treated with insecticides and untreated plants. Transgenic plant lines (i.e., transgenic plants derived from distinct transformation events comprising transgene insertions into different genomic locations) that display the best insect inhibitory activity are selected for potential development for use in a variety of different genetic backgrounds (i.e., genetically distinct cultivars, varieties, and/or hybrid germplasms). Methods of introgressing transgenes into distinct germplasms and producing seed lots that primarily comprise transgenic seed are known to those skilled in the art. For example, the transgene can be fixed in a homozygous state in a desired genetic background. Once the transgene is fixed in that background, the homozygous transgenic plant can be used to produce transgenic seed of non-hybrid crops. Alternatively, the homozygous transgenic plant can be used as a pollen donor or recipient to produce transgenic seed of hybrid crops.

Specific types of transgenic plants expressing insect inhibitory TIC853 proteins that inhibit specific insect pests are contemplated by this invention. Transgenic cotton plants expressing insect inhibitory TIC853 proteins that inhibit Hemipteran insects including *Lygus*, hoppers and aphids are specifically contemplated. Transgenic cotton, alfalfa, canola, and strawberry plants that express the TIC853 protein of SEQ ID NO:6 are anticipated to inhibit *Lygus hesperus* or *Lygus lineolaris* and are specifically contemplated.

IX. Non-Transgenic Control Methods and Compositions

The TIC853 protein compositions disclosed herein will find particular utility as insect inhibitory agents for topical and/or systemic application to field crops, grasses, fruits and vegetables, and ornamental plants. More specifically, insect inhibitory TIC853 proteins can be used in compositions comprising an insect inhibitory amount of an insect inhibitory TIC853 protein composition. In this regard, insect inhibitory TIC853 protein compositions made up of TIC853 crystal protein preparations for *Bacillus thuringiensis* spores are particularly useful. The TIC853 protein composition can comprise the amino acid sequence of SEQ ID NO:6 or to an insect inhibitory protein of at least 300 amino acids that displays at least 88% sequence identity to a corresponding polypeptide sequence of 300 amino acids contained within SEQ ID NO:6.

X. Commodity Products

It is also contemplated that various commodity products may be obtained with the compositions and methods of this invention. Moreover, it is specifically contemplated that one or more advantages can be associated with the commodity products derived from this invention. It is anticipated that the use of the TIC853 insect inhibitory protein and associated methods can provide for commodity products with lowered pesticide residue levels. In certain instances, growers will be prompted to use fewer pesticides such as organophosphates, carbamates, neonicotinoid, and pyrethroid insecticides. Exposure of individuals who grow, harvest, process or otherwise come into contact with the commodity products of this invention to these pesticides is thus anticipated to be reduced. Reduced use of pesticides is also anticipated to provide for reduced costs of commodity product production, reduced levels of environmental contamination and reduced undesirable side effects on beneficial (non-target) insects and fauna. It is further contemplated that the use of this invention will provide for commodity products with lower costs of production due to factors including, but not limited to, increased yield and/or decreased insecticide usage.

XI. Methods of Using TIC853 Insect Inhibitory Proteins in Combination with Other Insect Inhibitory Agents Several methods by which increased resistance to a specific insect pest or broader resistance to several classes of insect pests are contemplated by this invention. Both methods entail contacting the insect pest(s) with an insect inhibitory TIC853 protein in combination with a distinct insect inhibitory agent. This distinct insect inhibitory agent can inhibit the same Hemipteran insect pests inhibited by the insect inhibitory TIC853 protein to provide for a decreased incidence of Hemipteran insect resistance to the TIC853 protein or other Hemipteran insect inhibitory agent. Alternatively, the distinct insect inhibitory agent can inhibit an insect that is not inhibited by an otherwise insect inhibitory TIC853 protein to expand the spectrum of insect inhibition obtained.

The potential for insects to develop resistance to certain insecticides is well documented. Most insect resistance management strategies using genetically modified crops expressing insect inhibitory agents rely on the use of refuge areas that are comprised of crop plants that lack the insect inhibitory gene. In theory, the refuge provides a region in which non-resistant insect populations harboring non-resistant genetic alleles are maintained, lowering the potential for resistance to develop within the insect population. However, the refuge strategy suffers from several short-comings. First, the growers must accept reduced yields on the acreage planted with the insect inhibitory gene. Second, it is not clear that refuges will effectively control dominant resistance alleles that can arise in the insect population.

An alternative insect resistance management strategy can employ transgenic crops that express two distinct insect inhibitory agents that operate through different modes of action. In this case, any insects with resistance to either one of the insect inhibitory agents will be controlled by the other insect inhibitory agent, thus reducing the chances of resistance developing in the insect population.

In addition, a single crop may be subject to destruction by several different classes of insect pests operating at the same time in the field. For example, a cotton plant can be attacked by both Hemipteran pests, such as *Lygus*, and Lepidopteran pests such as *Spodoptera exigua* (beet armyworm), *Heliothis zea* (cotton bollworm) and/or *Helicoverpa armigera* (armyworm) in the course of a growing season. Expression of distinct inhibitory agents which are active to each of these pests would provide greater protection to the cotton plant and would increase the yield per acre due to a reduction of loss caused by the insect pests.

A first group of insect inhibitory agents that can be used in combination with an insect inhibitory TIC853 protein for insect resistance management or expanded insect inhibitory spectrum comprise ribonucleotide sequences that function upon ingestion by said insect pest to inhibit a biological function within said insect pest. Specific nucleotide sequences selected from the sequences native to the cells of a particular pest that are involved in an essential biological pathway can be expressed in a cell in such a way as to result in the formation of a double stranded RNA, or even a stabilized double stranded RNA. By inhibiting the essential gene product of the target insect pest with the ribonucleotide, the organism fails to develop and eventually dies. The use of such ribonucleotide sequences to control insect pests such as *Lygus* is described in U.S. Patent Application Publication No. 2006/0021087. Essential insect genes that provide essential biological function that include, but are not limited to, muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis are targeted for inhibition. Insect genes that can be inhibited include, but are not limited to, genes encoding a V-ATPase protein, a ubiquitin protein, a polyglacturonase protein, a pectinase protein, a GABA neurotransmitter transporter protein, a EFI alpha protein, a cytochrome P-450 mono-oxygenase protein, a cuticle protein precursor protein, a CHD3 protein, and a 20S proteasome protein. The ribonucleotide based insect control agent may also comprise sequences directed against multiple insect target genes. For control of *Lygus*, inhibitory ribonucleotides directed against SEQ ID NO:28 through SEQ ID NO:43 or combinations of inhibitory ribonucleotides directed against SEQ ID NO:28 through SEQ ID NO:43 are specifically contemplated. The use of SEQ ID NO:28 through SEQ ID NO:43 in the control of insects is disclosed in U.S. Patent Application Publication No. 2006/0021087. When multiple insect genes are targeted for suppression, a polycistronic DNA element can be fabricated as illustrated and disclosed in Fillatti, U.S. Patent Application Publication No. 2004/0029283 A1.

A variety of methods can be used to produce inhibitory ribonucleotides directed against a target pest in a transgenic plant. In general, the inhibitory dsRNA and the portion of the insect target gene share at least from about 80% sequence identity, or from about 90% sequence identity, or from about 95% sequence identity, or from about 99% sequence identity, or even about 100% sequence identity. Alternatively, the duplex region of the RNA may be defined functionally as a nucleotide sequence that is capable of hybridizing with a portion of the target gene transcript. A less than full length sequence exhibiting a greater homology compensates for a longer less homologous sequence. The length of the identical nucleotide sequences may be at least 25, 50, 100, 200, 300, 400, 500 or 1000 bases. Normally, a sequence of greater than 20-100 nucleotides should be used, though a sequence of greater than about 200-300 nucleotides would be preferred, and a sequence of greater than 500-1000 nucleotides would be especially preferred depending on the size of the target gene.

In another embodiment, the insect inhibitory ribonucleotide can be produced by an inverted repeat separated by a "spacer sequence". The spacer sequence may be a region comprising any sequence of nucleotides that facilitates secondary structure formation between each repeat, where this is required. In one embodiment of the present invention, the spacer sequence is part of the sense or antisense coding sequence for mRNA. The spacer sequence may alternatively comprise any combination of nucleotides or homologues thereof that are capable of being linked covalently to a nucleic acid molecule. The spacer sequence may comprise a sequence of nucleotides of at least about 10-100 nucleotides in length, or alternatively at least about 100-200 nucleotides in length, at least about 200-400 nucleotides in length, or at least about 400-500 nucleotides in length.

A transgene sequence for producing a dsRNA may comprise a promoter that is operatively linked to an intron encoding sequence and a hairpin RNA derived from a sequence in the target gene (Miki and Shimamoto, Plant Cell Physiol. April 2004; 45(4):490-495). Alternatively, a transgene sequence for producing an siRNA may comprise an RNA pol III promoter operably linked to a hairpin RNA (Lu et al., Nucleic Acids Res. Dec. 2, 2004; 32(21):e171). The hairpin RNA may comprise a 5' sequence of roughly 19-24 nucleotides of sense strand target gene sequence followed by a spacer nucleotide of about 8-10 nucleotides followed by a sequence of roughly 19-24 nucleotides of antisense sequence that is capable of base pairing with the preceding sense strand sequence. However, hairpin RNA-expressing plant transgenes containing sense/anti-sense arms ranging from 98 to 853 nucleotides can also be used (Wesley et al., Plant J. 2001, 27(6):581-90). Vectors and methods for transgene-mediated expression of hairpin RNAs are disclosed in U.S. Patent Application Nos. 2005/0164394, 2005/0160490, and 2004/0231016.

A second group of insect inhibitory agents that can be used in combination with a TIC853 protein for insect resistance management or expanded insect inhibitory spectrum comprise insect inhibitory proteins other than TIC853. A wide variety of insect inhibitory proteins derived from *B. thuringiensis, Photorhabdus* sp., and/or *Xenorhabdus* sp. can be used.

For the control of sucking piercing insects such as *Lygus*, several non-TIC853 insect inhibitory proteins can be combined with TIC853 expression in planta for greater control and/or resistance management. Such molecules expressed in planta along with TIC853 may include ET29, ET37, TIC809, TIC810, TIC812, TIC127, TIC128 (PCT U.S. 2006/033867), AXMI-027, AXMI-036, and AXMI-038 (WO 06/107761), AXMI-018, AXMI-020, and AXMI-021 (WO 06/083891), AXMI-010 (WO 05/038032), AXMI-003 (WO 05/021585), AXMI-008 (U.S. 2004/0250311), AXMI-006 (U.S. 2004/0216186), AXMI-007 (U.S. 2004/0210965), AXMI-009 (U.S. 2004/0210964), AXMI-014 (U.S. 2004/0197917), AXMI-004 (U.S. 2004/0197916), AXMI-028 and AXMI-029 (WO 06/119457) and AXMI-007, AXMI-008, AXMI-0080rf2, AXMI-009, AXMI-014 and AXMI-004 (WO 04/074462). Presenting the combination of the inhibitory protein molecules, TIC809 (presented as SEQ ID NO:45) and TIC810 (presented as SEQ ID NO:47) has been previously shown to be inhibitory to the Western Tarnished Plant Bug (WTPB), *Lygus hesperus* Knight in bioassay (PCT U.S. 2006/033867). The fusion proteins of TIC809 and TIC810, TIC127 (presented as SEQ ID NO:49) and TIC128 (presented as SEQ ID NO:51) may also be active against *Lygus*. The polynucleotide encoding TIC127 is comprised of the nucleic acid molecule encoding TIC809 linked to the nucleic acid molecule encoding TIC810 by a polylinker nucleotide sequence (presented as SEQ ID NO:52) encoding the amino acid linker presented as SEQ ID NO:53. The polynucleotide encoding TIC128 is comprised of the nucleic acid molecule encoding TIC810 linked to the nucleic acid molecule encoding TIC809 by a polylinker nucleotide sequence (presented as SEQ ID NO:52) encoding the amino acid linker presented as SEQ ID NO:53. Expression of TIC853 in combination with TIC127 or TIC128 may provide enhanced control of *Lygus*. Dicot plants such as cotton could be transformed with plant expression constructs containing nucleotide sequences optimized for expression in plants encoding TIC853 (presented as any of SEQ ID NOs:16, 17, 18, 19, 20, 21, 22, 23, or 24) along with TIC809 (presented as SEQ ID NO:44) and TIC810 (presented as SEQ ID NO:47), or TIC127 (presented as SEQ ID NO:48), or TIC128 (presented as SEQ ID NO:50) to provide enhanced resistance to *Lygus* or inhibition of additional species contained within the genus, *Lygus*.

For control of Lepidopteran pests, combinations of insect inhibitory TIC853 proteins with Lepidopteran-active proteins such as Cry1A proteins (U.S. Pat. No. 5,880,275), Cry1B (U.S. patent Ser. No. 10/525,318), Cry1C (U.S. Pat. No. 6,033,874), Cry1F, Cry1A/F chimeras (U.S. Pat. Nos. 7,070,982; 6,962,705; and 6,713,063), and a Cry2Ab protein (U.S. Pat. No. 7,064,249) are specifically contemplated.

DNA sequences encoding insect inhibitory TIC853 protein molecules and other insect inhibitory agents such as double stranded RNA molecules and/or non-TIC853 proteins can be combined in a single plant either through direct transformation, by breeding, or a combination thereof. Multiple transcription units comprising a promoter and an insect inhibitory agent encoding region can be introduced on the same plant transformation vector or on different plant transformation vectors. When the two insect inhibitory agents are proteins, the coding regions for each may be separated by a protease sensitive linker or even a self-processing protease cleavage site (see U.S. Pat. No. 5,846,767). When the insect inhibitory agents are each introduced into distinct transgenic plants, those plants may be crossed to obtain a plant containing all of the insect inhibitory agent encoding transgenes.

A further benefit can be obtained by using DNA sequences encoding insect inhibitory TIC853 protein molecules with activity in controlling two classes of insect pests, Hemipteran and Coleopteran pests, in conjunction with DNA sequences that encode distinct insect inhibitory agents with activity against either the same or distinct insect pests. Combinations of TIC853 with another dual active insect inhibitory agent that is also active against Hemipteran and Coleopteran insects and that has a different mode of action than TIC853, provides in the plant control of at least two classes of insect pests by dual modes of action with only two expression cassettes. Combinations of TIC853 with two insect inhibitory agents, one active against Hemipterans and the other active against Coleopterans, with each agent having a different mode of action than TIC853, provides in the plant control of at least two classes of insect pests by multiple modes of action with only three expression cassettes. Under conditions in which each insect inhibitory agent is specific to each insect class, four expression cassettes would be required to provide the same protection as above. This would increase the complexity of the transformation, breeding and selection process for a desirable plant event.

It is further anticipated that the combination of insect inhibitory TIC853 protein molecules and other insect inhibitory agents such as double stranded RNA molecules and/or non-TIC853 proteins can result in unexpected synergistic insect inhibitory effects that are not observed with either the TIC853 insecticidal protein alone, the insect inhibitory ribonucleotide alone, or the non-TIC853 insect inhibitory protein alone. Synergistic effects include but are not limited to, (i) quantitative changes in $LC_{50}$ $EC_{50}$, $IC_{50}$, percent mortality, or percent stunting values and (ii) qualitative changes in the spectrum of insect inhibition (i.e., Hemipteran, Homopteran, and Lepidopteran insects inhibition) that does not reflect the simple combination of the spectrum exhibited by each insect inhibitory agent alone (i.e., the combination of Hemipteran insect inhibition provided by one agent and Lepidopteran insect inhibition provided by another agent). A non-limiting example of a quantitative synergistic effect is a decrease in any $LC_{50}$, $EC_{50}$, and/or $IC_{50}$, value or an increase in percent mortality, or percent stunting values observed in a combination that is more than additive. A non-limiting example of a qualitative synergistic effect is control of an insect pest with the combination of insect agents that is not observed with either member alone. In this instance, the new insect pest controlled by the combination may be an insect pest within an order of insects (i.e., Hemipterans) where the insect inhibitory agents only inhibit other insect pests within that order of insects when used alone.

XII. Methods of Using TIC853 Insect Inhibitory Proteins in Combination with Seed Treatments Plants are vulnerable to pests such as insects, bacteria, and fungi during germination, sprouting and initial growth because the growing plant is small and even a small amount of pest-mediated damage can cause the loss of the entire plant. Moreover, some natural plant defenses are not fully developed at these stages of plant development, rendering the plant even more vulnerable to pests. The use of additional insect inhibitory agents as part of a seed treatment in plants expressing TIC853 can prove very useful under conditions of early high insect pressure during germination and affect insect pests not inhibited by TIC853. The seed can be treated to contain on or near its surface after planting any insect inhibitory agent such as another insect toxin protein, a dsRNA, a protein other than an insect toxin that has insect inhibitory properties, a synthetic pesticide, a semi-synthetic pesticide, or an organic pesticide. The seed treatment can contain any agent that may have a negative affect upon the growth and survival of any plant pest, including but not limited to, an insect pest, a nematode, a fungal pest, or a bacterial pest.

The control of pests by applying insecticides directly to plant seed has been described. For example, U.S. Pat. No. 6,713,077 discloses the use of seed treatments composition comprising at least one pyrethrin or synthetic pyrethroid in controlling European Corn Borer and Corn Root Worm. U.S. Pat. No. 5,696,144 discloses that the European corn borer caused less feeding damage to corn plants grown from seed treated with a 1-arylpyrazole compound at a rate of 500 g per quintal of seed than control plants grown from untreated seed. In addition, U.S. Pat. No. 5,876,739 (Turnblad et al., and its parent, U.S. Pat. No. 5,849,320) disclose a method for controlling soil-borne insects which involves treating seeds with a coating containing one or more polymeric binders and an insecticide. This reference provides a list of insecticides that it identifies as candidates for use in this coating and also names a number of potential target insects.

Formulations conventionally used for seed treatment are usually either solid or liquid. In addition, any conventional active or inert material can be used for coating seeds with an insect inhibiting agent or an agent effective against any plant pest, such as conventional film-coating materials including, but not limited to, water-based film coating materials such as Sepiret (Seppic, Inc., Fairfield, N.J.) and Opacoat (Berwind Pharm. Services, Westpoint, Pa.).

XIII. Isolated TIC853 Proteins and Biological Equivalents

Isolated TIC853 proteins are also provided herein. In one embodiment, the TIC853 proteins comprise proteins of at least 300 amino acids that have at least 88% sequence identity over a length of at least 300 amino acids of a corresponding polypeptide sequence contained within SEQ ID NO:6 and display insect inhibitory activity. In certain embodiments, the TIC853 proteins comprise proteins of at least 302 amino acids that have at least 88%, 90%, 95%, 98%, 99% or 100% sequence identity over a length of at least 302 amino acids of a corresponding polypeptide sequence contained within SEQ ID NO:6 and display insect inhibitory activity. In other embodiments, the TIC853 proteins comprise proteins of at least 305 amino acids that have at least 88%, 90%, 95%, 98%, 99% or 100% sequence identity over a length of at least 305 amino acids of a corresponding polypeptide sequence contained within SEQ ID NO:6 and display insect inhibitory activity. In still other embodiments, the TIC853 proteins comprise proteins of 306 amino acids that have at least 90%, 95%, 98%, 99% or 100% sequence identity over a length of 306 amino acids of a corresponding polypeptide sequence of SEQ ID NO:6 and display insect inhibitory activity. The biologically functional equivalent peptides, polypeptides, and proteins contemplated herein should possess about 88% or greater sequence identity, preferably about 90% or greater sequence identity, and most preferably about 95% to 99% or greater sequence identity, to the sequence of, or corresponding moiety within, the TIC853 polypeptide sequence. In certain embodiments of the invention, biologically functional equivalent peptides, polypeptides, and proteins possessing about 88% or greater sequence identity, preferably about 90% or greater sequence identity, and most preferably about 95% to 99% or greater sequence identity, to the sequence of TIC853 (SEQ ID NO:6).

We disclose and claim TIC853 and proteins which exhibit greater than 88% amino acid identity to the sequence of TIC853 (SEQ ID NO:6) that also exhibit *Lygus* activity and/or Coleopteran activity.

Peptides, polypeptides, and proteins biologically functionally equivalent to TIC853 include, but are not limited to, amino acid sequences containing conservative amino acid substitutions in the TIC853 protein sequences. An example of TIC853 proteins that can be substituted to obtain biological equivalents include, but are not limited to, the TIC853 protein sequence (SEQ ID NO:6). In such amino acid sequences, one or more amino acids in the sequence is (are) substituted with another amino acid(s), the charge and polarity of which is similar to that of the native amino acid, i.e., a conservative amino acid substitution, resulting in a silent change.

Substitutes for an amino acid within the TIC853 polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the TIC853 polypeptide sequence can be made by substituting one amino acid within one of these groups with another amino acid within the same group. Biologically functional equivalents of TIC853 can have 10 or fewer conservative amino acid changes, more preferably seven or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of TIC853.

As indicated, modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated TIC853 proteins are contemplated to be useful for increasing the insect inhibitory activity of the protein, and consequently increasing the insect inhibitory activity and/or expression of the recombinant transgene in a plant cell. The amino acid changes may be achieved by changing the codons of the DNA sequence, a process known to those of ordinary skill in the art.

For example, certain amino acids may be substituted for other amino acids in a protein structure without appreciable loss of biochemical or biological activity. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, J Mol. Biol. 157(1):105-32, 1982), incorporated herein by reference. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within .+2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Non-Conservative Substitutions in the TIC853 Polypeptides

It is further recognized that non-conservative substitutions in TIC853 polypeptide sequences can be made to obtain TIC853 polypeptides that are the functional biological equivalents of the TIC853 polypeptides disclosed herein. In these instances, the non-conservative substitutions can simply be tested for insect inhibition to identify non-conservative substitutions that provide for functional biological equivalents of a given TIC853 polypeptide.

Fragments and Variants of TIC853

While the insect inhibitory polypeptide of the present invention preferably comprise a TIC853 protein sequence, fragments and variants of this sequence possessing the same or similar insect inhibitory activity as that of this insect inhibitory protein are also encompassed by the present invention. Thus contiguous sequences of at least 250 or more amino acids in a TIC853 protein with insect inhibitory activity are anticipated by this invention. Fragments or variants of a TIC853 protein with insect inhibitory activity that are anticipated by this invention can also comprise amino acid substitutions, deletions, insertions or additions in an TIC853 protein sequence.

Although insect inhibitory polypeptide of the present invention preferably comprises the TIC853 protein sequence (SEQ ID NO:6) fragments and variants of this sequence possessing the same or similar insect inhibitory activity as that of this particular TIC853 protein are also encompassed by the present invention. Thus contiguous sequences of at least 250 or more amino acids in SEQ ID NO:6 with insect inhibitory activity are anticipated by this invention. The insect inhibitory TIC853 fragments can also comprise fragments with at least 260, at least 270, at least 280, at least 290, at least 300, at least 302, or at least 305 amino acid residues of the 306 amino acid TIC853 sequence of SEQ ID NO:6. The fragments or variants with insect inhibitory activity that are anticipated by this invention can also comprise amino acid substitutions, deletions, insertions or additions of the sequence shown in SEQ ID NO:6.

Fragments of the mature TIC853 protein can be truncated forms wherein one or more amino acids are deleted from the N-terminal end, C-terminal end, the middle of the protein, or combinations thereof with insect inhibitory activity are also anticipated by this invention. These fragments can be naturally occurring or synthetic mutants of TIC853, and retain the insect inhibitory activity of TIC853. A preferred TIC853 protein that can be used to obtain truncated derivatives with insect inhibitory activity is the TIC853 protein of SEQ ID NO:6. Truncated N-terminal deletion mutations of SEQ ID NO:6 include, but are not limited to, TIC853 proteins that lack 1 to 6 N-terminal amino acid residues of SEQ ID NO:6. Truncated C-terminal deletion mutations of SEQ ID NO:6 include, but are not limited to, TIC853 proteins that lack 1 to 6 C-terminal amino acid residues. In other embodiments, TIC853 proteins comprising both a N-terminal truncation of 1 to 6 amino terminal residues of SEQ ID NO:6 and a C-terminal truncation of 1 to 6 carboxy terminal residues of SEQ ID NO:6 are provided.

Variants of TIC853 include forms wherein one or more amino acids has (have) been inserted into the natural sequence. These variants can also be naturally occurring or synthetic mutants of TIC853, and retain the insect inhibitory activity of TIC853.

Combinations of the foregoing, i.e., forms of the insect inhibitory polypeptide containing both amino acid deletions and additions, are also encompassed by the present invention. Amino acid substitutions can also be present therein as well.

The fragments and variants of a TIC853 protein encompassed by the present invention should preferably possess about 88% or greater sequence identity, more preferably about 90%, 95%, 97%, 98%, or greater sequence identity, and most preferably about 99% to 100% amino acid sequence identity, to the corresponding regions of the mature TIC853 protein having the corresponding amino acid sequences shown in SEQ ID NO:6.

Use of Structure Function Relationships to Design Insect Inhibitory TIC853 Variants This invention also contemplates the use of structure function relationships to design additional insect inhibitory TIC853 protein variants. It is first contemplated that a structure could be obtained by crystallographic analysis of TIC853 crystals. Such structures are anticipated to reveal domains of the TIC853 protein involved in insect receptor binding, pore formation in the insect gut, multimerization with TIC853, protease sensitivity and/or protease resistance that contribute to the insect inhibitory activity of TIC853.

In this regard, it is also noted that TIC853 has some similarity to a family of MTX-like proteins. This Mtx-like family of proteins is named after the *Bacillus sphericus* proteins Mtx2 (Thanabalu and Porter, Gene. 170(1):85, 1996; NCBI Accession No. 2211294A) and Mtx3 (Liu et al., Appl Environ Microbiol. 62(6):2174, 1996; NCBI Accession No. AAB36661) and includes Cry15Aa1 (SEQ ID NO:55), Cry33Aa (NCBI Accession No. AAL26871), Cry23Aa (NCBI Accession No. AAF76375), Cry38Aa (NCBI Accession No. AAK64559), CryC35 (NCBI Accession No. CAA63374), the 40 KD protein (NCBI Accession No. AAA22332), and CryNT32 (NCBI Accession No. AAL26870). It is also believed that TIC853 is distantly related to the aerolysin family of proteins that include cryET33 (WO 97/17600), and TIC901 (U.S. Patent Application No. 2006/0191034). Aerolysins are a group of proteins that multimerize and form pores in membranes and are known toxins (Parker et al., Mol. Microbiol. 19(2):205, 1996). In particular, crystallographic structure determinations indicate that beta-sheet domains of aerolysins are involved in forming membrane pores (Rossjohn et al., J Struct Biol. 121(2):92, 1998). Domains of TIC853 proteins could be swapped with similar domains from other MTX-like or Aerolysin family proteins to identify domains involved in insect receptor binding, pore formation in the insect gut, multimerization with TIC853, protease sensitivity and/or protease resistance that contribute to the insect inhibitory activity of TIC853. Data from the domain swapping experiments can be compared and otherwise extrapolated to structural data for Mtx-like protein family members to elucidate domains that provide for different insecticidal activities, improved insecticidal activities, improved binding characteristics, improved pore forming capabilities.

Having identified certain protein domains of the TIC853 proteins that provide for insect inhibitory properties of the TIC853 protein (i.e., insect receptor binding, pore formation in the insect gut, multimerization with TIC853, protease sensitivity and/or protease resistance), it is further anticipated that these regions can be more extensively mutagenized. Once mutagenized, variant TIC853 proteins can be subjected to either biochemical (i.e., insect receptor binding, pore formation in the insect gut, multimerization with TIC853, protease sensitivity and/or protease resistance) or biological assays (i.e., insect inhibition assays) to identify those variants that confer improved biochemical and/or insect inhibitory activities. Additional iterative rounds of mutagenesis and assay of those identified variants is also contemplated. Various procedures for the molecular evolution of isolated proteins that are either known to those skilled in the art (Stemmer, W., Proc. Natl. Acad. Sci. USA 91: 10747, 1994; Yuan et al., Microbiol. Mol. Biol. Rev. 69(3): 373, 2005) or are provided by other entirely distinct methods can be employed to generate the TIC853 protein variants.

Isolated TIC853 Proteins of at Least 9 Amino Acids

In other embodiments of this invention, isolated proteins that comprise a polypeptide sequence of at least 9 amino acids in length that is contained within SEQ ID NO:6 that are not identical to a corresponding polypeptide sequence of at least 9 contiguous amino acids in length that is contained in TIC807 (SEQ ID NO:11) or Cry51Aa1 (SEQ ID NO:15) are provided. Isolated TIC853 proteins can also comprise peptide sequences of at least 12, 16, 32, 50, 100, 150, 200, 250 amino acids in length or less than 300 amino acids in length contained in SEQ ID NO:6 that are not identical to a corresponding polypeptide sequence of contiguous amino acids of equal length that is contained in TIC807 (SEQ ID NO:11) or Cry51Aa1 (SEQ ID NO:15). In certain embodiments, the isolated TIC853 proteins are less than 85%, 88%, 90%, or 95% identical to a corresponding polypeptide sequence contained in SEQ ID NO:11 or SEQ ID NO:15. In still other embodiments, the TIC853 proteins comprise one or more non-conserved amino acid residues selected from the group consisting of Y28, A125, S147, V213, R214, R216, E231, A265, and combinations thereof, where the indicated amino acid residues are found in a corresponding position of SEQ ID NO:6. Isolated TIC853 amino acids can be produced by methods, including, but not limited to, chemical synthetic methods or biological synthetic methods. Thus, polynucleotides encoding the aforementioned isolated TIC853 proteins are also provided herein.

At least two distinct uses for TIC853 peptide sequences of at least 9 amino acids but less than 300 amino acids in length are contemplated.

First, it is contemplated that TIC853 peptide sequences of at least 9 amino acids can be substituted into distinct protein sequences to confer all or a subset of the insect inhibitory activities of a TIC853 protein on the resultant TIC853-peptide substituted protein. Insect inhibitory activities conferred by the TIC853 peptide sequences can comprise inhibition of a Hemipteran pest including, but not limited to, *Lygus*. Without being limited by theory, it is believed that TIC853 peptide sequences of at least 9 amino acids can provide: (1) improved crystal formation, (2) improved protein stability or reduced protease degradation, (3) improved insect membrane receptor recognition and binding, (4) improved oligomerization or channel formation in the insect midgut endothelium, and (5) improved insecticidal activity or insecticidal specificity due to any or all of the reasons stated above when inserted into another protein. Larger TIC853 peptide sequences of at least 12, at least 16, at least 32, at least 50, at least 100, at least 150, at least 200, at least 250, or less than 300 amino acid residues from SEQ ID NO:6 can also be substituted into distinct protein sequences to obtain insect inhibitory TIC853-peptide substituted proteins.

TIC853-peptide substituted protein can be synthesized by techniques including, but not limited to, site-specific mutagenesis (Kunkel, T. A. et al., Meth. Enzymol. 154: 367, 1987), DNA shuffling, thermal amplification mediated extension and or overlap methods, any of the protein molecular evolution methods (Yuan et al., Microbiol. Mol. Biol. Rev. 69(3):373, 2005), direct synthesis, combinations of these methods, or by other entirely distinct methods that provide for TIC853-peptide substituted proteins. In particular, TIC853-substituted proteins derived by insertion or substitution of TIC853 peptide sequences of at least 9 amino acids into insect inhibitory proteins derived from *Bacillus thuringiensis* are contemplated. Exemplary *Bacillus thuringiensis* proteins that can be substituted with TIC853 polypeptides to obtain TIC853-substituted proteins with insect inhibitory activity include, but are not limited to, Cry15Aa1 (Brown & Whiteley, 1992, J Bacteriol 174 549-557; SEQ ID NO:55), CryET29 (U.S. Pat. No. 6,093,695), Cyt1Ba1 (U.S. Pat. No. 5,723,440), *Bacillus thuringiensis israelensis* Cyt toxins (U.S. Pat. No. 5,885,963), and distinct *Lygus* active *Bacillus thuringiensis* crystal proteins AXMI-027, AXMI-036 and AXMI-038 disclosed in U.S. Patent Application Publication No. 2006/0242732. Other proteins that can be substituted with TIC853 polypeptides to obtain TIC853-substituted proteins with insect inhibitory activity include, but are not limited to, the Mtx2 (Thanabalu and Porter, Gene. 170(1):85, 1996; NCBI Accession No. 2211294A), Mtx3 (Liu et al., Appl Environ Microbiol. 62(6):2174, 1996; NCBI Accession No. AAB36661), Cry15Aa (SEQ ID NO:55), Cry33Aa (NCBI Accession No. AAL26871), Cry23Aa (NCBI Accession No. AAF76375), Cry38Aa (NCBI Accession No. AAK64559), CryC35 (NCBI Accession No. CAA63374), the 40 KD protein (NCBI Accession No. AAA22332), CryNT32 (NCBI Accession No. AAL26870), cryET33 (WO 97/17600), Cry51Aa1 (SEQ ID NO:15), TIC807 (SEQ ID NO:11), and TIC901 (U.S. Patent Application Publication No. 2006/0191034).

It is also contemplated that isolated TIC853 proteins of comprising polypeptide sequences of about 300 to about 306 amino acids in length of a corresponding polypeptide sequence of at least 88% identity to SEQ ID NO:6 can also be used for antibody production or insect inhibition. These isolated TIC853 polypeptide sequences of the invention have at least about 90%, at least about 95%, at least about 98%, at least about 99% or 100% sequence identity to a corresponding polypeptide sequence contained within SEQ ID NO:6. These TIC853 proteins can further comprise a covalently linked indicator reagent, an amino acid spacer, an amino acid linker, a signal sequence, a chloroplast transit peptide sequence, a vacuolar targeting sequence, or a stop transfer sequence. In still other embodiments, the insect inhibitory TIC853 proteins comprise one or more amino acid residues selected from the group consisting of Y28, A125, S147, V213, R214, R216, E231, A265, and combinations thereof, where the indicated amino acid residues are found in a corresponding position of SEQ ID NO:6.

It is also contemplated that isolated TIC853 peptide sequences of at least 9 contiguous amino acids of SEQ ID NO:6 that are not identical to a polypeptide sequence of at least 9 contiguous amino acids in length that is contained in TIC807 (SEQ ID NO:11) or Cry51Aa1 (SEQ ID NO:15) can be used as immunogens or epitopes to prepare antibodies that specifically bind TIC853 proteins. Antibodies that specifically recognize a TIC853 protein are antibodies that will not bind to a polypeptide of SEQ ID NO:11, SEQ ID NO:15, or a peptide epitope derived from SEQ ID NO:11 or SEQ ID NO:15. Such antibodies are useful for detecting TIC853 proteins in transgenic plants, in commodity products derived from transgenic plants, in microorganisms or in recombinant DNA expression libraries that contain cloned TIC853 sequences. The TIC853 polypeptides can be at least 9, at least 12, at least 16, or at least 32 amino acids in length. When the TIC853 peptide sequence is at least 32 amino acids in length it has at least 88%, 90%, 95%, 98%, or 99% sequence identity to a corresponding polypeptide sequence contained within SEQ ID NO:6. The peptides can be linked to a carrier protein such as KLH or albumin to facilitate antibody production. These TIC853 proteins can also further comprise a covalently linked indicator reagent, an amino acid spacer, an amino acid linker, a signal sequence, a chloroplast transit peptide sequence, a vacuolar targeting sequence, or a stop transfer sequence.

The identification of TIC853 protein immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, U.S. Pat. No. 4,554,101).

The amino acid sequence of these "epitopic core sequences" may then be readily incorporated into peptides, either through the application of peptide synthesis or recombinant DNA technology.

Preferred TIC853 peptides for use in accordance with the present invention will generally be on the order of about 9 to about 20 amino acids in length, and more preferably about 9 to about 15 amino acids in length. It is proposed that shorter antigenic TIC853 protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to TIC853 proteins, and in particular to TIC853-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the TIC853 protein-directed antibodies disclosed herein. Additionally or alternatively, an epitopic core sequence is one that will elicit antibodies that are cross-reactive with antibodies directed against the peptide compositions of the present invention. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 9 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

XIV. TIC853 Antibody Compositions and Methods of Making Antibodies

In particular embodiments, the inventors contemplate the use of antibodies, either monoclonal or polyclonal which bind to the TIC853 proteins disclosed herein. Means for preparing and characterizing antibodies are well known in the art (see, e.g., Using Antibodies: A Laboratory Manual, Cold Spring Harbor Laboratory, 1999).

As is well known in the art, a given composition may vary in its immunogenicity. It is often necessary therefore to boost the host immune system, as may be achieved by coupling a peptide or protein immunogen to a carrier.

As is also well known in the art, the immunogenicity of a particular immunogen composition can be enhanced by the use of non-specific stimulators of the immune response, known as adjuvants.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

Monoclonal antibodies (mAbs) may be readily prepared through use of well-known techniques, such as those exemplified in U.S. Pat. No. 4,196,265, incorporated herein by reference.

Also contemplated are methods of genetic immunization to obtain either monoclonal or polyclonal antibodies which bind to the TIC853 proteins disclosed herein. In these methods, the gene encoding the TIC853 protein is operably linked to a promoter that is active in mammalian cells. Isolated plasmid DNA comprising the mammalian cell expression cassette comprising the TIC853 encoding protein is then directly injected into the animal to elicit an immune response to the encoded TIC853 protein. Animals that can be used as injection hosts for genetic immunization include, but are not limited to, mice, rats, rabbits, goats, cows, or horses. Although a variety of injection regimens can be used, one exemplary regimen would comprise injection of plasmid DNA dissolved in phosphate-buffered saline or other suitable buffer at a concentration of approximately 1-2 mg plasmid DNA/ml and at a dose of about 100 ug/injection/animal (i.e., for a mouse, rat or rabbit). About 3-4 injections can be made in each animal in two week intervals. Genetic immunization is described in Chambers and Johnston, Nature Biotechnol. (21): 1088, 2003. Contract research organizations also conduct genetic immunization experiments to obtain antibodies (QED Bioscience Inc., San Diego, Calif., USA).

Examples of useful mammalian expression cassettes that can be used for genetic immunization include, but are not limited to, the pcDNA3.1 vector (Invitrogen, Carlsbad, Calif., USA) that provides a CMV promoter for expression of operably linked genes or the pRc/RSV vector (Invitrogen, Carlsbad, Calif., USA). In cases where high levels of antigen expression is cytotoxic, a weaker promoter, such as the SV40 promoter, can be used to express the antigen. It is anticipated that either the native TIC853 gene (SEQ ID NO:5) or the synthetic TIC853 genes (SEQ ID NOs:7, 16, 17, 18, or 19) can be operably linked to promoters and polyadenylation elements that are active in mammalian cells to obtain plasmids suitable for genetic immunization. However, the design and synthesis of other TIC853 encoding sequences for expression in mammalian hosts by backtranslation of the TIC853 amino acid sequence (SEQ ID NO:6) is also contemplated. Mammalian expression vectors that further comprise signal peptide sequences that provide for extracellular secretion and/or transmembrane insertion of operably linked sequences encoding TIC853 proteins are also contemplated.

XV. TIC853 Protein Screening and Detection Kits

The present invention contemplates methods and kits for screening samples suspected of containing TIC853 proteins or TIC853 protein-related polypeptides, or cells producing such polypeptides. In the particular embodiments contemplated herein, the methods and kits detect the TIC853 protein. A kit may contain one or more antibodies of the present invention, and may also contain reagent(s) for detecting an interaction between a sample and an antibody of the present invention. In certain embodiments, the kits comprise antibodies that specifically bind TIC853 proteins. Antibodies that specifically recognize a TIC853 protein are antibodies that will not bind to a polypeptide of SEQ ID NO:11, SEQ ID NO:15, or a peptide epitope derived from SEQ ID NO:11, SEQ ID NO:15. The provided reagent(s) can be radio-, spectrophotometrically-, fluorescently- or enzymatically-labeled. The provided reagents may include a substrate that is converted to a product that can be detected by spectrophotometry, luminometry, or fluorescence. The kit can contain a known radiolabeled or hapten-labeled agent capable of binding or interacting with an antibody of the present invention.

The reagent(s) of the kit may be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, which may be provided.

In still further embodiments, the present invention concerns immunodetection methods and associated kits. It is proposed that the TIC853 proteins or peptides of the present invention may be employed to detect antibodies having reactivity therewith, or, alternatively, antibodies prepared in accordance with the present invention, may be employed to detect TIC853 proteins or TIC853 protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a TIC853 protein or peptide or a TIC853 protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of TIC853 proteins or related peptides and/or antibodies in a sample. Samples may include cells, cell supernatants, cell suspensions, cell extracts, enzyme fractions, protein extracts, or other cell-free compositions suspected of containing TIC853 proteins or peptides. Generally speaking, kits in accordance with the present invention will include a suitable TIC853 protein, peptide or an antibody directed against such a protein or peptide, together with an immunodetection reagent for detecting antibody/antigen complexes, instructions for the use of these materials, and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

Example 1

Isolation of TIC852 and TIC853 Genes

This example describes the isolation of genes that encode TIC852 and TIC853 crystal proteins derived from a strain of *Bacillus thuringiensis* (Bt). Primers for PCR amplification were designed based upon the native coding sequence for TIC807 (SEQ ID NO:10). TIC807 has been described in U.S. patent application Ser. No. 12/109,122 filed Apr. 28, 2008. The 5' end primer, pr718 (presented as SEQ ID NO:12) and 3' end primer, pr720 (presented as SEQ ID NO:13) were used to screen a collection of Bt strains using PCR amplification. To prepare pooled genomic DNAs from the strain collection, Bt strains were inoculated individually into 150 microliters of Terrific broth in a 96 well plate format. The plates were sealed with AirPore tape sheets (Qiagen, Inc., Valencia, Calif.) to enable air exchange and incubated overnight at approximately 30 degrees Celsius with moderate shaking. After overnight growth, 60 microliters of sterile 45% glycerol were added to each well to make stock plates for freezing at −80 degrees Celsius. A 10 microliter sample was extracted from each well of a 96 well stock plate and combined into a single culture tube. Three milliliters of LB media were added to the culture tube and the pooled sample (one for each 96 well plate) was grown for 4 hours at 28 degrees Celsius with shaking. After culturing, the cells were removed by centrifugation and DNA was prepared using methods known to those of ordinary skill in the art. The pooled DNA samples from each 96 well plate were arrayed in a 96 well plate. Amplification was performed using primers pr718 and pr720 and the pooled DNA samples. Amplicons produced by PCR were size fractionated on an agarose gel and compared to a control TIC807 amplicon along with a commercially prepared size standard marker. The PCR screen identified 27 pools in which an amplicon was produced. The amplicons were cloned into a pCR®2.1-TOPO® vector (Invitrogen, Carlsbad, Calif.). Six TOPO® clones from each of 15 PCR positive pools were obtained. The plasmids were prepared from each sample and the amplicons contained in each plasmid sequenced. One amplicon encoded what appeared to be a homolog to TIC807. The strain from which this product was acquired was identified by performing a PCR screen of the corresponding 96 well plate from which the positive pool was obtained. One strain, designated EG5122, produced an amplicon encoding a homolog of TIC807. The resulting amplicon, designated as TIC852 and presented as SEQ ID NO:1, encodes a protein (SEQ ID NO:2) which is approximately 83% identical to the TIC807 protein sequence.

The TIC852 amplicon was cloned into the Bt expression vector, pMON101647 using the In-Fusion cloning kit (Clontech Laboratories, Inc., Mountain View, Calif.) and transformed into *E. coli*. After sequence confirmation of the cloned insert, the vector was transformed into a Cry-Bt host strain, EG10650. The transformed Bt was grown in C2 medium to prepare TIC852 protein for insect testing.

Inverse PCR was performed on DNA extracted from strain EG5122, initially using the pooled sample from which TIC852 was derived and later using total DNA extracted from strain EG5122. This was done to confirm the 5' and 3' end sequences of the native coding sequence corresponding to TIC852 since amplification using primers based upon the TIC807 sequence may have introduced nucleotide changes to the native coding sequence during PCR amplification. Aliquots containing 2.5 micrograms of total DNA from the 96 well plate pool in which EG5122 total DNA was represented was digested with the restriction endonucleases BglII, EcoRI, SalI, SpeI, XbaI or XhoI at 37 degrees Celsius for three hours in the following reaction: 5 ul DNA at 500 ng/ul, 0.1 ul enzyme (6 reactions—BglII, EcoRI, SalI, SpeI, XbaI, or XhoI), 2.5 ul Buffer H, and 17.4 ul ddH2O. The enzymes were then heat inactivated at 65 degrees Celsius for 20 minutes. The aliquots were then diluted and allowed to self-ligate using T4 DNA ligase at 14 degrees Celsius, overnight in the following master mix reaction: 90 ul 5× Ligase Buffer, 4.5 ul T4DNA Ligase, and 310.5 ul ddH2O. Individual ligation reaction contained: 54 ul master mix/tube and 6 ul Digest Reaction to a total of 60 ul. The ligation products served as templates for the inverse PCR reaction. PCR was performed using the Elongase® kit (Invitrogen, Carlsbad, Calif.) and the primers invTIC852for and invTIC852rev (presented as SEQ ID NO:3 and SEQ ID NO:4, respectively) along with the template DNA under the following reaction and cycle parameters: 8 ul dNTP's (10 mM), 8 ul invTIC852for primer (SEQ ID NO: 3), 8 ul invTIC852rev primer (SEQ ID NO: 4), 16 ul Buffer A, 64 ul Buffer B, 8 ul Elongase Enzyme, 208 ul ddH2O. Individual PCR reactions per each of 6 templates included 40 ul Mix/tube and 10 ul Digested, ligated DNA. Cycle parameters were: 94 degrees Celsius for 2 minutes, 35 cycles of: 92 degrees Celsius for 10 seconds, 50 degrees Celsius for 30 seconds, 68 degrees Celsius for 15 minutes, and 4 degrees Celsius hold.

The PCR amplicons were size fractionated on an agarose gel and prominent DNA bands were excised from the gel and purified from the gel slices using the Wizard® SV Gel PCR clean-up system (Promega Madison, Wis.). Purified fragments were cloned into the pCR®2.1-TOPO® vector (Invitrogen, Carlsbad, Calif.) and used to transform *E. coli* cells using electroporation. The plasmids were isolated from each of the transformed cells and the cloned amplicons were sequenced to obtain the 5' and 3' flanking sequence of the coding sequence. Inverse PCR revealed the native sequence contained in EG5122 encoded an amino acid sequence that differed slightly from the TIC852 sequence by 3 amino acids. The native toxin molecule coding sequence (presented as SEQ ID NO: 5) found in strain EG5122 was designated TIC853 and encodes an amino acid sequence (presented as SEQ ID NO: 6) that is homologous but not identical to the amino acid sequence of TIC807 (SEQ ID NO:11).

A non-native coding sequence for the TIC853 protein (presented as SEQ ID NO:7) was produced for cloning and bacterial expression using PCR amplification. The primers INF-853-ATG-f and INF-853-r, presented as SEQ ID NO:8 and SEQ ID NO:9 respectively, were used to produce an amplicon encoding the TIC853 protein (SEQ ID NO:6) using DNA isolated from strain EG5122. The TIC853 amplicon was cloned into the Bt expression vector, pMON101647 using the In-Fusion cloning kit (Clontech Laboratories, Inc., Mountain View, Calif.) and transformed into *E. coli*. After sequence confirmation of the cloned insert, the vector was transformed into the plasmid-less Bt strain, EG10650. The transformed Bt was grown in C2 medium to prepare TIC853 protein for insect testing.

Example 2

The TIC852 and TIC853 Proteins are Toxic to *Lygus*

Recombinant TIC852 and TIC853 proteins were tested for toxicity against western tarnished plant bug (WTPB), *Lygus hesperus* using a bioassay. The recombinant proteins were obtained from transformed Bt strain EG10650 cells harboring the TIC852 or TIC853 expression vectors described in Example 1. In brief, the recombinant strains were grown at 25 to 28 degrees Celsius in C2 medium for 3-4 days or until fully sporulated and lysed. Spores and crystals were collected by centrifugation (e.g. 4000×g for 30 minutes), resuspended in wash buffer (10 mM Tris-HCl, 0.1 mM EDTA, 0.005% Triton X-100, pH 6.8), and collected again by centrifugation. The spore-crystal pellets were resuspended in wash buffer at 1/10th the original culture volume. Crystal proteins present in these 10× C2 concentrates were analyzed by SDS polyacrylamide gel electrophoresis (SDS-PAGE). All four recombinant strains produced a crystal protein of the expected apparent molecular mass of approximately 35 kDa. Protein concentrations were determined by densitometry using bovine serum albumin (BSA) as a standard.

The feeding assay employed was based on a 96 well format and a sachet system as described by Habibi et al., (Archives of Insect Biochem. and Phys. 50: 62-74 (2002)). The artificial diet was supplied by Bio-Serv® (Bio-Serv® Diet F9644B, Frenchtown, N.J.

Five hundred and eighteen milliliters of autoclaved, boiling water were combined with 156.3 grams of Bio-Serv®

Diet F9644B in a surface sterilized blender. Four surface sterilized chicken eggs were broken and the contents were added to the blender containing the diet mix. The mixture was blended until smooth and adjusted to one liter of volume and allowed to cool. Toxin samples were prepared by mixing the toxin protein preparation in the desired concentration with an equivalent volume of the blended diet.

A sheet of Parafilm® (Pechiney Plastic Packing, Chicago, Ill.) was placed over a 96-well format vacuum manifold (Analytical Research Systems, Gainesville, Fla.) with a vacuum of approximately −20 millimeters mercury, which is sufficient to cause extrusion of the Parafilm® into the wells. Forty microliters of test sample were added to the Parafilm® wells. A sheet of Mylar film (Clear Lam Packaging, Inc., Elk Grove Village, Ill.) was then placed over the Parafilm® and sealed gently with a tacking iron (Bienfang Sealector II, Hunt Corporation, Philadelphia, Pa.). The Parafilm® sachets were then placed over a flat-bottom 96-well plate containing the Lygus eggs suspended in agarose. Upon hatching, Lygus nymphs fed by piercing the sachet that is presented above them. Without being limited by theory, it is believed that extraoral digestion in the sachet may lead to proteolysis and degradation prior to ingestion by the insect. To assure intact protein was being presented to the insect in its diet, the diet sachets were replaced every two days. This enhancement in theory allows for longer presentation of the intact toxin proteins in the insect diet over the course of the feeding assay. In addition, lower concentrations of putative toxin protein can be tested since greater amounts of protein will not be required to compensate for potential extraoral digestive effects. Insect diet sachets were replaced on days two and four. Stunting and mortality scores are determined on day 5 and compared to the untreated check (UTC).

Tables 1 and 2 illustrate the toxicity of TIC852 and TIC853 to western tarnished plant bug (WTPB), Lygus hesperus. Spore crystal pellets were prepared from strains expressing TIC852 and TIC853 protein and presented to Lygus hesperus. Significant stunting was observed using TIC852 and TIC853 protein and significant mortality was observed for TIC853 protein. An increase in mortality was observed for insects treated with TIC852 protein relative to the untreated control insects.

TABLE 1

TIC852 and TIC853 stunting scores for western tarnished plant bug (WTPB), Lygus hesperus

| Treatment | Concentration (mg/ml) | N | Mean Stunting | Standard Deviation | P > |t| |
|---|---|---|---|---|---|
| UTC | 0.00 | 3 | 0.00 | 0.00 | |
| TIC852 | 0.488 | 3 | 2.33 | 0.58 | 0.0001 |
| TIC853 | 1.00 | 3 | 3.00 | 0.00 | <0.0001 |

TABLE 2

TIC852 and TIC853 per cent mortality scores for western tarnished plant bug (WTPB), Lygus Hesperus

| Treatment | Concentration (mg/ml) | N | Mean % Mortality | Standard Deviation | P > |t| |
|---|---|---|---|---|---|
| UTC | 0.00 | 3 | 8.33 | 14.43 | |
| TIC852 | 0.488 | 3 | 38.69 | 10.76 | |
| TIC853 | 1.00 | 3 | 41.67 | 19.09 | <0.05 |

Example. 3

TIC853 is Toxic to Colorado Potato Beetle

This example illustrates the toxicity of the insect toxin molecules TIC853 to the Colorado potato beetle (CPB), Leptinotarsa decemlineata, a Coleopteran insect Bioassays with CPB were conducted using an artificial diet consisting of 13.2 g/L agar (Serva 11393), 140.3 g/L Bio-Serve pre-mix (Bio-Serve, Frenchtown, N.J. Catalog #F9380B), 5 ml/L Potassium hydroxide (18.3% w/w) and 1.25 ml/L formalin (37%). The diet was dispensed in 200 microliter aliquots into wells of a 96-well plate and dried briefly prior to sample application. Twenty microliters of test sample were applied per well, with sterile water serving as the untreated check (UTC). Plates were allowed to dry before adding insect larvae. One neonate CPB larva was added per well with a fine paintbrush. Plates were sealed with mylar and ventilated using an insect pin. Forty larvae were tested per treatment. The bioassay plates were incubated at 27 degrees Celsius with 60% relative humidity in complete darkness for 10 to 12 days. The plates were scored for larval mortality. Data were analyzed using JMP® 4 statistical software (SAS Institute, Cary, N.C.). TIC853 demonstrated mortality when fed to CPB. The mean percent mortality scores for TIC853 are presented in Table 3.

TABLE 3

TIC853 percent mortality scores for the Colorado potato beetle (CPB), Leptinotarsa decemlineata

| Treatment | Concentration (mg/ml) | N | Mean % Mortality | Standard Deviation | P > |t| |
|---|---|---|---|---|---|
| UTC | 0 | 3 | 13.10 | 1.03 | |
| TIC853 | 0.5 | 3 | 68.45 | 23.03 | 0.0142 |

Example 4

Toxicity of Purified Crystal Spore Preps of TIC853 to Lygus hesperus

Toxicity of TIC853 to Lygus hesperus was tested using a purified crystal spore prep. Parasporal crystals containing the TIC853 protein were partially purified by sucrose gradient centrifugation. A 10×-concentrated spore-crystal preparation of the TIC853 protein was treated with Benzonase™ (Novagen; 10 U/ml sample) to reduce sample viscosity. The treated sample was allowed to sit overnight at 4 degrees Celcius. Sucrose gradients in Ultraclear™ or Polyclear™ tubes suitable for a SW28 rotor were prepared: 10 mL steps of 79%, 70%, and 55% sucrose in 10 mM Tris-HCl, 0.1 mM EDTA, 0.005% Triton X-100 (pH 7). Approximately 6-7 mL samples were loaded per gradient (tubes filled to ¼ inch from the top). The gradients were run at 18K overnight (16-18 hrs) in a SW28 rotor at 4 degrees Celcius. Crystals were pulled from either the 55-70% interface or the 70-79% interface. Crystals were diluted at least 5-fold in gradient buffer and pelleted by centrifugation (e.g. 8K for 20 min at 4 degrees Celcius). The crystal pellets were resuspended in buffer and examined under a phase-contrast microscope to assess spore contamination. Purified crystals were subsequently treated with 50 mM CAPS-NaOH (pH 11) and incubated at 37 degrees Celcius until the suspension cleared. The solubilized protein was dialyzed against 25 mM sodium carbonate, 10 mM NaCl (pH 8.0), loaded onto a Q-Sepharose column equilibrated with the same buffer, and eluted using a linear 10 mM-500 mM NaCl gradient. The eluted protein was dialyzed against 25 mM sodium carbonate (pH 8.5). The protein was judged to be highly purified by SDS-PAGE analysis. This TIC853 protein preparation was observed to cause significant mortality and stunting (mass reduction) of *Lygus hesperus* nymphs in the feeding assay when compared to the untreated check and are presented in Tables 4 and Table 5 below.

TABLE 4

TIC853 stunting scores for western tarnished plant bug (WTPB), *Lygus hesperus*

| Treatment | Concentration (mg/ml) | N | Mean Stunting | Standard Deviation | P > \|t\| |
|---|---|---|---|---|---|
| UTC | 0 | 8 | 0 | 0 | |
| TIC853 | 0.05 | 5 | 2.0 | 0 | <0.0001 |

TABLE 5

TIC853 per cent mortality scores for western tarnished plant bug (WTPB), *Lygus hesperus*

| Treatment | Concentration (mg/ml) | N | Mean % Mortality | Standard Deviation | P > \|t\| |
|---|---|---|---|---|---|
| UTC | 0 | 8 | 0 | 0 | |
| TIC853 | 0.05 | 5 | 39.0 | 16.7 | 0.0003 |

Similar results were obtained in feeding assays with *Lygus lineolaris*, indicating that TIC853 can also inhibit this *Lygus* species.

Example 5

Synthesis of Genes Encoding a TIC853 Protein that are Designed for Expression in Plants Four nucleotide sequence encoding a TIC853 protein (SEQ ID NO:6) are designed and synthesized. These non-native coding region designed for plant expression is provided here as TIC853-Mc (SEQ ID NO:16 for monocots, especially corn), TIC853-At (SEQ ID NO:17 for *Arabidopsis thaliana*), TIC853-Gm (SEQ ID NO:18 for *Glycine max*, soybean), and TIC853-Gh (SEQ ID NO:19 for *Gossipium hirsutum*, cotton). Each of these synthetic TIC853 coding sequences are characterized by a lower A+T content than the native TIC853 coding region that was derived from *Bacillus thuringiensis* (SEQ ID NO:5), eliminating regions of the native TIC853 gene that are A+T rich and replacing those with sequences that have fewer A+T residues. These sequences are tested in a protoplast system or in stable plant transformation system to determine which sequence expresses transcriptionally and/or translationally well in a species of interest.

Example 6

Expression Cassettes for Expression of a TIC853 Protein in Transgenic Plant Cells or Transgenic Plants A variety of plant expression cassettes can be constructed with the non-native TIC853 coding regions (SEQ ID NOs: 16, 17, 18, and 19). Such expression cassettes are useful for transient expression in plant protoplasts or plant callus.

One series of plant expression cassettes are plastid-targeted expression cassettes comprising an enhanced CaMV35S promoter that is operably linked to a 5' untranslated leader sequence derived from the *Glycine max* Hsp17.9 gene which is operably linked to a coding region comprising an N-terminal *Arabidopsis* shkG chloroplast peptide encoding sequence (i.e. CTP2) fused in frame to a non-native TIC853 encoding sequence from SEQ ID NOs:16, 17, 18 or 19. The respective coding region is operably linked to a 3' terminal CaMV35S polyadenylation site (T-35S). The sequence of the targeted 5'-e35S-Hsp17.9-CTP2-TIC853-Mc-T-35S-3' expression cassette is provided as SEQ ID NO:20. The sequence of the targeted 5'-e35S-Hsp17.9-CTP2-TIC853-At-T-35S-3' expression cassette is provided as SEQ ID NO:21. The sequence of the targeted 5'-e35S-Hsp17.9-CTP2-TIC853-Gm-T-35S-3' expression cassette is provided as SEQ ID NO:22. The sequence of the targeted 5'-e35S-Hsp17.9-CTP2-TIC853-Gh-T-35S-3' expression cassette is provided as SEQ ID NO:23.

Another series of plant expression cassettes are untargeted expression cassettes comprising an enhanced CaMV35S promoter that is operably linked to a 5' untranslated leader sequence derived from the *Glycine max* Hsp17.9 gene which is operably linked to a coding region comprising a non-native TIC853 encoding sequence from SEQ ID NOs:16, 17, 18 or 19. The peptide sequence of the TIC853 protein encoded by these constructs is provided as SEQ ID NO:6. The TIC853 coding region is operably linked to a 3' terminal CaMV35S polyadenylation site (T-35S). The sequence of the untargeted 5'-e35S-Hsp17.9-TIC853-Mc-T-35S-3' expression cassette is provided as SEQ ID NO:24). The sequence of the untargeted 5'-e35S-Hsp17.9-TIC853-At-T-35S-3' expression cassette is provided as SEQ ID NO:25. The sequence of the untargeted 5'-e35S-Hsp17.9-TIC853-Gm-T-35S-3' expression cassette is provided as SEQ ID NO:26. The sequence of the targeted 5'-e35S-Hsp17.9-TIC853-Gh-T-35S-3' expression cassette is provided as SEQ ID NO:27.

Example 7

Construction of *Agrobacterium*-Mediated Transformation Vectors Containing TIC853 Expression Cassettes and Transfer to *Agrobacterium*

To construct *Agrobacterium* mediated transformation vectors, TIC853 expression cassettes are cloned into suitable vectors between the *Agrobacterium* border sequences such that they would be transferred to the genome of a host plant cell by *Agrobacterium* hosts containing the constructed vectors along with a selectable marker gene. More specifically, the restriction fragment containing the entire 5'-e35S-Hsp17.9-CTP2-TIC853-T-35S-3' expression cassette (SEQ ID NOs:20, 21, 22, or 23) is cloned into an *Agrobacterium* plant transformation vector. Similarly, the restriction fragment containing the entire 5'-e35S-Hsp17.9-TIC853-T-35S-3' expression cassette (SEQ ID NOs:24, 25, 26, or 27) is cloned into an *Agrobacterium* plant transformation vector. The vectors containing the TIC853 expression cassettes (i.e., untargeted cassette or and targeted cassette are introduced into *Agrobacterium* by electroporation or by tri-parental mating.

Example 8

Transformation of Cotton with TIC853 *Agrobacterium* Transformation Vectors

Cotton can be transformed with the TIC853 *Agrobacterium* transformation vectors of Example 7 or their equivalents using a procedure substantially similar to the procedure described in U.S. Pat. No. 5,159,135 and U.S. Patent Application Nos. 2008/0282432, 2009/0138985 and 2008/0256667. Any of the targeted plant expression cassettes (SEQ ID NOs:20, 21, 22, or 23) or untargeted plant expression cassettes (SEQ ID NOs:24, 25, 26, or 27) can be used to obtain expression of a TIC853 protein in cotton plants. However, in preferred embodiments, plant expression cassettes that comprise the TIC853-Gh synthetic coding sequence of SEQ ID NO:19 are used. In other preferred embodiments, a targeted plant expression cassette of SEQ ID NO:23 that comprises the TIC853-Gh synthetic coding sequence is used. In still other preferred embodiments, an untargeted plant expression cassette of SEQ ID NO:27 that comprises the TIC853-Gh synthetic coding sequence is used.

Samples from the plantlets can be assayed for expression of TIC853 to identify transgenic plants with insect inhibitory activity.

Example 9

In Planta Testing of TIC853 in Callus Tissue

This example illustrates a non-limiting example of in planta expression of TIC853 for bioassay against *Lygus* and other insect pests that pierce and/or suck the fluids from the cells and tissues of plants.

Cotton cells are transformed with constructs containing the TIC853 protein encoding genes of interest. In this case, non-native A+T rich nucleic acid sequences encoding a TIC853 protein are expressed in cotton cells using the TIC853 expression cassettes in the TIC853 transformation vectors described in the preceding examples. The transformation vectors provide a selectable marker, in this case for selection of kanamycin resistance in transformed plant tissue. TIC853 plant expression vectors that contain TIC853 plant expression cassettes and a selectable marker can be used. Callus tissue is allowed to develop in tissue culture after transformation and selection in a Petri dish. The *Lygus* nymphs are then placed into a Petri dish or microtiter plate well containing callus that is transformed with a TIC853 plant expression cassette. *Lygus* nymphs are also placed into a Petri dish or microtiter plate well containing control callus that is not transformed with a TIC853 plant expression cassette. The secured lid of the Petri dish or microtiter plate well prevents the escape of the *Lygus* nymphs. Any material that will prevent *Lygus* escape but allow gas exchange in the Petri dish, for example, Parafilm® can be used to secure the Petri dish lid or microtiter plate well. A percentage of *Lygus* nymphs will find the callus tissue and feed. Scores for mortality and stunting are then calculated taking into account the background death that will occur from those insects which fail to feed on the callus tissue to obtain an adjusted score. The adjusted scores for the *Lygus* nymphs presented with the TIC853 transformed tissue are compared with the adjusted scores for the *Lygus* nymphs presented with control tissue. Scores for mortality and/or stunting for the *Lygus* nymphs presented with the TIC853 transformed tissue are significantly increased relative to the scores for the *Lygus* nymphs presented with control tissue.

Example 10

In Planta Testing of TIC853 in Leaf Tissue

Alfalfa, cotton, canola, soybean, or lettuce cells are transformed using the TIC853 expression cassettes in the TIC853 transformation vectors described in the preceding examples. Any of the targeted plant expression cassettes (SEQ ID NOs:20, 21, 22, or 23) or untargeted plant expression cassettes (SEQ ID NOs:24, 25, 26, or 27) can be used to obtain expression of a TIC853 protein in alfalfa, cotton, canola, soybean, or lettuce cells, or to obtain expression of a TIC853 protein in alfalfa, cotton, canola, soybean, or lettuce plants derived from the transformed cells. The transformation vectors provide a selectable marker, in this case for selection of kanamycin or glyphosate resistance in transformed plant tissue. The transformed cells are selected for resistance to kanamycin or glyphosate and regenerated into transgenic plants. Insect pests such as *Lygus* nymphs are then allowed to feed when the plant has reached a sufficient level of maturity, such as when the leaves have grown to a size permitting the use of a physical barrier to prevent *Lygus* escape. The barrier to prevent escape of the *Lygus* nymphs can be any commercially available or home made device that permits contact of the *Lygus* nymphs with the leaf tissue and allows the insect to probe and feed from the vascular tissue of the leaf. Clip cages similar to those described by Mowry (1993) (J. Agric. Entomol. 10:181-184) would be sufficient to contain the *Lygus* nymphs for feeding. *Lygus* nymphs are thus presented with leaf tissue from either transgenic plants that express the TIC853 protein or with control leaf tissue that does not express TIC853 protein. The control leaf tissue is ideally provided by a transgenic plant that was selected and regenerated in parallel but does not contain a TIC-encoding transgene. However, leaf tissue from other plants of similar origin and age can also be used so long as the tissue does not contain significant amounts of TIC853 protein. Mortality and stunting scores are then determined with respect to the background death that will occur from those insects which fail to feed on the leaf tissue to obtain an adjusted score. The adjusted scores for the *Lygus* nymphs presented with the TIC853 transformed leaf tissue are compared with the adjusted scores for the *Lygus* nymphs presented with control leaf tissue. Scores for mortality and/or stunting for the *Lygus* nymphs presented with the TIC853 transformed leaf tissue are significantly increased relative to the scores for the *Lygus* nymphs presented with control leaf tissue.

Similar results were obtained in feeding assays with *Lygus lineolaris.*

Example 11

In-Planta Testing of TIC853 in Lettuce Leaf Tissue

Lettuce cells are transformed using the TIC853 expression cassettes in the TIC853 transformation vectors described in the preceding examples. These expression cassettes provide for either targeting of TIC853 to the chloroplast (i.e. with the 5'-e35S-Hsp17.9-CTP2-TIC853-T-35S-3' expression cassettes) or non-targeted (cytoplasmic) expression of TIC853 (i.e. with the 5'-e35S-Hsp17.9-TIC853-T-35S-3' expression cassettes). The transformation vectors provide a selectable marker, in this case for selection of kanamycin resistance in transformed plant tissue. The transformed cells are selected for resistance to kanamycin and regenerated into transgenic plants.

Lettuce seeds are surface sterilized for 20 minutes in 1.2% sodium hypochlorite solution and allowed to dry overnight in a laminar flow hood. The seeds are then plated on 100 ml 0.5× Hoagland's salts (see Table 9 below) in phytatrays (Sigma, St. Louis, Mo., Catalog No: P1552). and grown under the light at 22 to 23 degrees Celsius for 4 to 5 days with a 16 hour photoperiod. *Agrobacterium* transformed with the plant transformation vector of interest are prepared by inoculating 10 mls of liquid Mannitol-Glutamate/Luria medium with 100 microliters of bacterial suspension. The medium is comprised of the following ingredients per liter: 12.5 g LB broth, Miller (Difco #044-017-3), 5.0 g Mannitol, 1.16 g onosodium glutamate (glutamic acid), 0.25 g KH2PO4, 0.10 g MgSO47H2O, 0.001 g Biotin, pH 7.00 and autoclaved.

The liquid culture is incubated on a gyratory shaker at 28 degrees Celsius for 24 hours. Five milliliters of the first overnight cultures are diluted with 15 milliliters of Tryptone Yeast Extract media supplemented with 40 mg/L Acetosyringone (5 grams of Tryptone, 3 grams of Yeast Extract and 20 ml of 2 mg/mL Acetosyringone in total volume of 1000 ml, pH 5.5 and autoclaved). This is then allowed to incubate on a gyratory shaker at 28 degrees Celsius for 24 hours in the dark with 50 mg/L kanamycin and 100 mg/L spectinomycin. One ml of overnight culture is added to 19 milliliters of Tryptone Yeast Extract media and the 600 nm wavelength optical density of the culture is adjusted to 0.08 to 0.09.

Lettuce seedling cotyledons are cut at both the base and the tip and soaked in the diluted *Agrobacterium* medium for 15 minutes. The cotyledons are then plated on MSO-C medium without blotting and kept at 22 to 23 degrees Celsius with a 16 hour photoperiod. Plates are sealed with micropore tape. After 48 hours, cotyledons are transferred to MSO-I medium in 100 mm×25 mm Petri dishes. Explants are subsequently subcultured at 7 and 14 days to MSO-I medium. As shoots develop they are excised and transferred to MSO-SE medium. Shoots are transferred after elongation to phytatrays containing 100 ml of MSO-SE medium. After 6 to 8 weeks, developing shoots are transferred to Magenta boxes containing 100 ml of MSO-R medium. In 7 to 14 days of incubation at 23 degrees Celsius, roots will begin to develop. The shoots are then transferred to 3 inch pots containing soil and allowed to grow. The composition of the MSO mediums is shown in Table 6.

TABLE 6

MSO medium components.

| Ingredients | 0.5 X Hoagland's Salt | MSO-C | MSO-I | MSO-SE | MSO-R |
|---|---|---|---|---|---|
| MSO salts (minimal salts) | | 34.6 g | 34.6 g | 34.6 g | 34.6 g |
| Hoagland's salt | 0.8 g | | | | |
| Naphthaleneacetic acid (1 mg/ml) | | 0.1 ml | 0.1 ml | 0.05 ml | |
| Benzyl adenine (1 mg/ml) | | 0.1 ml | 0.1 ml | 0.01 ml | |
| Acetosyringone (2 mg/ml) | | 20 ml | | | |
| Kanamycin (50 mg/ml) | | | 2 ml | 2 ml | 2 ml |
| Carbenicillin (250 mg/ml) | | | 2 ml | 2 ml | 2 ml |
| Tissue culture grade agar | 7.5 g | 7.5 g | 7.5 g | 8 g | 8 g |
| Total volume | 1000 ml | 1000 ml | 1000 ml | 1000 ml | 1000 ml |
| pH | | 5.7 | 5.7 | 5.7 | 5.7 |

The transgenic plants are self-fertilized and allowed to set seed or are used directly for testing. The leaves of the transformed lettuce plants are used in a culture system to test against *Lygus*. Ten milliliters of sterile plant growth media (Murashige & Skoog, Gamborg B5 vitamins, 3% sucrose and 1.5% agar) is added while in liquid state to sterile 50 milliliter polypropylene conical tubes. The media is allowed to cool and set under sterile conditions. Once set, a sterile circular foam divider, approximately the diameter of the tube containing a small hole in the middle is placed over the plant growth media. Young lettuce leaves are excised with a sterile razor blade and rinsed in sterile deionized water, leaving a portion of the petiole attached to the leaf. The petiole of the excised lettuce leaf is inserted through the hole and allowed to make contact with the media. Ten newly hatched (<12 hours post-hatch) *Lygus* nymphs are added to the tube and a foam stopper is used to close the tube to allow gas exchange. The tube is kept in an incubator set to 25 degrees Celsius with a 14:10 day:night photoperiod. Mortality and stunting scores are then determined with respect to the background death that will occur from those insects which fail to feed on the leaf tissue to obtain an adjusted score. The adjusted scores for the *Lygus* nymphs presented with the TIC853 transformed leaf tissue are compared with the adjusted scores for the *Lygus* nymphs presented with control leaf tissue. Scores for mortality and/or stunting for the *Lygus* nymphs presented with the TIC853 transformed leaf tissue are significantly increased relative to the scores for the *Lygus* nymphs presented with control leaf tissue.

Example 12

TIC853 is Toxic to Colorado Potato Beetle

This example illustrates the toxicity of the insect toxin molecules TIC853 to the Coleopteran, Colorado potato beetle (CPB), *Leptinotarsa decemlineata*. Bioassays with CPB were conducted using an artificial diet consisting of 13.2 g/L agar (Serva 11393), 140.3 g/L Bio-Serve pre-mix (Bio-Serve, Frenchtown, N.J. Catalog #F9380B), 5 ml/L Potassium hydroxide (18.3% w/w) and 1.25 ml/L formalin (37%). The diet was dispensed in 200 microliter aliquots into wells of a 96-well plate and dried briefly prior to sample application. Twenty microliters of test sample were applied per well, with sterile water serving as the untreated check (UTC). Plates were allowed to dry before adding insect larvae. One neonate CPB larva was added per well with a fine paintbrush. Plates were sealed with mylar and ventilated using an insect pin. Forty larvae were tested per treatment. The bioassay plates were incubated at 27 degrees Celsius with 60% relative humidity in complete darkness for 10 to 12 days. The plates were scored for larval mortality. Data were analyzed using JMP® 4 statistical software (SAS Institute, Cary, N.C.). TIC853 demonstrated mortality when fed to CPB. The mean percent mortality scores for TIC853 is presented in Table 7.

It is thus contemplated that TIC853 proteins of the invention can be used to control Coleopteran insects. Coleopteran insects controlled by TIC853 proteins of the invention include, but are not limited to, Colorado potato beetle, wire worm and boll weevil.

TABLE 7

TIC853 percent mortality scores for the Colorado potato beetle (CPB), *Leptinotarsa decemlineata*.

| Treatment | Concentration (mg/ml) | N | Mean % Mortality | Standard Deviation | P > \|t\| |
|---|---|---|---|---|---|
| UTC | 0 | 3 | 13.10 | 1.03 | |
| TIC853 | 0.5 | 3 | 68.45 | 23.03 | 0.0142 |

Example 13

Transformation of Cotton with TIC853 and Toxin Testing Using Whole Cotton Plants Cotton cells are transformed with constructs containing a TIC853 protein encoding gene of interest. In this case, codon redesigned nucleic acid sequences encoding for TIC853 protein are expressed in cotton cells using the TIC853 expression cassettes in the TIC853 transformation vectors described in the preceding examples. The transformation vectors provide a selectable marker, in this case for selection of kanamycin or glyphosate resistance in transformed plant tissue. Other equivalent TIC853 plant expression vectors that contain TIC853 plant expression cassettes and a selectable marker can also be used.

Bioassay on plants expressing the TIC853 toxin molecule can be performed using an enclosed cotton branch assay. Cotton plants are grown to an early bloom stage where several fruiting branches containing squares (i.e. immature cotton flowers) are available. Sleeves are prepared using breathable plastic sheets (Vilutis and Co. Inc., Frankfort, Ill.). Sleeves are made using a standard photography or arts and craft tacking iron to create a seam producing a bag with an approximate dimension of 5 inches×5 inches×12 inches long. Terminal branches including at least one pre-bloom square and unfolded terminal leaf are inserted into the open end of the sleeve. Alternatively, bags can be set up to enclose bolls or other tissues if desired. The bag is closed around the branch using a twist tie. Leaves and squares below the desired enclosed tissue can be removed to facilitate secure closer with the twist tie. The other end of the sleeve is left open to allow insect infestation. *Lygus* nymphs are collected with an aspirator and 4 nymphs are put into a 2 dram shell vial. Initial mass of the nymphs is recorded for each vial containing the nymphs. The tube is tapped gently to assure the nymphs are at the bottom of the tube and the cap of the tube is removed. The tube is placed inside the sleeve exposing the nymphs to the cotton plant tissue. The open end of the sleeve is then closed using a twist tie. The insects are allowed to remain in the sleeves and feed upon the enclosed cotton plant material for a specified number of days. After the specified time, the cotton branches are removed. The sleeves are carefully opened to count the surviving nymphs. All nymphs are collected and weighed. Mortality and stunting scores are then determined with respect to non-transformed control plants. The adjusted scores for the *Lygus* nymphs presented with the TIC853 transformed cotton tissue are compared with the adjusted scores for the *Lygus* nymphs presented with control cotton tissue that lacks the TIC853 protein. Scores for mortality and/or stunting for the *Lygus* nymphs presented with the TIC853 transformed cotton tissue are significantly increased relative to the scores for the *Lygus* nymphs presented with control cotton tissue.

Example 14

Combining TIC853 Toxin with Nectariless Cotton

This example illustrates using the nectariless phenotype of cotton in combination with TIC853 protein expression to provide greater control of an insect pest. Lack of nectaries has been identified as arising from homozygosity for recessive mutations at two duplicate loci in *Gossypium tomentosum* (Meyer and Meyer, 1961, Crop Science, 1: 167-169). Crosses with *Gossypium hirsutum* with *Gossypium tomentosum* demonstrated a significant reduction in populations of cabbage loopers and cotton leafworms in caged experiments relative to ordinary varieties of cotton in which floral nectarines are present (Lukefahr and Rhyne, 1960, Econ. Entomol. 53: 242-244). This is presumably the direct result of nectariless cotton lines being less palatable to the insect pest as well as the lack of sustenance provided by the nectars. Multiple mechanisms of resistance may be particularly crucial in Gossypieae species because extrafloral nectaries can directly attract some herbivore species. Extrafloral nectaries in cultivated cotton can enhance the abundance of or damage by several crop pests including Lepidopterans and plant bugs (Trelease, 1879, Nectar; what it is, and some of its uses. In J. H. Comstock [ed.], Report upon cotton insects, 319-343. U.S. Department of Agriculture Publication, U.S. Government Publication Office, Washington, D.C., USA. Lukefahr and Rhyne, 1960; Lukefahr et al., 1960, Journal of Econ Entom 53: 516-518; Benschoter and Leal, 1974, Journal of Econ Entom 67: 217-218; Schuster et al., 1976, Journal of Econ Entom 69: 400-402; Wilson and Wilson, 1976, Journal of Econ Entom 69: 623-624; Henneberry et al., 1977, Journal of Econ Entom 70: 797-799; Adjei-Maafo et al., 1983, Environ Entom 12: 353-358; Beach et al., 1985, Journal of Entomological Science 20: 233-236; Smith, 1992, Advances in Agronomy 48: 251-296; Summy and King, 1992, Crop Protection 11: 307-319), mainly because adults of these taxa consume extrafloral nectar.

Lines produced by crosses of *G. hirsutum* with *G. tomentosum* are selected for the presence of the nectariless phenotype and favorable agronomic traits. In other embodiments, lines obtained from the commercial germplasm Stoneville 825 can be used as a source of germplasm comprising the nectariless phenotype. In one embodiment of the method, the selected nectariless lines are then transformed with an expression cassette encoding either a TIC853 protein, the TIC809/TIC810 proteins, the TIC128 protein or combinations thereof, or any other toxin molecule directed to a pest of cotton in which the presence of nectaries act as an attractant to the insect pest. In another embodiment of the method, transgene inserts comprising an expression cassette encoding either a TIC853 protein, the TIC809/TIC810 proteins, the TIC128 protein or combinations thereof, or any other toxin molecule directed to a pest of cotton in which the presence of nectaries act as an attractant to the insect pest are obtained in any suitable cotton germplasm and then introgressed into lines produced by crosses of *G. hirsutum* with *G. tomentosum* that have been selected for the presence of the nectariless phenotype and favorable agronomic traits. Through breeding methods known to one of ordinary skill in the art, the transformant lines expressing the nectariless phenotypes are selected and maintained in subsequent generations to contain both the nectariless phenotype and the insect toxin molecule.

Example 15

Toxicity of TIC853, Cry51Aa1, or TIC807 to Colorado Potato Beetle Larvae

This example illustrates the toxicity of the insect toxin molecules TIC853, Cry51Aa1, or TIC807 to larvae of the Colorado potato beetle (CPB), *Leptinotarsa decemlineata*, a Coleopteran insect pest. Bioassays with CPB were conducted using an artificial diet consisting of 13.2 g/L agar (Serva 11393), 140.3 g/L Bio-Serve pre-mix (Bio-Serve, Frenchtown, N.J. Catalog #F9380B), 5 ml/L potassium hydroxide (18.3% w/w) and 1.25 ml/L formalin (37%). The diet was dispensed in 200 microliter aliquots into wells of a 96-well plate and dried briefly prior to sample application. Protein crystals containing TIC853 or Cry51Aa1 were solubilized in 200 mM sodium carbonate buffer, pH 10.5 for 3 hr at 37° C. and the supernatant fraction dialyzed against 25 mM sodium carbonate pH 10.5. TIC807 protein was extracted from a spore-crystal pellet in 50 mM sodium carbonate buffer, pH10.5, containing 10 mM DTT. The protein was loaded onto Q sepharose column with pH 9.0 buffer and eluted with about 0.25M NaCl solution. Salt was removed by dialysis in 20 mM sodium carbonate buffer, pH 9, to obtain 98% pure protein. All proteins were quantified by sodium dodecyl sulfate (SDS) gel electrophoresis using bovine serum albumin as a standard for densitometry. Twenty microliters of protein sample per concentration were applied per well with 25 mM sodium carbonate, pH 10 serving as the untreated check (UTC). Plates were allowed to dry before adding insect larvae. One neonate CPB larva was added per well with a fine paintbrush. Plates were sealed with mylar and ventilated using an insect pin. Forty larvae were tested per treatment. The bioassay plates were incubated at 27 degrees Celsius with 60% relative humidity in complete darkness for 5 to 6 days. The plates were scored for larval mortality. Data were analyzed using JMP® 4 statistical software (SAS Institute, Cary, N.C.). The mean percent mortality scores for TIC853, Cry51Aa1, or TIC807 as compare to the UTC are presented in Table 8 TIC853 appears to be more active than either Cry51Aa1 or TIC807 in the CPB bioassay.

TABLE 8

TIC853, Cry51Aa1, or TIC807 percent mortality scores for the Colorado potato beetle (CPB), *Leptinotarsa decemlineata*

| Treatment | Concentration (mg/ml) | N | Mean % Mortality | Standard Deviation |
|---|---|---|---|---|
| TIC853 | 0.05 | 5 | 37.50 | 8.84 |
| TIC853 | 0.1 | 5 | 65.00 | 20.54 |
| TIC853 | 0.25 | 5 | 67.50 | 18.96 |
| Cry51Aa1 | 0.05 | 5 | 17.50 | 11.18 |
| Cry51Aa1 | 0.1 | 5 | 25.00 | 12.50 |
| Cry51Aa1 | 0.25 | 5 | 25.71 | 8.98 |
| TIC807 | 0.05 | 5 | 12.5 | 12.50 |
| TIC807 | 0.1 | 5 | 32.50 | 20.92 |
| TIC807 | 0.25 | 5 | 22.50 | 16.30 |

Various patent and non-patent publications are cited herein, the disclosures of each of which are incorporated herein by reference in their entireties. Documents cited herein as being available from the World Wide Web at certain internet addresses are also incorporated herein by reference in their entireties. Certain biological sequences referenced herein by their "NCBI Accession Number" can be accessed through the National Center of Biotechnology Information on the world wide web at ncbi.nlm.nih.gov.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for controlling a *Lygus* insect, said method comprising
    manually or mechanically applying a *Lygus* inhibitory amount of a TIC853 insect inhibitory protein, wherein said TIC853 insect inhibitory protein comprises a polypeptide sequence that has at least 95% sequence identity to the amino acid sequence as set forth in SEQ ID NO:6 over a length of at least 300 amino acids.

2. The method of claim 1, wherein said *Lygus* inhibitory amount of said TIC853 insect inhibitory protein is applied in a *Lygus* diet.

3. The method of claim 1, wherein said *Lygus* inhibitory amount of said TIC853 insect inhibitory protein is applied by spraying a composition comprising said TIC853 insect inhibitory protein on a plant.

4. The method of claim 3, wherein said composition comprises bacterial cells or bacterial spores that express said TIC853 insect inhibitory protein.

5. A method for controlling at least one insect pest, said method comprising providing an insect inhibitory amount of an insect inhibitory composition comprising insect inhibitory proteins comprising a polypeptide sequence that has at least 95% sequence identity to the amino acid sequence as set forth in SEQ ID NO:6 over a length of at least 300 amino acids and at least one other insect inhibitory agent that is a protein that has less than 95% sequence identity to the amino acid sequence as set forth in SEQ ID NO:6 over a length of at least 300 amino acids, or is a non-protein agent, wherein said insect inhibitory composition is provided by spraying said composition on a plant.

6. The method of claim 5, wherein said at least one insect pest is a *Lygus* insect.

7. The method of claim 6, wherein said insect inhibitory composition is provided in a *Lygus* diet.

8. A method for protecting a plant from insect pest infestation, said method comprising:

providing a transgenic plant seed, wherein a plant grown from said transgenic plant seed expresses a polynucleotide encoding a polypeptide sequence that has at least 95% sequence identity to the amino acid sequence as set forth in SEQ ID NO:6 over a length of at least 300 amino acids.

9. The method of claim 8, further comprising applying to said transgenic plant seed at least one insect inhibitory agent that is different from said TIC853 insect inhibitory protein, wherein said insect inhibitory agent is a dsRNA, a protein other than an insect toxin that has insect inhibitory properties, a synthetic pesticide, a semi-synthetic pesticide, an organic pesticide, or an insect toxin protein selected from the group consisting of AXMI-027, AXMI-036, AXMI-038, AXMI-018, AXMI-020, AXMI-021, AXMI-010, AXMI-003, AXMI-008, AXMI-006, AXMI-007, AXMI-009, AXMI-014, ET29, ET37, AXMI-004, AXMI-028, AXMI-029, AXMI-007, AXMI-008, AXMI-0080rf2, AXMI-009, AXMI-014, TIC807, TIC809, TIC810, TIC812, TIC127 and TIC128, and wherein said at least one insect inhibitory agent that is different from said TIC853 is a protein that comprises less than 95% sequence identity to the amino acid sequence as set forth in SEQ ID NO:6 over a length of at least 300 amino acids.

10. The method of claim 1, wherein said TIC853 insect inhibitory protein comprises a polypeptide sequence that has at least 98% sequence identity to the amino acid sequence as set forth in SEQ ID NO:6 over a length of at least 300 amino acids.

11. The method of claim 1, wherein said TIC853 insect inhibitory protein comprises a polypeptide sequence that has at least 99% sequence identity to the amino acid sequence as set forth in SEQ ID NO:6 over a length of at least 300 amino acids.

12. The method of claim 1, wherein said TIC853 insect inhibitory protein comprises a polypeptide sequence that has 100% sequence identity to the amino acid sequence as set forth in SEQ ID NO:6 over a length of at least 300 amino acids.

13. The method of claim 8, wherein said polynucleotide encodes a polypeptide sequence that has at least 98% sequence identity to the amino acid sequence as set forth in SEQ ID NO:6 over a length of at least 300 amino acids.

14. The method of claim 8, wherein said polynucleotide encodes a polypeptide sequence that has at least 99% sequence identity to the amino acid sequence as set forth in SEQ ID NO:6 over a length of at least 300 amino acids.

15. The method of claim 8, wherein said polynucleotide encodes a polypeptide sequence that has 100% sequence identity to the amino acid sequence as set forth in SEQ ID NO:6 over a length of at least 300 amino acids.

* * * * *

SEQUENCE LISTING

<160> NUMBER OF SEQ ID NOS: 55

<210> SEQ ID NO 1
<211> LENGTH: 921
<212> TYPE: DNA
<213> ORGANISM: Bacillus thuringiensis

<400> SEQUENCE: 1

```
atggcaattt tagatttaaa atctttagta ctcaatgcaa taaactattg gggtcctaaa      60
aataataatg gtatacaggg ttataatttt aattcccta tatcagaaag acaaatagat       120
acgtcgatta taacttctac tcattctcgt ttaatgccac atgatttaac aattcctcaa     180
aatttagaaa ctattttac tacaactcaa gtattaacaa ataatacaga tgtacaacaa      240
agtcaaactg tttctttttc taaaaaaaca acgacaacaa cttcaacttc aactacagat     300
ggttggacag aaggtgggag aatttcagat acattagaag aaaacgtaag tgtatctatt     360 cctttattg gagcgggagg agcaaaaaac agtacaacta tagaagctaa tgttgcacat      420
aactctagta ctactacttc tcaacaggct tcaactgaga tagagtggaa tatttcacaa     480
ccagtattgg ttcccccacg taaacaagtt gtagcaacat tagttattat gggaggtgat    540
```

```
tttactgttc ctatggattt gataactact atagattcta cacaacattt tactggttat     600
ccaatattaa catggataga gaaccccgag cataatgtta gaggtcgatt tctgagttgg     660 tttttgcaa attggcccaa tttaccatcg gagtttggtt ctttaaattc agataatacg      720
atcacttata aaggttctgt tgtaagtcga atatcagctg gtgtatatgc tactgtacga     780
tttgatcaat atgctataaa taatttaaga acaattgaaa aaacttggta tgcacgacat     840
ggaactcttc ataatggaaa gaaaatatct ataaataatg ttactgaaat ggcaccaaca     900
agtccaataa aaacaaatta a                                               921
```

<210> SEQ ID NO 2
<211> LENGTH: 306
<212> TYPE: PRT
<213> ORGANISM: Bacillus thuringiensis

<400> SEQUENCE: 2

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Tyr Asn Phe Asn Tyr
            20                  25                  30

Pro Ile Ser Glu Arg Gln Ile Asp Thr Ser Ile Ile Thr Ser Thr His
        35                  40                  45

Ser Arg Leu Met Pro His Asp Leu Thr Ile Pro Gln Asn Leu Glu Thr
    50                  55                  60

Ile Phe Thr Thr Thr Gln Val Leu Thr Asn Asn Thr Asp Val Gln Gln
65                  70                  75                  80

Ser Gln Thr Val Ser Phe Ser Lys Lys Thr Thr Thr Thr Thr Ser Thr
                85                  90                  95

Ser Thr Thr Asp Gly Trp Thr Glu Gly Gly Arg Ile Ser Asp Thr Leu
            100                 105                 110

Glu Glu Asn Val Ser Val Ser Ile Pro Phe Ile Gly Ala Gly Gly Ala
        115                 120                 125

Lys Asn Ser Thr Thr Ile Glu Ala Asn Val Ala His Asn Ser Ser Thr
    130                 135                 140

Thr Thr Ser Gln Gln Ala Ser Thr Glu Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asp Phe Thr Val Pro Met Asp Leu Ile Thr Thr Ile Asp
            180                 185                 190

Ser Thr Gln His Phe Thr Gly Tyr Pro Ile Leu Thr Trp Ile Glu Asn
        195                 200                 205

Pro Glu His Asn Val Arg Gly Arg Phe Leu Ser Trp Phe Phe Ala Asn
    210                 215                 220

Trp Pro Asn Leu Pro Ser Glu Phe Gly Ser Leu Asn Ser Asp Asn Thr
225                 230                 235                 240

Ile Thr Tyr Lys Gly Ser Val Val Ser Arg Ile Ser Ala Gly Val Tyr
                245                 250                 255

Ala Thr Val Arg Phe Asp Gln Tyr Ala Ile Asn Asn Leu Arg Thr Ile
            260                 265                 270

Glu Lys Thr Trp Tyr Ala Arg His Gly Thr Leu His Asn Gly Lys Lys
        275                 280                 285

Ile Ser Ile Asn Asn Val Thr Glu Met Ala Pro Thr Ser Pro Ile Lys
    290                 295                 300
```

Thr Asn
305

<210> SEQ ID NO 3
<211> LENGTH: 21
<212> TYPE: DNA
<213> ORGANISM: Artificial
<220> FEATURE:
<223> OTHER INFORMATION: synthetic

<400> SEQUENCE: 3
agagaacccc gagcataatg t                                              21

<210> SEQ ID NO 4
<211> LENGTH: 33
<212> TYPE: DNA
<213> ORGANISM: Artificial
<220> FEATURE:
<223> OTHER INFORMATION: synthetic

<400> SEQUENCE: 4
ccatgttaat attggataac cagtaaaatg ttg                                 33

<210> SEQ ID NO 5
<211> LENGTH: 921
<212> TYPE: DNA
<213> ORGANISM: Bacillus thuringiensis

<400> SEQUENCE: 5
ttggcaattt tagatttaaa atctttagta ctcgatgcaa taaactattg gggtcctaaa    60
aataataatg gtatacaggg ttataatttt aattacccta tatcagaaag acaaatagat   120
acgtcgatta taacttctac tcattctcgt ttaatgccac atgatttaac aattcctcaa   180
aatttagaaa ctatttttac tacaactcaa gtattaacaa ataatacaga tgtacaacaa   240
agtcaaactg tttcttttc taaaaaaaca acgacaacaa cttcaacttc aactacagat   300
ggttggacag aaggtgggag aatttcagat acattagaag aaaacgtaag tgtatctatt   360
cctttattg gagcgggagg agcaaaaaac agtacaacta tagaagctaa tgttgcacat   420
aactctagta ctactacttc tcaacaggct tcaactgaga tagagtggaa tatttcacaa   480
ccagtattgg ttcccccacg taaacaagtt gtagcaacat tagttattat gggaggtgat   540
tttactgttc ctatggattt gataactact atagattcta cacaacattt tactggttat   600
ccaatattaa catggataga aaccccgag cataatgtta gaggtcgatt tctgagttgg   660
tttttgcaa attggcccaa tttaccatcg gagtttggtt ctttaaattc agataatacg   720
atcacttata aaggttctgt tgtaagtcga atatcagctg gtgtatatgc tactgtacga   780
tttgatcaat atgctataaa taatttaaga acaattgaaa aaacttggta tgcacgacat   840
ggaactcttc ataatggaaa gaaaatatct ataaataatg ttactgaaat ggcaccaaca   900
agtccaatag aaagaaatta a                                             921

<210> SEQ ID NO 6
<211> LENGTH: 306
<212> TYPE: PRT
<213> ORGANISM: Bacillus thuringiensis

<400> SEQUENCE: 6

Met Ala Ile Leu Asp Leu Lys Ser Leu Val Leu Asp Ala Ile Asn Tyr
1               5                   10                  15

Trp Gly Pro Lys Asn Asn Asn Gly Ile Gln Gly Tyr Asn Phe Asn Tyr

```
            20                  25                  30
Pro Ile Ser Glu Arg Gln Ile Asp Thr Ser Ile Ile Thr Ser Thr His
        35                  40                  45

Ser Arg Leu Met Pro His Asp Leu Thr Ile Pro Gln Asn Leu Glu Thr
    50                  55                  60

Ile Phe Thr Thr Thr Gln Val Leu Thr Asn Asn Thr Asp Val Gln Gln
65                  70                  75                  80

Ser Gln Thr Val Ser Phe Ser Lys Lys Thr Thr Thr Thr Ser Thr
                85                  90                  95

Ser Thr Thr Asp Gly Trp Thr Glu Gly Gly Arg Ile Ser Asp Thr Leu
            100                 105                 110

Glu Glu Asn Val Ser Val Ser Ile Pro Phe Ile Gly Ala Gly Gly Ala
        115                 120                 125

Lys Asn Ser Thr Thr Ile Glu Ala Asn Val Ala His Asn Ser Ser Thr
    130                 135                 140

Thr Thr Ser Gln Gln Ala Ser Thr Glu Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asp Phe Thr Val Pro Met Asp Leu Ile Thr Thr Ile Asp
            180                 185                 190

Ser Thr Gln His Phe Thr Gly Tyr Pro Ile Leu Thr Trp Ile Glu Asn
        195                 200                 205

Pro Glu His Asn Val Arg Gly Arg Phe Leu Ser Trp Phe Phe Ala Asn
    210                 215                 220

Trp Pro Asn Leu Pro Ser Glu Phe Gly Ser Leu Asn Ser Asp Asn Thr
225                 230                 235                 240

Ile Thr Tyr Lys Gly Ser Val Val Ser Arg Ile Ser Ala Gly Val Tyr
                245                 250                 255

Ala Thr Val Arg Phe Asp Gln Tyr Ala Ile Asn Asn Leu Arg Thr Ile
            260                 265                 270

Glu Lys Thr Trp Tyr Ala Arg His Gly Thr Leu His Asn Gly Lys Lys
        275                 280                 285

Ile Ser Ile Asn Asn Val Thr Glu Met Ala Pro Thr Ser Pro Ile Glu
    290                 295                 300

Arg Asn
305

<210> SEQ ID NO 7
<211> LENGTH: 921
<212> TYPE: DNA
<213> ORGANISM: Artificial
<220> FEATURE:
<223> OTHER INFORMATION: synthetic

<400> SEQUENCE: 7
atggcaattt tagatttaaa atctttagta ctcgatgcaa taaactattg gggtcctaaa      60
aataataatg gtatacaggg ttataatttt aattacccta tatcagaaag acaaatagat     120
acgtcgatta taacttctac tcattctcgt ttaatgccac atgatttaac aattcctcaa     180
aatttagaaa ctatttttac tacaactcaa gtattaacaa ataatacaga tgtacaacaa     240
agtcaaactg tttctttttc taaaaaaaca acgacaacaa cttcaacttc aactacagat     300
ggttggacag aaggtgggag aatttcagat acattagaag aaaacgtaag tgtatctatt     360
cctttttatt gagcgggagg agcaaaaaac agtacaacta tagaagctaa tgttgcacat     420
```

```
aactctagta ctactacttc tcaacaggct tcaactgaga tagagtggaa tatttcacaa    480
ccagtattgg ttcccccacg taaacaagtt gtagcaacat tagttattat gggaggtgat    540
tttactgttc ctatggattt gataactact atagattcta cacaacattt tactggttat    600
ccaatattaa catggataga gaaccccgag cataatgtta gaggtcgatt tctgagttgg    660 tttttttgcaa attggcccaa tttaccatcg gagtttggtt ctttaaattc agataatacg    720
atcacttata aaggttctgt tgtaagtcga atatcagctg gtgtatatgc tactgtacga    780
tttgatcaat atgctataaa taatttaaga acaattgaaa aaacttggta tgcacgacat    840
ggaactcttc ataatggaaa gaaaatatct ataaataatg ttactgaaat ggcaccaaca    900
agtccaatag aaagaaatta a                                              921

<210> SEQ ID NO 8
<211> LENGTH: 48
<212> TYPE: DNA
<213> ORGANISM: Artificial
<220> FEATURE:
<223> OTHER INFORMATION: synthetic

<400> SEQUENCE: 8
gagatggagg aagaagatgg caattttaga tttaaaatct ttagtact                 48

<210> SEQ ID NO 9
<211> LENGTH: 58
<212> TYPE: DNA
<213> ORGANISM: Artificial
<220> FEATURE:
<223> OTHER INFORMATION: synthetic

<400> SEQUENCE: 9
attctgagag caagagttaa tttctttcta ttggacttgt tggtgccatt tcagtaac      58

<210> SEQ ID NO 10
<211> LENGTH: 930
<212> TYPE: DNA
<213> ORGANISM: Bacillus thuringiensis

<400> SEQUENCE: 10
ttggcaattt tagatttaaa atctttagta ctcaatgcaa taaattattg gggtcctaaa    60
aataataatg gcatacaggg tggtgatttt ggttacccta tatcagaaaa acaaatagat    120
acgtctatta taacttttac tcatcctcgt ttaattccat atgatttaac aattcctcaa    180
aatttagaaa ctattttttac tacaactcaa gtattaacaa ataatacaga tttacaacaa    240
agtcaaactg tttctttttgc taaaaaaaca acgacaacaa cttcaacttc aactacaaat    300
ggttggacag aaggtgggaa aatttcagat acattagaag aaaaagtaag tgtatctatt    360 cctttttattg gagagggagg aggaaaaaac agtacaacta gaaagctaa ttttgcacat    420 aactctagta ctactacttt tcaacaggct tcaactgata tagagtggaa tatttcacaa    480
ccagtattgg ttcccccaag taaacaagtt gtagcaacat tagttattat gggaggtaat    540
tttactattc ctatggattt gatgactact atagattcta cagaacatta tagccattat    600
agtggttatc caatattaac atggatatcg agccccgata atagtatag tggtccattt    660 atgagttggt attttgcaaa ttggcccaat ttaccatcgg ggtttggtcc tttaaattca    720
gataatacgg tcacttatac aggttctgtt gtaagtcaag tatcagctgg tgtatatgcc    780
actgtacgat ttgatcaata tgatatacac aatttaagga caattgaaaa aacttggtat    840
```

```
gcacgacatg caactcttca taatggaaag aaaatatcta taaataatgt tactgaaatg    900
gcaccaacaa gtccaataaa aacaaattaa                                    930
```

<210> SEQ ID NO 11
<211> LENGTH: 309
<212> TYPE: PRT
<213> ORGANISM: Bacillus thuringiensis

<400> SEQUENCE: 11

```
Met Ala Ile Leu Asp Leu Lys Ser Leu Val Le

-continued

<400> SEQUENCE: 12
caccatggca attttagatt taaaatcttt agtactcaat gcaat　　　　　　　　　　　　　45

<210> SEQ ID NO 13
<211> LENGTH: 42
<212> TYPE: DNA
<213> ORGANISM: Artificial
<220> FEATURE:
<223> OTHER INFORMATION: synthetic

<400> SEQUENCE: 13
ttaatttgtt tttattggac ttgttggtgc catttcagta ac　　　　　　　　　　　　　　42

<210> SEQ ID NO 14
<211> LENGTH: 930
<212> TYPE: DNA
<213> ORGANISM: Bacillus thuringiensis
<220> FEATURE:
<221> NAME/KEY: CDS
<222> LOCATION: (1)..(930)
<223> OTHER INFORMATION: cry51Aa1 from NCBI Acc. No. DQ836184

<400> SEQUENCE: 14

```
atg att ttt ttg gca att tta gat tta aaa tct tta gta ctc aat gca      48
Met Ile Phe Leu Ala Ile Leu Asp Leu Lys Ser Leu Val Leu Asn Ala
1               5                  10                  15 ata aat tat tgg ggt cct aaa aat aat aat ggc ata cag ggt ggt gat      96
Ile Asn Tyr Trp Gly Pro Lys Asn Asn Asn Gly Ile Gln Gly Gly Asp
            20                  25                  30 ttt ggt tac cct ata tca gaa aaa caa ata gat acg tct att ata act     144
Phe Gly Tyr Pro Ile Ser Glu Lys Gln Ile Asp Thr Ser Ile Ile Thr
        35                  40                  45 tct act cat cct cgt tta att cca cat gat tta aca att cct caa aat     192
Ser Thr His Pro Arg Leu Ile Pro His Asp Leu Thr Ile Pro Gln Asn
    50                  55                  60 tta gaa act att ttt act aca act caa gta tta aca aat aat aca gat     240
Leu Glu Thr Ile Phe Thr Thr Thr Gln Val Leu Thr Asn Asn Thr Asp
65                  70                  75                  80 tta caa caa agt caa act gtt tct ttt gct aaa aaa aca acg aca aca     288
Leu Gln Gln Ser Gln Thr Val Ser Phe Ala Lys Lys Thr Thr Thr Thr
                85                  90                  95 act tca act tca act aca aat ggt tgg aca gaa ggt ggg aaa att tca     336
Thr Ser Thr Ser Thr Thr Asn Gly Trp Thr Glu Gly Gly Lys Ile Ser
            100                 105                 110 gat aca tta gaa gaa aaa gta agt gta tct att cct ttt att gga gag     384
Asp Thr Leu Glu Glu Lys Val Ser Val Ser Ile Pro Phe Ile Gly Glu
        115                 120                 125 gga gga gga aaa aac agt aca act ata gaa gct aat ttt gca cat aac     432
Gly Gly Gly Lys Asn Ser Thr Thr Ile Glu Ala Asn Phe Ala His Asn
    130                 135                 140 tct agt act act act ttt caa cag gct tca act gat ata gag tgg aat     480
Ser Ser Thr Thr Thr Phe Gln Gln Ala Ser Thr Asp Ile Glu Trp Asn
145                 150                 155                 160 att tca caa cca gta ttg gtt ccc cca cgt aaa caa gtt gta gca aca     528
Ile Ser Gln Pro Val Leu Val Pro Pro Arg Lys Gln Val Val Ala Thr
                165                 170                 175 tta gtt att atg gga ggt aat ttt act att cct atg gat ttg atg act     576
Leu Val Ile Met Gly Gly Asn Phe Thr Ile Pro Met Asp Leu Met Thr
            180                 185                 190 act ata gat tct aca gaa cat tat agt ggt tat cca ata tta aca tgg     624
Thr Ile Asp Ser Thr Glu His Tyr Ser Gly Tyr Pro Ile Leu Thr Trp
```

```
                   195                 200                 205
ata tcg agc ccc gat aat agt tat aat ggt cca ttt atg agt tgg tat      672
Ile Ser Ser Pro Asp Asn Ser Tyr Asn Gly Pro Phe Met Ser Trp Tyr
    210                 215                 220 ttt gca aat tgg ccc aat tta cca tcg ggg ttt ggt cct tta aat tca      720
Phe Ala Asn Trp Pro Asn Leu Pro Ser Gly Phe Gly Pro Leu Asn Ser
225                 230                 235                 240 gat aat acg gtc act tat aca ggt tct gtt gta agt caa gta tca gct      768
Asp Asn Thr Val Thr Tyr Thr Gly Ser Val Val Ser Gln Val Ser Ala
                245                 250                 255 ggt gta tat gcc act gta cga ttt gat caa tat gat ata cac aat tta      816
Gly Val Tyr Ala Thr Val Arg Phe Asp Gln Tyr Asp Ile His Asn Leu
        260                 265                 270 agg aca att gaa aaa act tgg tat gca cga cat gca act ctt cat aat      864
Arg Thr Ile Glu Lys Thr Trp Tyr Ala Arg His Ala Thr Leu His Asn
    275                 280                 285 gga aag aaa ata tct ata aat aat gtt act gaa atg gca cca aca agt      912
Gly Lys Lys Ile Ser Ile Asn Asn Val Thr Glu Met Ala Pro Thr Ser
290                 295                 300 cca ata aaa aca aat taa                                              930
Pro Ile Lys Thr Asn
305
```

<210> SEQ ID NO 15
<211> LENGTH: 309
<212> TYPE: PRT
<213> ORGANISM: Bacillus thuringiensis

<400> SEQUENCE: 15

```
Met Ile Phe Leu Ala Ile Leu Asp Leu Lys Ser Leu Val Leu Asn Ala
1               5                   10                  15

Ile Asn Tyr Trp Gly Pro Lys Asn Asn Asn Gly Ile Gln Gly Gly Asp
            20                  25                  30

Phe Gly Tyr Pro Ile Ser Glu Lys Gln Ile Asp Thr Ser Ile Ile Thr
        35                  40                  45

Ser Thr His Pro Arg Leu Ile Pro His Asp Leu Thr Ile Pro Gln Asn
    50                  55                  60

Leu Glu Thr Ile Phe Thr Thr Thr Gln Val Leu Thr Asn Asn Thr Asp
65                  70                  75                  80

Leu Gln Gln Ser Gln Thr Val Ser Phe Ala Lys Lys Thr Thr Thr Thr
                85                  90                  95

Thr Ser Thr Ser Thr Thr Asn Gly Trp Thr Glu Gly Gly Lys Ile Ser
            100                 105                 110

Asp Thr Leu Glu Glu Lys Val Ser Val Ser Ile Pro Phe Ile Gly Glu
        115                 120                 125

Gly Gly Gly Lys Asn Ser Thr Thr Ile Glu Ala Asn Phe Ala His Asn
    130                 135                 140

Ser Ser Thr Thr Thr Phe Gln Gln Ala Ser Thr Asp Ile Glu Trp Asn
145                 150                 155                 160

Ile Ser Gln Pro Val Leu Val Pro Pro Arg Lys Gln Val Val Ala Thr
                165                 170                 175

Leu Val Ile Met Gly Gly Asn Phe Thr Ile Pro Met Asp Leu Met Thr
            180                 185                 190

Thr Ile Asp Ser Thr Glu His Tyr Ser Gly Tyr Pro Ile Leu Thr Trp
        195                 200                 205

Ile Ser Ser Pro Asp Asn Ser Tyr Asn Gly Pro Phe Met Ser Trp Tyr
    210                 215                 220
```

```
Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
            245                 250                 255

Gly Val Tyr Ala Thr Val Arg Phe Asp Gln Tyr Asp Ile His Asn Leu
        260                 265                 270

Arg Thr Ile Glu Lys Thr Trp Tyr Ala Arg His Ala Thr Leu His Asn
    275                 280                 285

Gly Lys Lys Ile Ser Ile Asn Asn Val Thr Glu Met Ala Pro Thr Ser
290                 295                 300

Pro Ile Lys Thr Asn
305
```

<210> SEQ ID NO 16
<211> LENGTH: 921
<212> TYPE: DNA
<213> ORGANISM: Artificial
<220> FEATURE:
<223> OTHER INFORMATION: synthetic

<400> SEQUENCE: 16

```
atggccatcc tggacctcaa gtccctcgtg ctcgacgcca tcaactactg gggccctaag    60
aacaacaacg gcatccaggg ctacaacttc aactacccga tctctgagcg ccagatcgac   120
actagcatca ttactagcac ccactctagg ctcatgcccc acgacctgac catcccgcag   180
aatctggaga ctatcttcac cactacccag gtgctgacca caataccga cgttcagcaa    240
tcgcaaactg tgagcttcag caagaagacc actaccacaa ctagcacgtc aaccacagat   300
ggctggacag agggcggtag gatctccgat accctggaag agaacgttag cgtgagtatt   360
ccgtttatcg gtgcgggcgg tgctaagaac tctacgacca tcgaggcgaa cgtcgcgcat   420
aactcttcga caacgacctc ccagcaagcg tccaccgaga tagagtggaa catctcacag   480
ccagttctgg tgccgcctag gaaacaggtt gtggcgacgc ttgtcatcat gggcggggac   540
ttcaccgtgc ctatggacct cattactacc atcgacagta cccagcactt caccggctac   600
ccaattctta cgtggatcga gaatcccgaa cacaacgtca ggggccgctt cctctcctgg   660
ttcttcgcca attggccaaa cctccctagt gagttcggtt ccctcaactc ggataacacg   720
atcacttaca agggctccgt cgtttccgt attagcgccg ggtgtacgc tactgtccgc     780
ttcgatcagt atgctatcaa taacctccgt actattgaga agacgtggta tgctcggcat   840
ggcacgctgc acaatggaaa gaagatttcc atcaataacg tcacagaaat ggcacccacg   900
agcccgattg agcggaactg a                                             921
```

<210> SEQ ID NO 17
<211> LENGTH: 921
<212> TYPE: DNA
<213> ORGANISM: artificial
<220> FEATURE:
<223> OTHER INFORMATION: synthetic

<400> SEQUENCE: 17

```
atggctatcc tcgatcttaa gtctctagtt cttgatgcta tcaactactg gggccctaag    60
aacaacaacg gaatccaggg atacaacttc aactacccta tctctgagag acagatcgac   120
actagcatca ttactagcac tcactctaga cttatgcctc acgatcttac tatccctcag   180
aaccttgaga ctatcttcac taccactcag gttcttacta caatactga tgttcagcaa    240
```

```
tctcagactg tttctttctc taagaagact actaccacta cttctacctc taccacagat    300
ggatggaccg agggtggtag gatctcagat acccttgagg agaacgtttc agtttcaatc    360
cctttcatcg gagctggtgg tgctaagaac tcaaccacaa tcgaggctaa cgttgctcac    420
aactcatcca ccacaacctc caacaggca tccaccgaga tcgagtggaa cattagccaa    480
cctgtcctcg tcccaccgcg taagcaagtc gtggcaaccc tcgtcattat gggtggcgac    540
ttcaccgtcc caatggacct cattaccaca attgactcca cacaacactt caccggctac    600
ccaattctta catggattga gaacccagaa cataacgtgc gcggtcgatt cttgagctgg    660
ttctttgcaa actggccaaa cttgccgagc gaatttggta gtttgaatag tgacaacaca    720
attacataca agggtagtgt ggttagtcgt atttcggctg gcgtgtacgc cacagtgcgt    780
ttcgaccaat acgccatcaa caatcttcgc acgattgaaa agacgtggta tgcgcgacat    840
gggacgctgc ataatgggaa gaaaatctcg ataaacaatg taacgaaaat ggccccgacg    900
tcgcccatag aacggaattg a                                              921

<210> SEQ ID NO 18
<211> LENGTH: 921
<212> TYPE: DNA
<213> ORGANISM: artificial
<220> FEATURE:
<223> OTHER INFORMATION: synthetic

<400> SEQUENCE: 18
atggctatcc ttgacttgaa gtcccttgtc ctcgacgcta tcaactactg ggcccgaag    60 aacaacaacg gcatccaagg atacaacttc aactacccaa tctctgagag acagattgac    120
actagcatta tcacttctac ccacagtaga ttgatgcctc acgatcttac catacctcag    180
aaccttgaga ccatcttcac cactacccag gtgttgacca caataccga cgtgcagcaa    240 tcccagaccg tgagcttctc caagaagacc actaccacta cctccacctc caccactgac    300
ggctggaccg aaggcggtag gatctccgat accctggagg agaacgtgag cgtgagcatc    360
cccttcatcg gagctggcgg tgccaagaac tccaccacta tcgaggccaa cgtggctcac    420
aactccagca ccactacttc ccagcaagct agtaccgaga tcgaatggaa catctctcag    480
cctgtcctgg tccctccgcg caagcaagtc gttgctactc tcgtcatcat gggcggtgat    540
ttcacggtcc ctatggatct catcacgaca attgatagta cgcagcactt cacgggttac    600
ccgatcctga cgtggattga gaacccggaa cacaatgtca ggggtcgttt cctgtcttgg    660
ttctttgcta actggccgaa ccttccatct gagtttgggt cgcttaactc ggataatacg    720
attacctaca agggatcggt tgtaagtcgt atctcagcag gagtttacgc aacggttaga    780
tttgaccagt atgcgattaa caatttgcgg acaattgaga agacatggta tgcacggcat    840
ggaacactcc ataatggcaa gaaaatcagc atcaacaatg ttacagagat ggctccaaca    900
tcaccaatcg aacgaaactg a                                              921

<210> SEQ ID NO 19
<211> LENGTH: 921
<212> TYPE: DNA
<213> ORGANISM: artificial
<220> FEATURE:
<223> OTHER INFORMATION: synthetic

<400> SEQUENCE: 19
atggccatcc tagaccttaa gagcctcgtg cttgacgcta tcaactattg ggcccgaag    60 aacaacaatg gtatccaggg ctacaacttc aactatccga tctctgagag gcaaatcgac    120
```

```
actagcatca ttactagcac ccattctagg ctcatgccgc acgacttgac catcccgcag      180
aaccttgaga ccatcttcac cacaacccag gtgctgacca caataccga cgtgcagcaa      240 agccagaccg tgagcttcag caagaaaacc acaaccacaa cctccaccag caccacagac      300
ggctggacag agggcgggcg catctccgac acactggagg aaaacgtgag tgtgagtatc      360
cctttcatcg gtgccggtgg agccaagaac tccacaacta tcgaggccaa cgtcgcgcac      420
aactcctcta caactacatc ccagcaagcc tctacagaga tcgagtggaa catctctcag      480
cctgtcctgg tccctccacg caagcaagtc gttgcgactc tggtcattat gggaggcgat      540
ttcactgtcc caatggatct gattactact attgattcta ctcaacactt cactggctac      600
ccaattctta cgtggattga aacccagag cataacgttc gcggacggtt cctttcatgg      660
ttctttgcta actggcccaa tttgccctca gaatttggat cattgaactc agataatacg      720
attacctaca agggttcagt ggtttcgcgg atttcggctg tgtttatgc tacggttaga      780 tttgaccagt atgccatcaa caaccttaga acgatagaaa agacgtggta tgcacgtcat      840
ggtacgttgc ataatgggaa gaaaatctcg ataaacaatg taacggaaat ggcacccacg      900
tcgcccatag aacgaaattg a                                               921
```

<210> SEQ ID NO 20
<211> LENGTH: 2092
<212> TYPE: DNA
<213> ORGANISM: Artificial
<220> FEATURE:
<223> OTHER INFORMATION: synthetic

<400> SEQUENCE: 20

```
ggtccgattg agacttttca acaaagggta atatccggaa acctcctcgg attccattgc       60
ccagctatct gtcactttat tgtgaagata gtggaaaagg aaggtggctc ctacaaatgc      120
catcattgcg ataaaggaaa ggccatcgtt gaagatgcct ctgccgacag tggtcccaaa      180
gatggacccc cacccacgag gagcatcgtg gaaaagaag acgttccaac cacgtcttca      240
aagcaagtgg attgatgtga tggtccgatt gagacttttc aacaaagggt aatatccgga      300
aacctcctcg gattccattg cccagctatc tgtcacttta ttgtgaagat agtggaaaag      360
gaaggtggct cctacaaatg ccatcattgc gataaaggaa aggccatcgt tgaagatgcc      420
tctgccgaca gtggtcccaa agatggaccc ccacccacga ggagcatcgt ggaaaagaa      480 gacgttccaa ccacgtcttc aaagcaagtg gattgatgtg atatctccac tgacgtaagg      540
gatgacgcac aatcccacta tccttcgcaa gacccttcct ctatataagg aagttcattt      600
catttggaga ggacacagaa acattcgcaa aaacaaaatc ccagtatcaa aattcttctc      660
tttttttcat atttcgcaaa gatttaaaaa gatctgctag aaataatttt gtttaacttt      720
aagaaggaga tatatccatg gcgcaagtta gcagaatctg caatggtgtg cagaacccat      780
ctcttatctc caatctctcg aaatccagtc aacgcaaatc tcccttatcg gtttctctga      840
agacgcagca gcatccacga gcttatccga tttcgtcgtc gtggggattg aagaagagtg      900
ggatgacgtt aattggctct gagcttcgtc ctcttaaggt catgtcttct gtttccacgg      960
cgtgcatggc catcctggac ctcaagtccc tcgtgctcga cgccatcaac tactgggcc     1020 ctaagaacaa caacggcatc cagggctaca acttcaacta cccgatctct gagcgccaga     1080
tcgacactag catcattact agcacccact ctaggctcat gccccacgac ctgaccatcc     1140
cgcagaatct ggagactatc ttcaccacta cccaggtgct gaccaacaat accgacgttc     1200
```

-continued

| | |
|---|---|
| agcaatcgca aactgtgagc ttcagcaaga agaccactac cacaactagc acgtcaacca | 1260 |
| cagatggctg gacagagggc ggtaggatct ccgataccct ggaagagaac gttagcgtga | 1320 |
| gtattccgtt tatcggtgcg ggcggtgcta agaactctac gaccatcgag gcgaacgtcg | 1380 |
| cgcataactc ttcgacaacg acctcccagc aagcgtccac cgagatagag tggaacatct | 1440 |
| cacagccagt tctggtgccg cctaggaaac aggttgtggc gacgcttgtc atcatgggcg | 1500 |
| gggacttcac cgtgcctatg gacctcatta ctaccatcga cagtacccag cacttcaccg | 1560 |
| gctacccaat tcttacgtgg atcgagaatc ccgaacacaa cgtcagggcc cgcttcctct | 1620 |
| cctggttctt cgccaattgg ccaaacctcc ctagtgagtt cggttccctc aactcggata | 1680 |
| acacgatcac ttacaagggc tccgtcgttt cccgtattag cgccggggtg tacgctactg | 1740 |
| tccgcttcga tcagtatgct atcaataacc tccgtactat tgagaagacg tggtatgctc | 1800 |
| ggcatggcac gctgcacaat ggaaagaaga tttccatcaa taacgtcaca gaaatggcac | 1860 |
| ccacgagccc gattgagcgg aactgaggat ccaaatcacc agtctctctc tacaaatcta | 1920 |
| tctctctcta tttttctcca gaataatgtg tgagtagttc ccagataagg gaattagggt | 1980 |
| tcttataggg tttcgctcat gtgttgagca tataagaaac ccttagtatg tatttgtatt | 2040 |
| tgtaaaatac ttctatcaat aaaatttcta attcctaaaa ccaaaatcca gt | 2092 |

<210> SEQ ID NO 21
<211> LENGTH: 2092
<212> TYPE: DNA
<213> ORGANISM: Artificial
<220> FEATURE:
<223> OTHER INFORMATION: synthetic

<400> SEQUENCE: 21

| | |
|---|---|
| ggtccgattg agacttttca acaaagggta atatccggaa acctcctcgg attccattgc | 60 |
| ccagctatct gtcactttat tgtgaagata gtggaaaagg aaggtggctc ctacaaatgc | 120 |
| catcattgcg ataaaggaaa ggccatcgtt gaagatgcct ctgccgacag tggtcccaaa | 180 |
| gatggacccc cacccacgag gagcatcgtg gaaaagaag acgttccaac cacgtcttca | 240 |
| aagcaagtgg attgatgtga tggtccgatt gagacttttc aacaaagggt aatatccgga | 300 |
| aacctcctcg gattccattg cccagctatc tgtcacttta ttgtgaagat agtggaaaag | 360 |
| gaaggtggct cctacaaatg ccatcattgc gataaaggaa aggccatcgt tgaagatgcc | 420 |
| tctgccgaca gtggtcccaa agatggaccc ccacccacga ggagcatcgt ggaaaagaa | 480 |
| gacgttccaa ccacgtcttc aaagcaagtg gattgatgtg atatctccac tgacgtaagg | 540 |
| gatgacgcac aatcccacta tccttcgcaa gacccttcct ctatataagg aagttcattt | 600 |
| catttggaga ggacacagaa acattcgcaa aaacaaaatc ccagtatcaa aattcttctc | 660 |
| ttttttttcat atttcgcaaa gatttaaaaa gatctgctag aaataatttt gtttaacttt | 720 |
| aagaaggaga tatatccatg cgcaagtta gcagaatctg caatggtgtg cagaacccat | 780 |
| ctcttatctc caatctctcg aaatccagtc aacgcaaatc tcccttatcg gtttctctga | 840 |
| agacgcagca gcatccacga gcttatccga tttcgtcgtc gtggggattg aagaagagtg | 900 |
| ggatgacgtt aattggctct gagcttcgtc ctcttaaggt catgtcttct gtttccacgg | 960 |
| cgtgcatggc tatcctcgat cttaagtctc tagttcttga tgctatcaac tactggggcc | 1020 |
| ctaagaacaa caacggaatc cagggataca acttcaacta ccctatctct gagagacaga | 1080 |
| tcgacactag catcattact agcactcact ctagacttat gcctcacgat cttactatcc | 1140 |
| ctcagaacct tgagactatc ttcactacca ctcaggttct tactaacaat actgatgttc | 1200 |

```
agcaatctca gactgtttct ttctctaaga agactactac cactacttct acctctacca   1260
cagatggatg gaccgagggt ggtaggatct cagatacect tgaggagaac gtttcagttt   1320 caatccettt catcggagct ggtggtgcta agaactcaac cacaatcgag gctaacgttg   1380
ctcacaactc atccaccaca acctcccaac aggcatccac cgagatcgag tggaacatta   1440
gccaacctgt cctcgtccca ccgcgtaagc aagtcgtggc aaccctcgtc attatgggtg   1500
gcgacttcac cgtcccaatg gacctcatta ccacaattga ctccacacaa cacttcaccg   1560
gctacccaat tcttacatgg attgagaacc cagaacataa cgtgcgcggt cgattcttga   1620
gctggttctt tgcaaactgg ccaaacttgc cgagcgaatt tggtagtttg aatagtgaca   1680
acacaattac atacaagggt agtgtggtta gtcgtatttc ggctggcgtg tacgccacag   1740
tgcgtttcga ccaatacgcc atcaacaatc ttcgcacgat tgaaaagacg tggtatgcgc   1800
gacatgggac gctgcataat gggaagaaaa tctcgataaa caatgtaacg gaaatggccc   1860
cgacgtcgcc catagaacgg aattgaggat ccaaatcacc agtctctctc tacaaatcta   1920
tctctctcta ttttctccca gaataatgtg tgagtagttc ccagataagg gaattagggt   1980
tcttataggg tttcgctcat gtgttgagca tataagaaac ccttagtatg tatttgtatt   2040
tgtaaaatac ttctatcaat aaaatttcta attcctaaaa ccaaaatcca gt           2092
```

<210> SEQ ID NO 22
<211> LENGTH: 2092
<212> TYPE: DNA
<213> ORGANISM: Artificial
<220> FEATURE:
<223> OTHER INFORMATION: synthetic

<400> SEQUENCE: 22

```
ggtccgattg agacttttca acaaagggta atatccggaa acctcctcgg attccattgc     60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg gaaaaagaag acgttccaac cacgtcttca    240
aagcaagtgg attgatgtga tggtccgatt gagacttttc aacaaagggt aatatccgga    300
aacctcctcg gattccattg cccagctatc tgtcactttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga ggacacagaa acattcgcaa aaacaaaatc ccagtatcaa aattcttctc    660 ttttttttcat atttcgcaaa gatttaaaaa gatctgctag aaataatttt gtttaacttt    720
aagaaggaga tatatccatg cgcaagtta gcagaatctg caatggtgtg cagaacccat    780
ctcttatctc caatctctcg aaatccagtc aacgcaaatc tcccttatcg gtttctctga    840
agacgcagca gcatccacga gcttatccga tttcgtcgtc gtggggattg aagaagagtg    900
ggatgacgtt aattggctct gagcttcgtc ctcttaaggt catgtcttct gtttccacgg    960
cgtgcatggc tatccttgac ttgaagtccc ttgtcctcga cgctatcaac tactggggcc   1020
cgaagaacaa caacggcatc caaggataca acttcaacta cccaatctct gagagacaga   1080
ttgacactag cattatcact tctacccaca gtagattgat gcctcacgat cttaccatac   1140
```

| | |
|---|---|
| ctcagaacct tgagaccatc ttcaccacta cccaggtgtt gaccaacaat accgacgtgc | 1200 |
| agcaatccca daccgtgagc ttctccaaga agaccactac cactacctcc acctccacca | 1260 |
| ctgacggctg gaccgaaggc ggtaggatct ccgataccct ggaggagaac gtgagcgtga | 1320 |
| gcatcccctt catcggagct ggcggtgcca agaactccac cactatcgag gccaacgtgg | 1380 |
| ctcacaactc cagcaccact acttcccagc aagctagtac cgagatcgaa tggaacatct | 1440 |
| ctcagcctgt cctggtccct ccgcgcaagc aagtcgttgc tactctcgtc atcatgggcg | 1500 |
| gtgatttcac ggtccctatg gatctcatca cgacaattga tagtacgcag cacttcacgg | 1560 |
| gttacccgat cctgacgtgg attgagaacc cggaacacaa tgtcagggg cgtttcctgt | 1620 |
| cttggttctt tgctaactgg ccgaaccttc catctgagtt tgggtcgctt aactcggata | 1680 |
| atacgattac ctacaaggga tcggttgtaa gtcgtatctc agcaggagtt tacgcaacgg | 1740 |
| ttagatttga ccagtatgcg attaacaatt tgcggacaat tgagaagaca tggtatgcac | 1800 |
| ggcatggaac actccataat ggcaagaaaa tcagcatcaa caatgttaca gagatggctc | 1860 |
| caacatcacc aatcgaacga aactgaggat ccaaatcacc agtctctctc tacaaatcta | 1920 |
| tctctctcta ttttctcca gaataatgtg tgagtagttc ccagataagg gaattagggt | 1980 |
| tcttataggg tttcgctcat gtgttgagca tataagaaac ccttagtatg tatttgtatt | 2040 |
| tgtaaaatac ttctatcaat aaaatttcta attcctaaaa ccaaaatcca gt | 2092 |

<210> SEQ ID NO 23
<211> LENGTH: 2092
<212> TYPE: DNA
<213> ORGANISM: Artificial
<220> FEATURE:
<223> OTHER INFORMATION: synthetic

<400> SEQUENCE: 23

| | |
|---|---|
| ggtccgattg agacttttca acaaagggta atatccggaa acctcctcgg attccattgc | 60 |
| ccagctatct gtcactttat tgtgaagata gtggaaaagg aaggtggctc ctacaaatgc | 120 |
| catcattgcg ataaaggaaa ggccatcgtt gaagatgcct ctgccgacag tggtcccaaa | 180 |
| gatggacccc cacccacgag gagcatcgtg gaaaaagaag acgttccaac cacgtcttca | 240 |
| aagcaagtgg attgatgtga tggtccgatt gagactttt aacaaagggt aatatccgga | 300 |
| aacctcctcg gattccattg cccagctatc tgtcactta ttgtgaagat agtggaaaag | 360 |
| gaaggtggct cctacaaatg ccatcattgc gataaaggaa aggccatcgt tgaagatgcc | 420 |
| tctgccgaca gtggtcccaa agatggaccc cacccacga ggagcatcgt ggaaaaagaa | 480 |
| gacgttccaa ccacgtcttc aaagcaagtg gattgatgtg atatctccac tgacgtaagg | 540 |
| gatgacgcac aatcccacta tccttcgcaa gacccttcct ctatataagg aagttcattt | 600 |
| catttggaga ggacacagaa acattcgcaa aaacaaaatc ccagtatcaa aattcttctc | 660 |
| ttttttcat atttcgcaaa gatttaaaa gatctgctag aaataatttt gtttaacttt | 720 |
| aagaaggaga tatatccatg gcgcaagtta gcagaatctg caatggtgtg cagaacccat | 780 |
| ctcttatctc caatctctcg aaatccagtc aacgcaaatc tcccttatcg gtttctctga | 840 |
| agacgcagca gcatccacga gcttatccga tttgtcgtc gtgggattg aagaagagtg | 900 |
| ggatgacgtt aattggctct gagcttcgtc tctttaaggt catgtctcct gtttccacgg | 960 |
| cgtgcatggc catcctagac cttaagagcc tcgtgcttga cgctatcaac tattgggccc | 1020 |
| cgaagaacaa caatggtatc cagggctaca acttcaacta tccgatctct gagaggcaaa | 1080 |
| tcgacactag catcattact agcaccccaтт ctaggctcat gccgcacgac ttgaccatcc | 1140 |

-continued

```
cgcagaacct tgagaccatc ttcaccacaa cccaggtgct gaccaacaat accgacgtgc    1200
agcaaagcca gaccgtgagc ttcagcaaga aaaccacaac cacaacctcc accagcacca    1260
cagacggctg gacagagggc gggcgcatct ccgacacact ggaggaaaac gtgagtgtga    1320
gtatcccttt catcggtgcc ggtggagcca agaactccac aactatcgag gccaacgtcg    1380
cgcacaactc ctctacaact acatcccagc aagcctctac agagatcgag tggaacatct    1440
ctcagcctgt cctggtccct ccacgcaagc aagtcgttgc gactctggtc attatgggag    1500
gcgatttcac tgtcccaatg gatctgatta ctactattga ttctactcaa cacttcactg    1560
gctacccaat tcttacgtgg attgagaacc agagcataa cgttcgcgga cggttccttt     1620
catggttctt tgctaactgg cccaatttgc cctcagaatt tggatcattg aactcagata    1680
atacgattac ctacaagggt tcagtggttt cgcggatttc ggctggtgtt tatgctacgg    1740
ttagatttga ccagtatgcc atcaacaacc ttagaacgat agaaaagacg tggtatgcac    1800
gtcatggtac gttgcataat gggaagaaaa tctcgataaa caatgtaacg gaaatggcac    1860
ccacgtcgcc catagaacga aattgaggat ccaaatcacc agtctctctc tacaaatcta    1920
tctctctcta tttttctcca gaataatgtg tgagtagttc ccagataagg gaattagggt    1980
tcttataggg tttcgctcat gtgttgagca tataagaaac ccttagtatg tatttgtatt    2040
tgtaaaatac ttctatcaat aaaatttcta attcctaaaa ccaaaatcca gt            2092
```

<210> SEQ ID NO 24
<211> LENGTH: 1864
<212> TYPE: DNA
<213> ORGANISM: Artificial
<220> FEATURE:
<223> OTHER INFORMATION: synthetic

<400> SEQUENCE: 24

```
ggtccgattg agactttca acaaagggta atatccggaa acctcctcgg attccattgc      60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg aaaaagaag acgttccaac cacgtcttca    240
aagcaagtgg attgatgtga tggtccgatt gagactttc aacaaagggt aatatccgga    300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc cacccacga ggagcatcgt ggaaaagaa     480 gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga ggacacagaa acattcgcaa aaacaaaatc ccagtatcaa aattcttctc    660 ttttttttcat atttcgcaaa gatttaaaaa gatctgctag aaataatttt gtttaacttt    720
aagaaggaga tatatccatg gccatcctgg acctcaagtc cctcgtgctc gacgccatca    780
actactgggg ccctaagaac aacaacggca tccagggcta caacttcaac tacccgatct    840
ctgagcgcca gatcgacact agcatcatta ctagcaccca ctctaggctc atgccccacg    900
acctgaccat cccgcagaat ctggagacta tcttcaccac tacccaggtg ctgaccaaca    960
ataccgacgt tcagcaatcg caaactgtga gcttcagcaa gagaccact accacaacta   1020 gcacgtcaac cacagatggc tggacagagg gcggtaggat ctccgatacc ctggaagaga   1080
```

| | |
|---|---|
| acgttagcgt gagtattccg tttatcggtg cgggcggtgc taagaactct acgaccatcg | 1140 |
| aggcgaacgt cgcgcataac tcttcgacaa cgacctccca gcaagcgtcc accgagatag | 1200 |
| agtggaacat ctcacagcca gttctggtgc cgcctaggaa acaggttgtg gcgacgcttg | 1260 |
| tcatcatggg cggggacttc accgtgccta tggacctcat tactaccatc gacagtaccc | 1320 |
| agcacttcac cggctaccca attcttacgt ggatcgagaa tcccgaacac aacgtcaggg | 1380 |
| gccgcttcct ctcctggttc ttcgccaatt ggccaaacct ccctagtgag ttcggttccc | 1440 |
| tcaactcgga taacacgatc acttacaagg gctccgtcgt ttcccgtatt agcgccgggg | 1500 |
| tgtacgctac tgtccgcttc gatcagtatg ctatcaataa cctccgtact attgagaaga | 1560 |
| cgtggtatgc tcggcatggc acgctgcaca atggaaagaa gatttccatc aataacgtca | 1620 |
| cagaaatggc acccacgagc ccgattgagc ggaactgagg atccaaatca ccagtctctc | 1680 |
| tctacaaatc tatctctctc tattttctc cagaataatg tgtgagtagt tcccagataa | 1740 |
| gggaattagg gttcttatag ggtttcgctc atgtgttgag catataagaa acccttagta | 1800 |
| tgtatttgta tttgtaaaat acttctatca ataaatttc taattcctaa aaccaaaatc | 1860 |
| cagt | 1864 |

<210> SEQ ID NO 25
<211> LENGTH: 1864
<212> TYPE: DNA
<213> ORGANISM: Artificial
<220> FEATURE:
<223> OTHER INFORMATION: synthetic

<400> SEQUENCE: 25

| | |
|---|---|
| ggtccgattg agacttttca acaaagggta atatccggaa acctcctcgg attccattgc | 60 |
| ccagctatct gtcactttat tgtgaagata gtggaaaagg aaggtggctc ctacaaatgc | 120 |
| catcattgcg ataaaggaaa ggccatcgtt gaagatgcct ctgccgacag tggtcccaaa | 180 |
| gatggacccc cacccacgag gagcatcgtg aaaaagaag acgttccaac cacgtcttca | 240 |
| aagcaagtgg attgatgtga tggtccgatt gagacttttc aacaaagggt aatatccgga | 300 |
| aacctcctcg gattccattg cccagctatc tgtcacttta ttgtgaagat agtggaaaag | 360 |
| gaaggtggct cctacaaatg ccatcattgc gataaaggaa aggccatcgt tgaagatgcc | 420 |
| tctgccgaca gtggtcccaa agatggaccc ccacccacga ggagcatcgt ggaaaaagaa | 480 |
| gacgttccaa ccacgtcttc aaagcaagtg gattgatgtg atatctccac tgacgtaagg | 540 |
| gatgacgcac aatcccacta tccttcgcaa gacccttcct ctatataagg aagttcattt | 600 |
| catttggaga ggacacagaa acattcgcaa aaacaaaatc ccagtatcaa aattcttctc | 660 |
| ttttttttcat atttcgcaaa gatttaaaaa gatctgctag aaataatttt gtttaacttt | 720 |
| aagaaggaga tatatccatg gctatcctcg atcttaagtc tctagttctt gatgctatca | 780 |
| actactgggg ccctaagaac aacaacgaa tccagggata caacttcaac taccctatct | 840 |
| ctgagagaca gatcgacact agcatcatta ctagcactca ctctagactt atgcctcacg | 900 |
| atcttactat ccctcagaac cttgagacta tcttcactac cactcaggtt cttactaaca | 960 |
| atactgatgt tcagcaatct cagactgttt ctttctctaa gaagactact accactactt | 1020 |
| ctacctctac cacagatgga tggaccgagg gtggtaggat ctcagatacc cttgaggaga | 1080 |
| acgtttcagt ttcaatccct ttcatcggag ctggtggtgc taagaactca accacaatcg | 1140 |
| aggctaacgt tgctcacaac tcatccacca caacctccca acaggcatcc accgagatcg | 1200 |
| agtggaacat tagccaacct gtcctcgtcc caccgcgtaa gcaagtcgtg gcaaccctcg | 1260 |

```
tcattatggg tggcgacttc accgtcccaa tggacctcat taccacaatt gactccacac   1320
aacacttcac cggctaccca attcttacat ggattgagaa cccagaacat aacgtgcgcg   1380
gtcgattctt gagctggttc tttgcaaact ggccaaactt gccgagcgaa tttggtagtt   1440
tgaatagtga caacacaatt acatacaagg gtagtgtggt tagtcgtatt tcggctggcg   1500
tgtacgccac agtgcgtttc gaccaatacg ccatcaacaa tcttcgcacg attgaaaaga   1560
cgtggtatgc gcgacatggg acgctgcata atgggaagaa aatctcgata aacaatgtaa   1620
cggaaatggc cccgacgtcg cccatagaac ggaattgagg atccaaatca ccagtctctc   1680
tctacaaatc tatctctctc tattttctc cagaataatg tgtgagtagt tcccagataa   1740
gggaattagg gttcttatag ggtttcgctc atgtgttgag catataagaa acccttagta   1800
tgtatttgta tttgtaaaat acttctatca ataaaatttc taattcctaa aaccaaaatc   1860
cagt                                                                1864

<210> SEQ ID NO 26
<211> LENGTH: 1864
<212> TYPE: DNA
<213> ORGANISM: Artificial
<220> FEATURE:
<223> OTHER INFORMATION: synthetic

<400> SEQUENCE: 26
ggtccgattg agacttttca acaaagggta atatccggaa acctcctcgg attccattgc     60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg aaaaagaag acgttccaac cacgtcttca    240
aagcaagtgg attgatgtga tggtccgatt gagacttttc aacaaagggt aatatccgga    300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga ggacacagaa acattcgcaa aaacaaaatc ccagtatcaa aattcttctc    660
tttttttcat atttcgcaaa gatttaaaaa gatctgctag aaataatttt gtttaacttt    720
aagaaggaga tatatccatg gctatccttg acttgaagtc ccttgtcctc gacgctatca    780
actactgggg cccgaagaac aacaacggca tccaaggata caacttcaac tacccaatct    840
ctgagagaca gattgacact agcattatca cttctaccca cagtagattg atgcctcacg    900
atcttaccat acctcagaac cttgagacca tcttcaccac tacccaggtg ttgaccaaca    960
ataccgacgt gcagcaatcc cagaccgtga gcttctccaa gagaccact accactacct  1020 ccacctccac cactgacggc tggaccgaag gcggtaggat ctccgatacc ctggaggaga  1080
acgtgagcgt gagcatcccc ttcatcggag ctggcggtgc caagaactcc accactatcg  1140
aggccaacgt ggctcacaac tccagcacca ctacttccca gcaagctagt accgagatcg  1200
aatggaacat ctctcagcct gtcctggtcc ctccgcgcaa gcaagtcgtt gctactctcg  1260
tcatcatggg cggtgatttc acggtcccta tggatctcat cacgacaatt gatagtacgc  1320
agcacttcac gggttacccg atcctgacgt ggattgagaa cccggaacac aatgtcaggg  1380
```

| | |
|---|---:|
| gtcgtttcct gtcttggttc tttgctaact ggccgaacct tccatctgag tttgggtcgc | 1440 |
| ttaactcgga taatacgatt acctacaagg gatcggttgt aagtcgtatc tcagcaggag | 1500 |
| tttacgcaac ggttagattt gaccagtatg cgattaacaa tttgcggaca attgagaaga | 1560 |
| catggtatgc acggcatgga acactccata atggcaagaa atcagcatc aacaatgtta | 1620 |
| cagagatggc tccaacatca ccaatcgaac gaaactgagg atccaaatca ccagtctctc | 1680 |
| tctacaaatc tatctctctc tattttctc cagaataatg tgtgagtagt tcccagataa | 1740 |
| gggaattagg gttcttatag ggtttcgctc atgtgttgag catataagaa acccttagta | 1800 |
| tgtatttgta tttgtaaaat acttctatca ataaaatttc taattcctaa aaccaaaatc | 1860 |
| cagt | 1864 |

<210> SEQ ID NO 27
<211> LENGTH: 1864
<212> TYPE: DNA
<213> ORGANISM: Artificial
<220> FEATURE:
<223> OTHER INFORMATION: synthetic

<400> SEQUENCE: 27

| | |
|---|---:|
| ggtccgattg agacttttca acaaagggta atatccggaa acctcctcgg attccattgc | 60 |
| ccagctatct gtcactttat tgtgaagata gtggaaaagg aaggtggctc ctacaaatgc | 120 |
| catcattgcg ataaaggaaa ggccatcgtt gaagatgcct ctgccgacag tggtcccaaa | 180 |
| gatggacccc cacccacgag gagcatcgtg gaaaagaag acgttccaac cacgtcttca | 240 |
| aagcaagtgg attgatgtga tggtccgatt gagacttttc aacaagggt aatatccgga | 300 |
| aacctcctcg gattccattg cccagctatc tgtcactta ttgtgaagat agtggaaaag | 360 |
| gaaggtggct cctacaaatg ccatcattgc gataaaggaa aggccatcgt tgaagatgcc | 420 |
| tctgccgaca gtggtcccaa agatggaccc ccacccacga ggagcatcgt ggaaaagaa | 480 |
| gacgttccaa ccacgtcttc aaagcaagtg gattgatgtg atatctccac tgacgtaagg | 540 |
| gatgacgcac aatcccacta tccttcgcaa gacccttcct ctatataagg aagttcattt | 600 |
| catttggaga ggacacagaa acattcgcaa aaacaaaatc ccagtatcaa aattcttctc | 660 |
| ttttttttcat atttcgcaaa gatttaaaaa gatctgctag aaataatttt gtttaacttt | 720 |
| aagaaggaga tatatccatg gccatcctag accttaagag cctcgtgctt gacgctatca | 780 |
| actattgggg cccgaagaac aacaatggta tccagggcta caacttcaac tatccgatct | 840 |
| ctgagaggca aatcgacact agcatcatta ctagcaccca ttctaggctc atgccgcacg | 900 |
| acttgaccat cccgcagaac cttgagacca tcttcaccac aaccccaggtg ctgaccaaca | 960 |
| ataccgacgt gcagcaaagc cagaccgtga gcttcagcaa gaaaaccaca accacaacct | 1020 |
| ccaccagcac cacagacggc tggacagagg gcgggcgcat ctccgacaca ctggaggaaa | 1080 |
| acgtgagtgt gagtatccct ttcatcggtg ccggtggagc caagaactcc acaactatcg | 1140 |
| aggccaacgt cgcgcacaac tcctctacaa ctacatccca gcaagcctct acagagatcg | 1200 |
| agtggaacat ctctcagcct gtcctggtcc ctccacgcaa gcaagtcgtt gcgactctgg | 1260 |
| tcattatggg aggcgatttc actgtcccaa tggatctgat tactactatt gattctactc | 1320 |
| aacacttcac tggctaccca attcttacgt ggattgagaa cccagagcat aacgttcgcg | 1380 |
| gacggttcct ttcatggttc tttgctaact ggcccaattt gccctcagaa tttggatcat | 1440 |
| tgaactcaga taatacgatt acctacaagg gttcagtggt ttcgcggatt tcggctggtg | 1500 |
| tttatgctac ggttagattt gaccagtatg ccatcaacaa ccttagaacg atagaaaaga | 1560 |

```
cgtggtatgc acgtcatggt acgttgcata atgggaagaa aatctcgata aacaatgtaa    1620
cggaaatggc acccacgtcg cccatagaac gaaattgagg atccaaatca ccagtctctc    1680
tctacaaatc tatctctctc tatttttctc cagaataatg tgtgagtagt tcccagataa    1740
gggaattagg gttcttatag ggtttcgctc atgtgttgag catataagaa acccttagta    1800
tgtatttgta tttgtaaaat acttctatca ataaaatttc taattcctaa aaccaaaatc    1860
cagt                                                                 1864

<210> SEQ ID NO 28
<211> LENGTH: 1919
<212> TYPE: DNA
<213> ORGANISM: Lygus hesperus

<400> SEQUENCE: 28
acacccccag ggtccccatt gttgttcagc cgtttgaaag gagtcagcaa acagcgggct      60
ttcttcttag gagatttgcg tccgtcggac cggcacaccc ccagggtccc cattttgttc    120
agtgtttgaa aggagtcagc aaacagcggc aagatgtgtg acgacgatgt agcggcgctc    180
gtagtcgaca acggctcagg aatgtgcaag gcgggcttcg ccggagatga cgctcccagg    240
gctgtcttcc cctccatcgt cggccgcccc aggcatcagg gtgtgatggt cggtatgggt    300
caaaaggact cctacgtcgg cgacgaggct cagagcaaga gaggtatcct cactctgaag    360
taccccatcg agcacggcat catcaccaac tgggacgaca tggagaagat ctggcaccac    420
accttctaca cgagctccg cgtcgctccc gaggagcacc ccatcctcct cacggaggct    480
cccctcaacc ccaaagccaa cagggagaag atgactcaga tcatgtttga gaccttcaac    540 accccgcca tgtacgtcgc catccaggcc gtccttccc tctacgcttc cggtcgtacc      600
accggtatcg tcctcgactc cggagatggt gtctcccaca ccgtccccat ctatgaaggt    660
tacgcccttc ctcacgccat cctccgtctg gacttggctg gcgtgacttt gactgactac    720
ctgatgaaga tcctcaccga gaggggttac tctttcacca ccaccgctga gagggaaatc    780
gtccgcgaca tcaaggagaa gctctgctac gtcgctctgg acttcgagca ggaaatggcc    840 accgcgccg cctccacctc cctcgagaag tcctacgagc ttcccgacgg acaggtcatc    900
accatcggca acgagaggtt ccgttgcccc gaagccctct tccagccttc cttcctgggt    960
atggaatcct gcggtatcca cgagaccgtc tacaactcca tcatgaagtg cgacgtcgac   1020
atcaggaaag acctgtacgc caacaccgtc ctctccggag gcaccaccat gtaccccggt   1080
atcgccgaca ggatgcagaa ggaaatcacc gccctcgctc cctcgaccat caagatcaag   1140
atcatcgctc ccccagaaag gaagtactcc gtatggatcg gtggctccat cctcgcctcc   1200
ctctccacct ccaacagat gtggatctcc aagcaggagt acgacgagtc cggccccggc   1260
atcgtccacc gcaagtgctt ctaagcgaaa cactcaccac atcaatacac cactacatca   1320
aaccacacaa gacgcgccag ttacaatcgg gaccgtggtg ggcgcgtctt gttgtggttt   1380 gatgccccc cccccccccc cacccccac ctaaaaatcc caggggctcc ctcgagaaag   1440
tcctacgagc tttcccgacg tcaccatcgc gaaaggtccc ccccctgtg gaattggcct   1500 ccccgtcga ctaccatcat gtctgccaac tatcgacacc ctcgacgtgg acaatatcat   1560
tactggcgtc ctctactctt acgctattgc gcccactatt ctagtccatt gctactccat   1620
taatagagat ctacttcatt gtccatacta tatacactac tattttttac atacttactg   1680
ctcacttatt attgagtttc aattttacat attcgtttaa tacattatgc agatcttatt   1740
```

```
ctccaactag tttcgcgtag tggcttttcg gggtgaaata ggtgcgtatt gctggacttg    1800
aggtgttgtc acgctatact gttttcttgc actattctat cggtaggtag gagtcagttt    1860
cggcattttt attgttcatg cctcattcat attcatgtta tttaaatcgt gataggtga     1919
```

<210> SEQ ID NO 29
<211> LENGTH: 991
<212> TYPE: DNA
<213> ORGANISM: Lygus hesperus

<400> SEQUENCE: 29

```
acaaacgctt tgcagtgagg aaggtggaag gaactgaaaa tatatcttga aggagtttaa      60
catcatacaa ggtgatttca tctcgtgtca acggtacctg catctatcgg tgagatgatt     120
tacttaattt tggctctggc cataatatgg gccttcgtga aactctacac gcaggtcttc     180
aattactggg agcaacgagg gtttccgtac gtggaaggga aattccctct tggcagtgac     240
ccctgcctct ctcgcccgtc caagttcttg ggtttcgaag ttcaggaaca ttacaggaaa     300
cttttcgggg c accctctcgg cgggatatac gtcggcagga gaccagatct catcgtcagg    360 gacccccaaaa taatcaagaa catcatggtc aaagattttg ctcattttcg gaatcgcagt    420
gttgagatcc cttctaaaga caatccactg acacaacact tgttctcgct ggaaggcacg    480
aaatggagag ctctccgagt caagctcaca cctactttca cgtctggcaa gttgaaactg    540
atgtacagcc tattcgtaga atgcgctcaa cgcttggaac gcaaattaaa cgaagattct    600
atgaagaacg aaggggtggt ggatataaag gacaccatcg caaggtttac cactgacata    660
atcggctctt gcgcgttcgg cctagaaatc gacagtctca acaaccccga cgagcccttc    720
aggaaaatcg gaatgcgttt attccgacgt aacctgaaag gaagactcat cgagttgatc    780
tacagtttgg caccgagcct acgaaactac ttgaaactat cgaggacatc caaagagacg    840
gaaaaaatgg tcatgtcggg tatcggccag actatcgaat atcgtgagaa aaacaacgtc    900
cgacgaaatg attttctcga tctcctcatc gagctgaaaa acagggacat tttgtacgtt    960
gatcgacaga aagacagcaa atattgaaaa c                                    991
```

<210> SEQ ID NO 30
<211> LENGTH: 2656
<212> TYPE: DNA
<213> ORGANISM: Lygus hesperus
<220> FEATURE:
<221> NAME/KEY: misc_feature
<222> LOCATION: (1)..(1)
<223> OTHER INFORMATION: n is a, c, g, or t

<400> SEQUENCE: 30

```
nccctttaa agcccccgca cccgaggtgt ttccgtgatc aatattattt catcctattt      60
catctccatt acattcccgt catgcacttg gagaaccact ttgagaccgt ttcttacttt    120
taactaatca accatgggaa aagagaagat tcatatcaac atcgtcgtca ttggacacgt    180
cgactccggc aaatccacga ccaccggaca cttgatctac aaatgcggtg gtatcgacaa    240
gcgtacgatc gagaaattcg agaaggaagc ccaggaaatg ggtaaaggtt ccttcaagta    300
cgcctgggtt ttggacaagc tgaaggccga gcgtgagcgt ggtatcacca tcgatatcgc    360
cctctggaag ttcgaaactg gcaaatacta cgtgaccatc atcgacgccc tggacacag    420 ggatttcatc aagaacatga tcactggaac ctcacaggct gattgcgctg tgctgatcgt    480
agcagccggt accggtgagt tcgaagctgg tatctccaag aacggacaaa cccgagaaca    540
cgcccttctc gccttcaccc tcggtgtgaa acagctcatc gttggtgtga acaagatgga    600
```

```
ctctactgag cccccctaca gcgagaaccg tttcgaggaa atcaaaaagg aagtctcgtc    660
ctacatcaag aagatcggtt acaacccagc ggccgtcgcc ttcgttccca tctccggatg    720
gcacggcgac aacatgttgg aaccctctga caagatgccc tggttcaagg ggtgggccgt    780
cgagaggaag gaaggcaagg ctgacggcaa gtgcctcatc gaagcccctcg acgccatcct    840 cccccccctcc cgccctaccg acaaagccct caggcttccc ctccaggacg tgtacaagat    900
cggcggtatc ggaactgtcc ccgtgggtcg tgttgagacc ggtgtcctga acccggtat     960 ggtcgtcacc ttcgcccccg tcaacctgac cactgaagtc aagtccgtgg agatgcacca    1020
cgaagccctc caggaagccg tgcccggcga acgtcggc ttcaacgtca agaacgtctc      1080
cgtcaaggaa ttgcgtcgag ggtacgtcgc cggagactcc aaggcttctc ctcccaaggc    1140
cgcttccgac ttcaccgcac aggttattgt cctgaaccat cctggacaga tcgccaatgg    1200
ctacacccca gtgttggatt gccacactgc tcacatcgca tgcaaattcc aagacatcaa    1260
ggagaaatgc gaccgtcgta ctggtaaaac caccgaacag aaccccaaat ccatcaagtc    1320
cggtgacgct gccatcatca ccctcgtccc gaccaagccc atgtgcgtcg agtccttcca    1380
ggagttcccc cctcttggac gtttcgctgt gcgtgacatg agacagaccg tcgctgtcgg    1440
tgtcatcaag agcgtcacta acaaggacat caccaccggc aaagtaacga aggccgcaga    1500
gaaggcccag aagaagaaat aactaggtgt catggaatca catacactca tcaaggggaa    1560
ccttggtcgc tattctgtac tctgcccact cctcttgtcc aagtggttgc tccaaccgtg    1620
tttccatcgc aaagagttca gaaggaaaag cggttaaagt caccacttaa ctataatccc    1680
aactttatta tatatatata aatatatagc ctcgacttgt gtacacgttt ttaattaaag    1740
aaggagactg tttattattt ttggttttgt ttttatcatt taaaaaatct atttcttttt    1800
tcgaaaaaaa gaaacgaac ttgggttttt tttttgtatt ttacatctgg tggtataact    1860
gtgccccttt gtcctgtttt gtgtgaaaaa tagcgaattt tgtttttttaa tttattttt    1920 tgcgatttta ttcttcgtca aaataatttt aaaaaaattt atttacagca ttttttaaat    1980
taattgaagc aaaaactata attgacattc tgtatagatt ggtgactaaa taaactcgaa    2040
tgcttcatga aaaaaaaaaa aaagggcgg ccaaaaaaaa aaaaaaaaaa aaaaaaaaaa    2100
aaaaaaaaaa aaaaaaaaaa aaaaaaaaaa aaaaaaaaaa aaaaaaaaaa aaaaaaaaaa    2160
aaaaaaaaaa gggggggggcc cctttaaaaa tcccccgggg gggcccaatt ttcccggacc    2220
cccttttttt tgaaaagggg ggcccctaaa gggggcctat ttaaaagtag ggccggggcc    2280 gcgttttttaa accgcggggg ggggaaaaat ggttatttgg gatttttttgg aaagaacccct  2340 tttttggggg ggggaaata ttgggaaaaa tcccccaaaa aatttaaagg tttaagggaa    2400
aaaaaaaatt tttaagggga aaggggggta aaaaaacttg cttttttttg tggttgaaaa    2460
tttttttttt tgggttttttt tttttaaaaa tttttttccc gggggttggg gttttattg    2520 gttggggttt ttaaaattcc aagcccccagg gttttttttgg ggccccccac cccccaagt    2580 ttgttttgat ttaaaatccc ccaacccaat tttggaaggg gttttttttg tttaaaaaac    2640
cccccccccc ccccc                                                   2656
```

<210> SEQ ID NO 31
<211> LENGTH: 1043
<212> TYPE: DNA
<213> ORGANISM: Lygus hesperus

<400> SEQUENCE: 31

```
gtcctctcgt cttgtttcca gaggaggtgt gaattttagg atgaaatctt tgctggtgct    60
tatgtcagtg gtgggcttgg ccatgtgcca gtggggccag cctggacttc ctcaggacac   120
tcctgaagta gccgctgcca aagctgccca ctacgccgct ctcgccagag ccggtacccc   180
agttcacaac gccgctccca cctggaacgc cgccctgcc tggggaactc ccgccgcccc   240
cggcgtccct caagatacgc ctgaagtcgc cgctgccaag gccgctcatt tcgctgccgt   300
cgctcaggtt cagagccaca cgcctcagca gtcttgggct cctcagcagt cctggactcc   360
ccagagccag cagtggacta gcgagcacca acccaggtgg aacggaccca tcgctctgcc   420
cccgggcttc gaccagaacg cgctcccct ccccgtccaa gacacccctg aagtagctgc   480
tgagcgcgca aggcacttca acctctactc cagcggtgga catccttccc tcgccccgc   540 tcagccttcc tggaacgccg ctcctcaatg aacgccgct cctcagtggt ccgctcccgc   600
tacccagtgg aacgctcaac ccggtctccc tcaggacacc cccgaagtcg ccgctgccaa   660
ggccgctcac ttcgccgctc acgctcaact tgctcctgcc tccaaccacg gtaggtggaa   720
gagaggaatc ctcgctgccc cagtcaccac cgtcagcgcg cactccacct ccatcgtcca   780
ctctgccccc gtggtccacg ccaccccgt cgtccacgca actcccattg ttcgcgctgc   840
tcccgtagtc cacaccttgc cctaccttcg caccctggtc cacaccgccc ccatcgtccc   900
caccgccccc atcgtcccca cccgcccctc tccgcccatc gctccactgg gtaattaatg   960
actggcgaag aagccacgac tgattttttg tgtcgtagtt tacgagcttt gtagaaaaac  1020
gaaaatttga atgaattgat tgg                                          1043

<210> SEQ ID NO 32
<211> LENGTH: 2346
<212> TYPE: DNA
<213> ORGANISM: Lygus hesperus

<400> SEQUENCE: 32
actcgttcta gatcgcgatg gacgcgtggt cgagaaacga gaacgagcta cgttgagcat    60
caagagcttt cgtactattg aaattctcga aaaatcgcag atcttcgtta aaactttcga   120
ctcgggaaga ccatcaccct cgaggtcgag ccttctcgat accattgaaa cgtgaaggc   180 gaaaattcag gataaagaag gcatcccccc agatcagcag aggttgatct tgccggcaa   240 gcagttggaa gacggacgta ctttgtctga ctacaacatc caaaaagaat ccactctcca   300
cctggtcttg agattgagag gtggcatgca gatcttcgtg aagaccctca caggaaagac   360
catcactctt gaggtcgagc cttctgactc catcgaaaac gtcaaggcta aaattcaaga   420
caaggaaggt attcctccag atcagcagag attgatcttc gccggcaaac aactcgaaga   480
tggccgtacc ctctctgact acaatattca aaaagagtcc acccttcact ggtgttgag   540 attgcgtgga ggtatgcaaa tctttgtcaa acattgact ggaaagacca tcacccttga   600
agtcgaaccc tccgacacca tcgaaaatgt caaggcaag atccaggaca aggaaggcat   660
ccccccagat cagcagaggt tgattttcgc tggcaaacaa cttgaagacg gacgtaccct   720
ctcggactac aacatccaga aggagtcgac cctccatctt gtcctccgtc tgcgtggtgg   780
tatgcagatt tttgtcaaaa ctctgactgg caagacaatc cccttgaag tagagccctc   840 tgacaccatc gaaaatgtca aggcgaaaat ccaggacaaa gaaggcatcc cccagatca   900 gcagaggttg atcttcgccg gtaagcagct tgaagacggc cgtaccctct cggactacaa   960
catccagaag gagtccaccc ttcatcttgt cctccgtctg cgtggtggta tgcagatttt  1020
cgtgaagacc ttgactggca agaccatcac tcttgaggtc gagccctctg acaccatcga  1080
```

```
aaacgtcaag gccaagatcc aggacaagga aggtatcccc ccagatcagc agaggttgat    1140
cttcgctggc aagcagctcg aggatggtcg taccctctcg gactacaaca tccagaagga    1200
gtccacccct catcttgtcc tccgtctgcg tggtggtatg cagattttcg tgaagacctt    1260
gactggcaag accatcactc ttgaggtcga gccctctgac accattgaaa acgtcaaggc    1320
caagatccag gacaaggaag gtatccccc  agatcagcag aggttgatct tcgccggtaa    1380
gcagcttgaa gacggccgta ctctctctga ttacaacatc cagaaggagt cgaccctcca    1440
ccttgtcctc cgtctgcgtg tggtatgca  gattttcgtg aagaccttga ctggcaagac    1500
catcactctt gaggtcgagc cctctgacac cattgaaaac gtcaaggcca gatccagga    1560 taaggaaggc atcccccag  atcagcagag gttgatcttc gccggtaagc agcttgagga    1620
tggacgtacc ctgtcagact acaacatcca aaaggagtcc accctgcact ggtgttgag    1680 attgcgtggt ggtatgcaga tcttcgtcaa gaccttgact ggcaagacga tcactttgga    1740
agtcgagccc tctgacacca ttgagaatgt caaagccaaa atccaagata aggaaggcat    1800
ccccccagat cagcagaggt tgatcttcgc tggtaagcag cttgaagacg ccgcactct     1860 ttcggattac aacatccaga aggagtcgac cctccacctt gtccttcgtc tgcgtggtgg    1920
tatgcagatc ttcgtcaaga cgttgacagg caagaccatc acccttgaag tcgagccctc    1980
tgacaccatc gaaaacgtca aggctaagat ccaggacaag gaaggtatcc cccagatca    2040 gcaaagattg atcttcgccg gcaaacagct cgaagatggc cgtaccctct cagactacaa    2100
cattcaaaag gagtcaactc ttcatctcgt tctgaggctc cgtggcggtc gttattgatc    2160
acaattccaa acttaaaaat tgcgttccga ttttccttct ttatttggcg aaaaatacgt    2220
accctagtta attaaaatga cttgaaattt gatttttaa gaatgcttcg aatttttta     2280 tagatggttt gttacgtaga cgaatacaca acagtgaaag ccgaaaaaaa aaaaaaagg     2340 gcggcc                                                              2346
```

<210> SEQ ID NO 33
<211> LENGTH: 1151
<212> TYPE: DNA
<213> ORGANISM: Lygus hesperus

<400> SEQUENCE: 33

```
gctcttctcg ggaatcttcg aattcttcat agcaaatctc ttcgaattca tattcgggta     60
acgctcagcc ataaaagaat agtcctcgaa caaagcagta ataagttcaa ttcaggggaa    120
tttaatcttc gtaagcctag ccagggaatg aaccttcggg aaacttcaac aagaatttta    180
acataccagg gaaaccaggt cattcgaagt ttcttcagag aacgtagttc acttttcag     240 gagtaattca agaaataggg gatatcaagt ttggtctggt cagaatttga gatggggaga    300
aatattcagc agttgaaaag gaaacctcgg aaacctattg gacgtcgagg gacatcgttg    360
gtgggacgga aaaggaggta atggtggaag aaaaaaacca cgttttatgc aagtgacttt    420
ggatgattcc attgtggtgg gactcaacat caagaatact ccaaaagact gcttcatcgt    480
gaattcaagt cataatcttc gtgtcgatcg aattaatatt gacatcaaag atggggataa    540
gaagggaggg cacaacacag acgggtttgg cgtaagtgga tcgagaaatg tcacagtttc    600
aaactgccag gtccacaacc aagacgactg cttcgccacg acatctggaa gtgacacgat    660
attcgagaac agcaagtgca cggtgtgtca tggcatatct gtaggatcca tgggagctgg    720
aaaagtcgtt gaaagactga cagtgaggaa ctgtaggatt ttggcgaaca gcaatggcat    780
```
tcgaatcaag acccgacgag gagaaacggg tgcagtccgc gatattacgt ttgaaaatat    840
agagctgaaa gacataaggc agtatggtat tgtcattcaa ggcaattatt acaacagtgg    900
accgaaggga gaccccactc cttttcccat tcataacctg gttgtcaaca acgtgcacgg    960
tactgtgagc cgtaaaggaa ccaacatcct gatctgggtg gatcctggaa gcgtcagcaa   1020
ttggaaatgg aactcaaatg tgtccggagg tcagaaggaa cttggttgta aaggagttcc   1080
aagtggactg aacattcgtt gtggcgagaa ataaggtgtt tacgaccact tcatgtaaca   1140
cccaattaat g                                                       1151

<210> SEQ ID NO 34
<211> LENGTH: 823
<212> TYPE: DNA
<213> ORGANISM: Lygus hesperus
<220> FEATURE:
<221> NAME/KEY: misc_feature
<222> LOCATION: (729)..(729)
<223> OTHER INFORMATION: n is a, c, g, or t

<400> SEQUENCE: 34
ctcaaaactc aaaggttctc tcaggtatat ctttcagctt cctattcgga ttcaagacta     60
ttcattaata taagacttaa ggagtacaat aataataaat tcacgattaa ggacaaacga    120
tccttaatta atgatcctcc ttaattaata cctaacgcac tacccttttt atcacgtcag    180
gcaataaaaa gttctacacc ttatcaaaaa tcaacaaatt cctcaaaggt accttaggta    240
tgtatcattt acgtaacaat attacaatgc agaatttgca gccactacag aagggaatcg    300
caacaactat taagatttca caaggtagac taaacttact tagttacgcc gatttgatag    360
atgtagaatt atacttagtt attgccgaaa ataaattttt cttcgttaaa aaaccaaata    420
aaaggtaaca ataaacgtgg gtagagaact aaatcacgaa acgtatattt tagtgattgg    480
ataataaaga aaattttgaa gtttaaacgt tgcacattta tcacacatct cccaaaatta    540
tgggagcatc aaattcaatt catacagatt tggtcagtag gtacctaaat gaaattatcg    600
aggcatcatc ctacttgagt gggcatcgaa aacatacata atataataag atgctaacat    660
ctacagcaga aataaatacc tatattattt ttaaattatg gacaagaaag aaaggtactt    720
tcaactatng agagtagttt gataacatga gaaatattag taattaatca cgaatgggaa    780
tttaaaggat tgagatttgg ttacgtacaa tattgtagct ctt                     823

<210> SEQ ID NO 35
<211> LENGTH: 759
<212> TYPE: DNA
<213> ORGANISM: Lygus hesperus
<220> FEATURE:
<221> NAME/KEY: misc_feature
<222> LOCATION: (1)..(56)
<223> OTHER INFORMATION: n is a, c, g, or t
<220> FEATURE:
<221> NAME/KEY: misc_feature
<222> LOCATION: (127)..(149)
<223> OTHER INFORMATION: n is a, c, g, or t
<220> FEATURE:
<221> NAME/KEY: misc_feature
<222> LOCATION: (286)..(305)
<223> OTHER INFORMATION: n is a, c, g, or t
<220> FEATURE:
<221> NAME/KEY: misc_feature
<222> LOCATION: (457)..(478)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t

<400> SEQUENCE: 35

```
nnnnnnnnnn nnnnnnnnnn nnnnnnnnnn nnnnnnnnnn nnnnnnnnnn nnnnnntttc      60
aaaagtttaa catttttaaac gcaaccacgc ccccccaccc ccccaccgac cctcacatcc     120
ccccccnnnn nnnnnnnnnn nnnnnnnnng tgcgctctgg tggcttcgag ggtttcttct     180
tttttaaatt tactaagaac aatcaaactt cgattttcct attacccta cttcctttct      240
tctgatttgg gggttaaagt tttagaatga ttcggaaaaa tggaannnnn nnnnnnnnnn     300
nnnnntataa ttaaggacaa aatgattac agattagcg attaaaagaa atagagtaat       360
cgttttgata taattcttta tgttttttatc ttttttattc ttggggtttt tgagtgggat    420
tttggttttt tgtttaaaat tttgaaaaag gggaatnnnn nnnnnnnnnn nnnnnnntt      480
tggggaatat actgacaact tgtcacccga tgttaaagga ttttaacact tttcggtttt    540
cttttgttct ttgggttatt taatttttt cgaatttatt caaaaattta aaattaatca     600
aatttttcgng ggttattggt ttttaacca tttaaagttt ttatacccct tacgtttta     660
ccaatggcgt aacacctgta taaatggttg aaaatgttat attgtttttt tctgttcatc     720
ctttcaccat ttcatcattt cataaaacgg gaaagggat                            759
```

<210> SEQ ID NO 36
<211> LENGTH: 903
<212> TYPE: DNA
<213> ORGANISM: Lygus hesperus
<220> FEATURE:
<221> NAME/KEY: misc_feature
<222> LOCATION: (246)..(277)
<223> OTHER INFORMATION: n is a, c, g, or t
<220> FEATURE:
<221> NAME/KEY: misc_feature
<222> LOCATION: (435)..(450)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t

<400> SEQUENCE: 36

```
cgacggcggg ccggcccctt ctttcttcc ttctttccgg gttaaaacct tctccttttc      60
cacttcaaaa cacaacacaa taacactccc ctacaagtta aaatggccct catcaacaag    120
tctagccgta aaaatcaag tatggccact taacaaccac taatttcgac aactcggcat     180
ctaagttact tcgataaaag aaaatcaact acctactccg taacaatcag atcaaaccta    240
atcacnnnnn nnnnnnnnn nnnnnnnnnn nnnnnnncaa taataattta ctcgtgtaat     300
ttcaaacgtt ttcaagcttc gagtacgatc gaaccttcgt tctgcgaaat aacagttagg    360
gagttgctcg aataccaacg gggatttcgt ttgagaggtc ggaagcacac gcttgctctt    420
gagcagagtg accannnnnn nnnnnnnnnn aagcaagcca aacctcatac ctatacagtt    480
cctcggccct tcgccgaacg gaaggaaggt aaagggcgtg atggaggact tcttggtgtc    540
tgagaacctg tctgggtcga acctctcagg gtcggaaag tactgggggt cgtggtgcag     600
tgagtagacc gggatgagca cacgtattcc ctcctcgatt acgtatttgg tccccggaac    660
agcngtaagg tttttgtgcac acccgagtga gtgtgtggag agtcgggtac ttcctgatcg   720
tttcatttat gacctgatcg agataaggca tttcgtgtaa ggcttggtag ttgagaccgc   780
cgaatttact ggtgacttct tcaatttctc tacggacttt atcttgaatc acttgatggt    840
atgccaattc gtagagggcg taactctgta ctgaatgatg acgtctcgaa aacggcaatg    900
``` aaa                                                                903

<210> SEQ ID NO 37
<211> LENGTH: 890
<212> TYPE: DNA
<213> ORGANISM: Lygus hesperus
<220> FEATURE:
<221> NAME/KEY: misc_feature
<222> LOCATION: (3)..(29)
<223> OTHER INFORMATION: n is a, c, g, or t

<400> SEQUENCE: 37
cgnnnnnnnn nnnnnnnnnn nnnnnnnnnt tccagctttc gagttctttc cgtcacccca      60
ggtttccccg cacctccgtc cacggttccc ctccgggttc ggtttcctcc ggtgtcgcgg     120
acgaaggagt accggcctct tttcgtttcc gggacaggag gtttctcagt agtgtcagcc     180
gcaggcttcc gtcgaggttc gagcttcaga ggcctccgcc ggcttttcag caggcttttc     240
tgtttcgtcg gtggttgatt tggtggcttc accttcagac gtcgaaggtt ttgcgtcatc     300
gggtttggtt gtcagatctt ccactttggg tttgtcctct tgttgtcac tatcctcaac      360
ctgagtaggt tgtcggtgg gcgttggagc gggactgggg gcagcactgg tcgcaggggt      420
gccactactg ctagctgctt ccccaacact cccggcaggt ttcagctcgc caagttcctg     480
ccgcttttg aggatttcgg gcatagaata atatccgttg atatgctcga attcttggac      540
cttcttcctg atgagtgaca tgacgcctat cctcgtaagg acgtgttgtc gagacaaacc     600
ttcgcgagga actccgtcag caaaggtctc tgcgttgtca gcacccggct cgcaaaggtg     660
ccgcataaag agggaaacgt aggctttgaa atgttttttcg actttcctc gaaggtctcg     720
aaccaaccac tgcgaattga acgcatcttg gggaggcatt ccataccgca tgatcgcatt     780
gaggaaggcc tttctttgcc tggcgttgaa accaaggact tcgatgtttc caccaactct     840
agcgagaagt ggtggcagag gccggtcttt ctcttctcgt ctttcgggtc                890

<210> SEQ ID NO 38
<211> LENGTH: 763
<212> TYPE: DNA
<213> ORGANISM: Lygus hesperus
<220> FEATURE:
<221> NAME/KEY: misc_feature
<222> LOCATION: (22)..(52)
<223> OTHER INFORMATION: n is a, c, g, or t
<220> FEATURE:
<221> NAME/KEY: misc_feature
<222> LOCATION: (142)..(166)
<223> OTHER INFORMATION: n is a, c, g, or t

<400> SEQUENCE: 38
cctcccgaac ccgcctaaaa annnnnnnnn nnnnnnnnnn nnnnnnnnnn nnaacgcaaa      60
tatactacta gtacggactc ggtctggtaa acgctcgggg taccgggcag ctcacatgaa     120
attcgccagt aacgtataca annnnnnnnn nnnnnnnnnn nnnnnngaaa tcaggaacga     180
gtatgttaac gggattcttc ttattttcta tggtcggttt catggcagca tcgactcatg     240
cagaaacccg taggctgagt ggatgcatcc tgtccagtgc tcggcattct tgtggtaccc     300
ttcgggcgtg tttcatctcc ctggtgctcc attgcgttcc tgcttgtttt tatttatgat     360
gttggtcatt gctctcctaa tccagttttg tacgatggga gttttcatca cgtggatggt     420
tgtcaattgg tggcaattgc tgatatcgcc aatggagatg tttatcctcg gcgactgcat     480
agtgtactag ctttgatgat tctcctgctt atttcagggc actatgtaca tgttccacat     540
actgaattga tattcggaga gatccctgta cctgctgtta ctgatattat tcgacggaat     600

-continued

| | | | |
|---|---|---|---|
| tgccatatca | tgaaggcttt | ggaaatctga | cttctagcaa ccaattctct aaatgataag | 660 |
| ctactaacat | gtggattgtg | tgtagagtca | tctgtgtcga caacatgctt gatgtctgca | 720 |
| tcaagattgt | cgttatcatt | ctctctcact | ccactctcat cat | 763 |

<210> SEQ ID NO 39
<211> LENGTH: 1929
<212> TYPE: DNA
<213> ORGANISM: Lygus hesperus
<220> FEATURE:
<221> NAME/KEY: misc_feature
<222> LOCATION: (1920)..(1920)
<223> OTHER INFORMATION: n is a, c, g, or t

<400> SEQUENCE: 39

| | | | | |
|---|---|---|---|---|
| cagaggtcgt | atcgtggcaa | cgcaatatct | gctgaacgcg gaagctgtct aaatttttcg | 60 |
| taaggatcat | gcgggtaggg | cccttgagc | gcccatacga attctatcat gaatcgacag | 120 |
| tattaatggc | cggtgtgaaa | acttaacgct | tccggagctt cttgaactgg tagaggaacc | 180 |
| gaggtctgcc | ttgcgtgaca | acaggtcccc | gcatctcaag cttcttctta ttgaattatc | 240 |
| tccaaccaac | tctcaaaatg | cgtgagtgca | tcagcgtaca cgtcggccag gccggagttc | 300 |
| agatcggtaa | tgcctgctgg | gagctctact | gcttggaaca tggaattcag cctgatggac | 360 |
| acatgccgtc | agacaagacc | gttggaagcg | gtgatgactc cttcaacacg ttttctctg | 420 |
| agactggagc | tgggaagcac | gttccccgtg | ctgtctttgt tgatcttgag cccactgtcg | 480 |
| tcgacgaagt | taggactgga | acttacagac | agctcttcca ccccgagcaa ctcatcactg | 540 |
| gtaaggaaga | tgctgccaac | aactacgccc | gaggtcacta cacgatcggt aaggagatcg | 600 |
| tagacgtggt | gctggatagg | atccgcaagc | tgtctgatca gtgtaccgga ctccagggct | 660 |
| ttttgatttt | ccactccttc | ggcggcggca | ctggctctgg atttacctcc cttcttatgg | 720 |
| aacgcctttc | ggttgactac | ggcaagaaat | ccaagctcga attcgctgtc taccctgctc | 780 |
| ctcaggtctc | taccgctgtt | gttgaaccct | acaactccat cctcactacg cacactaccc | 840 |
| tcgagcactc | cgactgcgca | ttcatggtcg | acaatgaggc tatttatgac atctgccgcc | 900 |
| gtaacctgga | tattgagagg | ccgacctaca | ccaacctcaa caggctgatt ggtcagatcg | 960 |
| tttcctcaat | aacagcctct | cttcggttcg | atggagccct taatgtcgac ctcacggagt | 1020 |
| tccagacgaa | cttggtcccc | taccccagaa | tccacttccc cctcgtaacc tacgcccctg | 1080 |
| tcatctcggc | cgagaaagcc | taccacgaac | agctctctgt cggtgagatc accaacgctt | 1140 |
| gcttcgagcc | cgccaaccag | atggtgaaat | gcgacccgcg ccacggcaag tacatggcct | 1200 |
| gctgcatgtt | gtacaggggt | gatgttgtac | ccaaagacgt caacgccgcc atcgccacca | 1260 |
| tcaagaccaa | gaggtccatc | cagttcgtcg | actggtgtcc cactggtttc aaggtcggca | 1320 |
| tcaactacca | gccccccacc | gtcgttcctg | gaggtgactt ggccaaagtc cagcgagccg | 1380 |
| tctgcatgtt | gtccaacacg | accgccatcg | ccgaggcctg ggctcgcctc gatcacaagt | 1440 |
| tcgacttgat | gtacgccaag | cgagcctttg | tccactggta cgtcggcgag ggcatggagg | 1500 |
| aaggagaatt | ctctgaagcc | cgagaggatt | tggctgccct tgagaaagac tacgaagagg | 1560 |
| ttggaatgga | ctccgtcgaa | ggagatggcg | aaggagctga agaatactaa aatctacggt | 1620 |
| gtattatatt | ttatatgtat | tattattcaa | aacacgtttc tgtgctatat tacttgtacc | 1680 |
| tacgagaatt | tcatacaata | atgtttgtta | atttcgcttt ataaattatt acagtttttct | 1740 |
| acagatcaaa | aaaaaaaaaa | aagggcgccc | acgcgtccgc ccacgcgtcc ggacccacgc | 1800 |

| | |
|---|---|
| gtccggcaca actgagtact cattctcacg ccaaagtacg tgactaccat cgcgaaagct | 1860 |
| tttttttttac ttacctgaag gtttttttcc actatttatt ttaaagcaga tttaattaan | 1920 |
| tggcgtaat | 1929 |

<210> SEQ ID NO 40
<211> LENGTH: 3641
<212> TYPE: DNA
<213> ORGANISM: Lygus hesperus

<400> SEQUENCE: 40

| | |
|---|---|
| cccccccccc cccaccccca aacataaaaa aaaaaaaatt ttcttttttgg tgttgggggg | 60 |
| gtttgtgggg cccccccccc cccccccccc caaaaaaaaa accggagaga aaaaaaaaaa | 120 |
| aaaccttttt tttttgtgag aaaaaattgg ggggggtgtt tttttttttt tttttttttt | 180 |
| ccccccccctt aaaaaaaggc gcaaaaaaaa aaaaataatt acaccccccac aaactcccctt | 240 |
| ttttttttctt tttttttttt gttttggggg gggggggggg gggggggttt tttttaaaaa | 300 |
| aaaaaaaaac cccccccccaa aaatgggggg tggtgtttta ttttttacaaa aacacccctt | 360 |
| gggggggggg ggggggcccaa aaaaaacccc cggggggtttt tttttttaaaa aacccaccac | 420 |
| aaaaaaaaaa cccccccccc cccgggtaat ttttttttta aaaaaccccc cggaaaaaaa | 480 |
| aatctccccc ccccccaaaaa aaccggggtt ttccccccccc ccccccccaa aaaaattttt | 540 |
| ttttctcccca ggccctaaat tttctggggg ggggtttccc aaaaaccccc ccccccaaaa | 600 |
| aaagtgtttt tccaaaaaaa acccaaaaaa aattttttcc ccccccccgt ttttaaaaac | 660 |
| cccccccccc cccccttttt aaaaaaccccc ccctttgggg cccccttttt aaaaaaaaaa | 720 |
| gggggggccca aaaattggcc cccccccggggg aaattttaaa accccccccc ccctttttttt | 780 |
| tttttttttt tttttttttt tttttttttt tttttttttt tttttttttt tttttttttt | 840 |
| tttttttttt tttttttttt tttttttttt tttttttttt tttttttttt tttttttttt | 900 |
| tttttttttt tttttttttt tttttttttt tttttttttt tttttttttt tttttttttt | 960 |
| ttttcggtag taaatgttga gtgtaatctc aaacaacaat ataaatatat aaaatcaagt | 1020 |
| gcgtaatata taaacaatgt tctgccagaa aagagaaaaa attgggaagg cgaaggagcg | 1080 |
| agatcgggag tccaaaatat aagttgcaac aaaaacgaag aaagaataca cgtaaaaaaa | 1140 |
| ttactaaacc gggtttaaat taacaaagct caaggaatgt tcgatcgcta agctccagtt | 1200 |
| tatgttgcag gggtacaaat agagggaggg aactgccagc tggggatatc gtgtacaaaa | 1260 |
| caaatataga aaaacactg cgctctcgag gcgcagaatc accaggctgg ccacacgtct | 1320 |
| agtgtgaggg aatgaattcg actttttttt tttggttgag ggggggacatt tttgttttgt | 1380 |
| gtcgggaatg gggggggggg gggggggggat ttagttttcg tcgatctctt gttcttgctc | 1440 |
| ctcgtcgaat tcggcgtcct cgtcggcggt ggcctcctgg tactgctggt actcggacac | 1500 |
| caagtcgttc atgttggact cggcttcagt gaattccatc tcgtccatgc cctcgccggt | 1560 |
| gtaccaatgc aagaaagcct ttctcctgaa catggcagtg aattgctcgg agattctctt | 1620 |
| gaagagctcc tggatggcag tggagttgcc gatgaaggtg gcggacattt tgagtcctct | 1680 |
| gggggggaatg tcgcacacgg ctgtcttcac gttgttgggg atccattcca cgaagtacga | 1740 |
| ggagttcttg tttttggatgt tgagcatctg ctcgtccact tccttcatcg acattcgccc | 1800 |
| tctgaaaatg gcggcgacag tgaggtatc tccgtgtctg gggtcgcaag cggccatcat | 1860 |
| gttcttggcg tcgaacatct gctgggtcag ttcgggacg gacagagcgc ggtactgctg | 1920 |
| ggacccgcgt gacgtcagag gagcgaatcc tggcatgaag aagtggagtc gcgggaaggg | 1980 |

| | |
|---|---|
| aaccatgttg acggcgagtt tcctcagatc cgcgttgagc tgacctggga atcggaagca | 2040 |
| ggtggtgacg ccggacatgg tgaggctcac gaggtggttg aggtcgccgt aagtcggggt | 2100 |
| cgacagcttc aacgtcctga agcagatgtc gtagagggct tcgttatcta tgcagtaggt | 2160 |
| ctcgtccgtg ttttcgacga gttgatgtac cgagagtgtg gcgttgtagg gctccactac | 2220 |
| agtgtcggac accttgggag atggtacgac cgagtaagtg ttcatgattc tatcggggta | 2280 |
| ttcttctcgg atttttgaga tcaataacgt tcccatgcca gatccagttc cacctccaag | 2340 |
| agagtgagtc aattgaaatc cctgtaagca atcacagcct tcggcctctt tcctgacgac | 2400 |
| atccaaaacg gcatcaacga gttcagcgcc ctccgtgtag tgacctttgg cccagttgtt | 2460 |
| tcccgctcca gactgtccga aaacgaagtt gtccggtctg aagagctgac caaagggtcc | 2520 |
| tgagcggact gagtccatgg ttccgggttc caagtcaacg aggatggctc tcggtacata | 2580 |
| ttttccaccg gatgcttcat tgtaataaac gttgatccgt tcaagctgga ggtcggagtc | 2640 |
| gccgtggtag gaaccggtgg ggtcgatgcc gtgttcgtcg gaaatgattt cccagaactt | 2700 |
| ggctccgatc tggttgccgc actggccggc ctgaatgtgt acgatttccc tcatttcgtg | 2760 |
| cgactgcgaa gaaaaatgaa aaacgagag ctgaaaaatt cgactgaaac gaagcaacgg | 2820 |
| cttctgacaa ccactgccag acccagtaaa gtaaacaaag ctactgttgc tgctgcagta | 2880 |
| gttgccacca gaaacgatgc tgttgctgcc gtcagttctg ccaagcaaac cgtggctgct | 2940 |
| gaagcttccg ctgcatcttc taaagtcaac gccaaggtta cctctgccaa aaataacgta | 3000 |
| gcctctgctg tttcctctgc caaggacaag gtttccgctg atgtctctca agctaaagag | 3060 |
| aaggcttcag ccaccactgc caaaatcgaa gagaagaaga acgccgctaa agagaaggct | 3120 |
| tcagaaatcg ctgccaaaat cgaagagaag accagctctg ccgtcgcagc cgctaaagaa | 3180 |
| aatatcagca aagctaaagc caccgccgcc aacaagcttg agtccgctaa agagacagct | 3240 |
| caagagtata tcaaagaagc aaaagctaaa gctgaagctt tgaaggagaa aatcgctgcc | 3300 |
| aacgaaaacg tccaaaaagt ccaagagaaa gtggacgcta tgaagagcta cgtgagccag | 3360 |
| gccgtcaacc agaaactgga tgcgcaccct caaatcaaag cacagatcca gaaagctgac | 3420 |
| cagaaattgt ctgcacttac cgacaccatc aagagccaaa tgaatgaaaa ggtcccagcc | 3480 |
| ctgaaggaga agctcgaatc actcagtgcc agcttcaaac aatccttcga caagaacata | 3540 |
| gaaaaggcga aggagatgtt cgcctcctcg taattccatt tacaagggcc acacatgctc | 3600 |
| gaaaaatcga gtatccgatg tatataattc aataaaacta c | 3641 |

<210> SEQ ID NO 41
<211> LENGTH: 1760
<212> TYPE: DNA
<213> ORGANISM: Lygus hesperus

<400> SEQUENCE: 41

| | |
|---|---|
| ggccggaaag tggggaaaaa agccgttcgg gaaaatcccc tgaaacctgg ccagaagtgg | 60 |
| aacccagctg gggaatggcc tgctgatcat ggcgggtttg gatgtgatgt tagttgggtg | 120 |
| tggagggggtg aggaggaacc ccctagcctc gagagaatgg atctctcaga catttggagg | 180 |
| cgctgggcga ctgggggggat cctcgctaac gtcgctggca atcgcgacac gtccgacttc | 240 |
| atatcagaca gcagctcctc cagctgttca gtacctgtgg aggacagcat tggcgggctt | 300 |
| gttgccagcc aaactctcct tgctcaggtg ctgatgggac tcggccagac attcgacctc | 360 |
| cgcgaacctc gcgttgaggg acatggcagg atggttggga tcctgcgtca ggttcaggta | 420 |

```
agcagctctc ctcagttgct cttcgatgac caacgcctgc tccaaaagct tgaacctcct    480
ggcaaggaat tgttcttga tttcgaggaa gtttcctttg ccaacgtcca ttttgaatgg    540
ttcgttgatg atcgcgaaac ggatgtcgtt ctgaatgtct tgccagcggc cgtaaccgtg    600
cgtaacaata cctccgagca gccagtaatc atgcctcctg tgccagatct cgtactctcg    660
accgggtacc gcagccttct cttcattctg ccacagagtg tggagttctg taaagcctcc    720
gtcggcgatg ttgaacatga acttcctctt ggatttgtct tcttcgaagt caggaagctt    780
gactttctcc tcgtcctccg tcttctcgtc cttttcttct tgacgacgg attcttcttt    840
ttctcgctcg tcacccccctt ttttttttt tttcgtttca gctttaggtt cttccgtcac    900
ctcaggtttc tccgcatcta cgtccatagg ttcctctttg ggtttggttt cttccggtgt    960
tgtggacgaa ggagtatcgg cttctttcgt ttctgggaca ggtggtttct cagtagtgtc    1020
agctgcaggc tccgttgagg tttgagcttc agaggcctct gccggctttt cagcaggctt    1080
ttctgtttcg tcggtggttg atttggtggc ttcaccttca gacgtcgaag gttttgcgtc    1140
atcgggtttg gttgtcagat cttccacttt gggtttgtcc tctttgttgt cactatcctc    1200
aacctgagta ggtttgtcgg tgggcgttgg agcgggactg ggggcagcac tggtcgcagg    1260
ggtgccacta ctgctagctg cttccccaac actcccggca ggtttcagct cgccaagttc    1320
ctgccgcttt ttgaggattt cgggcataga ataatatccg ttgatatgct cgaattcttg    1380
gaccttcttc ctgatgagtg acatgacgcc tatcctcgta aggacgtgtt gtcgagacaa    1440
accttcgcga ggaactccgt cagcaaaggt ctctgcgttg tcagcacccg gctcgcaaag    1500
gtgccgcata aagagggaaa cgtaggcttt gaaatgtttt tcggactttc ctcgaaggtc    1560
tcgaaccaac cactgcgaat tgaacgcatc ttggggaggc attccatacc gcatgatcgc    1620
attgaggaag gcctttcttt gcctggcgtt gaaaccaagg acttcgatgt ttccaccaac    1680
tctagcgaga agtggtggca gaggccggtc tttctcttct cgtctttcgg gtcgcctctt    1740
cttcttcata gtaccatcgt                                                1760

<210> SEQ ID NO 42
<211> LENGTH: 1156
<212> TYPE: DNA
<213> ORGANISM: Lygus hesperus

<400> SEQUENCE: 42
ggctcttgtc tgtgaccctg gtcgtcttct gtaacttttt ctcttcgaat tttgagtttt     60
ttgacttttg tgacattcag taggtactaa aatcaccgaa aatggctctc agcgacgcag    120
atgtacaaaa acaaatcaaa cacatgatgg cttcattga gcaagaagcc aatgaaaaag    180
ccgaagaaat cgatgctaaa gctgaggaag agttcaacat tgaaaagggt cgacttgtac    240
agaaccagcg attgaagatc atggactact acgagaggaa agagaagcaa gtcgagctcc    300
agaagaaaat ccaatcttcc aacatgttga accaagcgag gctgaaggct ttgaaagtac    360
gtgaagatca cgtaagaaat gtcatggacg atgctcgtaa aaggcttgtc cagtccgccc    420
aaaatcctca acaatactct gaaatcttga taaaactcgt catgcaagct ctccttcagt    480
tgttggagaa ggaagtcacc ctcaaaatca gagaaaagga ccaagacctc atcaacaacc    540
ttgtgcccat gatccaggac aagtacaagg agatctccgg tctcgatatc aagctcaaaa    600
tcgacactga ctccttcctt cctccccgagt ccagcggagg catcgaactc tatgctctta    660
agaactgcat gaaggtgtcc aacactctcg agagccgtct cgacctgatc gctcaacagc    720
tggtccctca ggtccgaact gctctcttcg gcaggaaccc caaccgtaga ttcgatgatt    780
```

```
agatcctcat tttcaaccca tccactcgag aaattatatc tttacgtata aaattattag    840
actcaggaat ccccctccaa actcttgcat taaatttttt cggtctagta ccaaattttg    900
aacaacgttt tcgttatcct attagtgctc agcttgctcc cttccactaa cctaaaacta    960
agcctaggta ccattctaat tccacatctc tccccccccat atgttttctt aacgggggtt   1020
ggaaaattaa aggaaaaaaa taacattcca cttttccaaa aaaccgggcc ccccccccct   1080
taaaaacctc aaaaaaattc ctggtttttt tttaggggggc ccccaaaaa aaattttttt   1140 tgggaaagcc ttaaca                                                    1156
```

<210> SEQ ID NO 43
<211> LENGTH: 2928
<212> TYPE: DNA
<213> ORGANISM: Lygus hesperus

<400> SEQUENCE: 43

```
cccacgcgtc cgggttggtg gtttggttgg actggacgac attctgcgaa gttaactttg     60
tctacaaata acagattcaa ccatggcttt acccagaatc cgtgatgagg agaaagaatc    120
cagatttgga tatgtattcg ccgtttctgc cctgtcgtc actgcggaga gatgtcgggg     180
ggccgctatg tacgagctgg tgcgcgtcgg gtacttcgag ttggtcggcg aaatcattcg    240
tcttgaagga gacatggcca ccattcaggt ctacgaagaa catccggtg taacagttgg     300 agatcccgtg ttgagaactg ggaaaccact ttcggtggag ctcggtccgg gtattatgag    360
cagcattttt gacggtattc agcgaccttt gaaagacatt tgcgagctga ctcagagcat    420
ctacatcccc aagggagtca acgttccagc tctgtccagg tctattgcat gggacttcac    480
tccgtccaac aatatcaagg tgggagcaca catcactggt ggtgatttgt atgccgtcgt    540
tcacgaaaac acgcttgtca agcaaaaaat gatcatgccg gccagaggaa ggggtaccgt    600
gaaatacatc gctcccccctg gcaactacac tgttgatgac gtcgtaatgg aaactgaatt    660
cgacggagag aaaactgaaa tcaagatgtt gcaagtttgg cctgtccgac agccccgtcc    720
agttgccgaa aaactgcctg ctaactatcc actcttgact ggtcaacgag ttttggatgc    780
cctcttcccg tgtgtccaag gtggtaccac cgccattccc ggtgccttcg gctgtggaaa    840
aactgtcatc tcacaagctc tgtccaaata ctcaaactct gacgtcatca tttacgtcgg    900
atgcggtgaa cgtggtaacg aaatgtctga ggtattgaga gatttccccg aactcacagt    960
tgagattgac ggtgtaactg agtccatcat gaagcgtact gctctggtcg ccaacacatc   1020
caacatgcct gtagctgctc gagaagcttc catttatact ggtatcacat tgtccgaata   1080
cttccgtgac atgggttaca acgtgtcgat gatggctgac tccacctctc gatgggccga   1140
agccttgaga gaaatttcag gtcgtctcgc tgaaatgcct gctgacagtg gttaccctgc   1200
ctacttggga gcccgtttgg cttccttcta cgagcgagct ggtcgtgtca atgtcttgg    1260 aagtcccgac agagagggct cagtcagtat cgtcggtgcc gtgtcgcctc ctggtggtga   1320
cttttcggat cctgtcactt cagccaccct tggtatcgta caggtcttct ggggtctcga   1380
caagaaattg gcacaaagga aacacttccc ctccatcaac tggctcatct cttacagtaa   1440
gtacatgaga gctttggacg acttctatga caaacgtgta cctgaattcg tgccctgag    1500 gaccaaggtc aaggagatcc tccaggagga agaagatttg gctgaaattg tgcagctcgt   1560
cggtaaaggt tcgctggccg agtctgataa gatcacattg gaaatcgcta agatcttgaa   1620
agacgatttc ttgcaacaaa acagctactc gccctacgac agattctgtc cgttctacaa   1680
```

```
gacggtcggt atgttgaaga acatgatctc tttctatgat cttgcgaggc acacggtgga    1740
atcaacagca caaagcgaca acaagatcac ttggactgtc atcaaagaaa gcatgggcaa    1800
catcctctac cagctgtcct caatgaaatt caaggacccc gtcaaagacg agaagccaa     1860 gatcaaaggc gacttcgaac agctccacga agacatgcaa caagctttcc gcaacctcga    1920
agactaaaca gttttctcgt tcgctacctt attgttgaca atagtggcac tacagattaa    1980
cttcagtgca atttttaaca gcaaccgcaa atatcctcct cctccccccc ttgaaactca    2040
tactatcgtt acacaatttg tacatataaa aacacgtctg ttgtaattac acataattat    2100
tgtatatctt tcgagggtag tatttgggta gcagataatg aaacttagta actagcgagt    2160
agactacaat attaaaaata ttctgtcaac cccaatcaat tcacgagaaa aaagggaagc    2220
atttatgatt tgttttctc gcgagcacat tactttctac gagctgcatt ccaatccttt     2280
aatttcttag tcgtgtcatt tcaacgtgtt caatttattg attgacttcg ttgtatcact    2340
tcggtctagg tttccttgtc tcggttaatt gttaagcttt acaagtagag aaaaaaaagt    2400 acttttaat tcagtattaa attgtttttt tgtaatatag gtggcgtgtc taatagaaaa     2460
agacaatttg ctccgcttgg gcaaaactac aaggaacata actcttctgg atttgattct    2520
ttcgttgtgt gatatttttc gaagtctact tttccccatt ttcgagcgca aaagcttcgg    2580 tacttacccct ccaaattttg aaaattaata tctgaagtgt gaagatgaac gagttcaact   2640
ggaacaactc ttgggagttt ctaattcaca ggatgtttct gtacctataa cttttaatta    2700
ttttctgttc aggatgtttt taatcaaatt aagattaaat attgtattat attgttgaaa    2760 aaggttttt tttttttggc ttccaagtaa agccagtaat tgtttacatt tccttggaaa     2820 cttttgtgt agttagggct actgaacgct ctattatttc tgtgaagggg cagagtaaaa     2880
ataaaatatt ttgaaaagtt gttaaaaaaa aaaaaaaaa gggggggg                  2928
```

<210> SEQ ID NO 44
<211> LENGTH: 702
<212> TYPE: DNA
<213> ORGANISM: Artificial
<220> FEATURE:
<223> OTHER INFORMATION: synthetic

<400> SEQUENCE: 44

```
atggctttct tcaacagggt tatcaccctg accgtgccta gctctgacgt ggtgaactac      60
tctgaaatct accaagttgc ccctcagtac gtgaaccagg ccctgaccct agccaagtac    120
ttccagggtg ccattgacgg tagcaccctt agattcgact tcgagaaggc cctccagatc    180
gccaacgaca tcccacaggc cgctgtggtc aacaccctca accagaccgt gcagcaaggc    240
accgtgcaag tgagcgtgat gatcgacaag atcgtggaca tcatgaagaa cgtgctctcc    300
atcgtgatcg acaacaagaa attctgggac caagtgaccg ccgctatcac caacaccttc    360
accaacctca actcccagga gtccgaggct tggatcttct actacaagga ggacgcccac    420
aagacctcct actattacaa catcctcttc gccatccagg acgaggaaac aggcggtgtg    480
atggctacac tcccccatcgc tttcgacatc tccgtggaca tcgagaagga gaaagtcctc    540
ttcgtcacca tcaaggacac cgagaactac gctgtcactg tcaaggctat caacgtcgtt    600
caggctctcc agtccagccg cgactccaaa gtcgttgacg ctttcaagtc tcccaggcac    660
ctccctagga agaggcacaa gatttgcagc aacagctgat aa                       702
```

<210> SEQ ID NO 45
<211> LENGTH: 232

```
<212> TYPE: PRT
<213> ORGANISM: Artificial
<220> FEATURE:
<223> OTHER INFORMATION: synthetic

<400> SEQUENCE: 45

Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser
225                 230

<210> SEQ ID NO 46
<211> LENGTH: 660
<212> TYPE: DNA
<213> ORGANISM: Artificial
<220> FEATURE:
<223> OTHER INFORMATION: synthetic

<400> SEQUENCE: 46
atgagcaagg agatccgtct caacctctct cgggagtctg gcgcggacct ctacctgaag      60
atcctggcgt tcgtcaagcc cgagcatttc tttcaggcgt acctgctttg ccggagttc     120 gagtctatcg tcgatccgac tactagagag tcagatttcg ataagactct gactattgtc    180
aagtcggatt ctactctggt cactgtcggc actatgaaca ctaagctggt caactcgcaa    240
gagattctgg tctcggatct gattactcaa gttggtagtc agattgcgga tacgctgggc    300
attacggaca ttgatgcaaa cacacagcaa caactgacag agcttattgg gaatcttttc    360
gttaatctta atagtcaagt tcaagagtac atctacttct acgaagagaa ggagaagcaa    420
acgtcatatc gttacaacat tctctttgtt ttcgagaagg aatcattcat taccatactt    480
ccaatgggat tgatgttac ggtgaacaca aataaggaag cagttctaaa gttgacacca     540
```
aaggataaag ttacttatgg acacgtatca gtaaaggcac ttaatatcat tcaacttatc    600
acagaagata aattcaattt tctcgcaaca ctcaagaagg ctttgaagac cttgtgataa    660

<210> SEQ ID NO 47
<211> LENGTH: 218
<212> TYPE: PRT
<213> ORGANISM: Artificial
<220> FEATURE:
<223> OTHER INFORMATION: synthetic

<400> SEQUENCE: 47

Met Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
            20                  25                  30

Ala Tyr Leu Leu Cys Arg Glu Phe Glu Ser Ile Val Asp Pro Thr Thr
        35                  40                  45

Arg Glu Ser Asp Phe Asp Lys Thr Leu Thr Ile Val Lys Ser Asp Ser
    50                  55                  60

Thr Leu Val Thr Val Gly Thr Met Asn Thr Lys Leu Val Asn Ser Gln
65                  70                  75                  80

Glu Ile Leu Val Ser Asp Leu Ile Thr Gln Val Gly Ser Gln Ile Ala
                85                  90                  95

Asp Thr Leu Gly Ile Thr Asp Ile Asp Ala Asn Thr Gln Gln Gln Leu
            100                 105                 110

Thr Glu Leu Ile Gly Asn Leu Phe Val Asn Leu Asn Ser Gln Val Gln
        115                 120                 125

Glu Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175

Lys Leu Thr Pro Lys Asp Lys Val Thr Tyr Gly His Val Ser Val Lys
            180                 185                 190

Ala Leu Asn Ile Ile Gln Leu Ile Thr Glu Asp Lys Phe Asn Phe Leu
        195                 200                 205

Ala Thr Leu Lys Lys Ala Leu Lys Thr Leu
    210                 215

<210> SEQ ID NO 48
<211> LENGTH: 1413
<212> TYPE: DNA
<213> ORGANISM: Artificial
<220> FEATURE:
<223> OTHER INFORMATION: synthetic

<400> SEQUENCE: 48
atggctttct tcaacagggt tatcaccctg accgtgccta gctctgacgt ggtgaactac    60
tctgaaatct accaagttgc ccctcagtac gtgaaccagg ccctgaccct agccaagtac    120
ttccagggtg ccattgacgg tagcaccctt agattcgact tcgagaaggc cctccagatc    180
gccaacgaca tcccacaggc cgctgtggtc aacaccctca accagaccgt gcagcaaggc    240
accgtgcaag tgagcgtgat gatcgacaag atcgtggaca tcatgaagaa cgtgctctcc    300
atcgtgatcg acaacaagaa attctgggac caagtgaccg ccgctatcac caacaccttc    360

```
accaacctca actcccagga gtccgaggct tggatcttct actacaagga ggacgcccac    420
aagacctcct actattacaa catcctcttc gccatccagg acgaggaaac aggcggtgtg    480
atggctacac tccccatcgc tttcgacatc tccgtggaca tcgagaagga gaaagtcctc    540
ttcgtcacca tcaaggacac cgagaactac gctgtcactg tcaaggctat caacgtcgtt    600
caggctctcc agtccagccg cgactccaaa gtcgttgacg ctttcaagtc tcccaggcac    660
ctccctagga gaggcacaa gatttgcagc aacagcaagc ctgctttgct taaggaagct    720
cctagggcag aagaggagtt gcctccacgt aagatgagca aggagatccg tctcaacctc    780
tctcgggagt ctggcgcgga cctctacctg aagatcctgg cgttcgtcaa gcccgagcat    840
ttctttcagg cgtacctgct tgccgggag ttcgagtcta tcgtcgatcc gactactaga    900
gagtcagatt tcgataagac tctgactatt gtcaagtcgg attctactct ggtcactgtc    960
ggcactatga acactaagct ggtcaactcg aagagattc tggtctcgga tctgattact    1020
caagttggta gtcagattgc ggatacgctg gcattacgg acattgatgc aaacacacag    1080
caacaactga cagagcttat tgggaatctt ttcgttaatc ttaatagtca agttcaagag    1140
tacatctact tctacgaaga gaaggagaag caaacgtcat atcgttacaa cattctcttt    1200
gttttcgaga aggaatcatt cattaccata cttccaatgg gatttgatgt tacggtgaac    1260
acaaataagg aagcagttct aaagttgaca ccaaaggata agttactta tggacacgta    1320 tcagtaaagg cacttaatat cattcaactt atcacagaag ataaattcaa ttttctcgca    1380
acactcaaga aggctttgaa gaccttgtga taa                                 1413
```

<210> SEQ ID NO 49
<211> LENGTH: 469
<212> TYPE: PRT
<213> ORGANISM: Artificial
<220> FEATURE:
<223> OTHER INFORMATION: synthetic

<400> SEQUENCE: 49

Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser Lys Pro Ala Leu Leu Lys Glu Ala
225                 230                 235                 240

Pro Arg Ala Glu Glu Leu Pro Arg Lys Met Ser Lys Glu Ile
                245                 250                 255

Arg Leu Asn Leu Ser Arg Glu Ser Gly Ala Asp Leu Tyr Leu Lys Ile
            260                 265                 270

Leu Ala Phe Val Lys Pro Glu His Phe Phe Gln Ala Tyr Leu Leu Cys
        275                 280                 285

Arg Glu Phe Glu Ser Ile Val Asp Pro Thr Thr Arg Glu Ser Asp Phe
    290                 295                 300

Asp Lys Thr Leu Thr Ile Val Lys Ser Asp Ser Thr Leu Val Thr Val
305                 310                 315                 320

Gly Thr Met Asn Thr Lys Leu Val Asn Ser Gln Glu Ile Leu Val Ser
                325                 330                 335

Asp Leu Ile Thr Gln Val Gly Ser Gln Ile Ala Asp Thr Leu Gly Ile
            340                 345                 350

Thr Asp Ile Asp Ala Asn Thr Gln Gln Gln Leu Thr Glu Leu Ile Gly
        355                 360                 365

Asn Leu Phe Val Asn Leu Asn Ser Gln Val Gln Glu Tyr Ile Tyr Phe
    370                 375                 380

Tyr Glu Glu Lys Glu Lys Gln Thr Ser Tyr Arg Tyr Asn Ile Leu Phe
385                 390                 395                 400

Val Phe Glu Lys Glu Ser Phe Ile Thr Ile Leu Pro Met Gly Phe Asp
                405                 410                 415

Val Thr Val Asn Thr Asn Lys Glu Ala Val Leu Lys Leu Thr Pro Lys
            420                 425                 430

Asp Lys Val Thr Tyr Gly His Val Ser Val Lys Ala Leu Asn Ile Ile
        435                 440                 445

Gln Leu Ile Thr Glu Asp Lys Phe Asn Phe Leu Ala Thr Leu Lys Lys
    450                 455                 460

Ala Leu Lys Thr Leu
465

<210> SEQ ID NO 50
<211> LENGTH: 1413
<212> TYPE: DNA
<213> ORGANISM: Artificial
<220> FEATURE:
<223> OTHER INFORMATION: synthetic

<400> SEQUENCE: 50
atgagcaagg agatccgtct caacctctct cgggagtctg gcgcggacct ctacctgaag    60
atcctggcgt cgtcaagcc cgagcatttc tttcaggcgt acctgctttg ccgggagttc    120
gagtctatcg tcgatccgac tactagagag tcagatttcg ataagactct gactattgtc    180
aagtcggatt ctactctggt cactgtcggc actatgaaca ctaagctggt caactcgcaa    240
gagattctgg tctcggatct gattactcaa gttggtagtc agattgcgga tacgctgggc    300
attacggaca ttgatgcaaa cacacagcaa caactgacag agcttattgg gaatcttttc    360

```
gttaatctta atagtcaagt tcaagagtac atctacttct acgaagagaa ggagaagcaa    420
acgtcatatc gttacaacat tctctttgtt ttcgagaagg aatcattcat taccatactt    480
ccaatgggat tgatgttac ggtgaacaca aataaggaag cagttctaaa gttgacacca    540
aaggataaag ttacttatgg acacgtatca gtaaaggcac ttaatatcat tcaacttatc    600
acagaagata aattcaattt tctcgcaaca ctcaagaagg ctttgaagac cttgaagcct    660
gctttgctta aggaagctcc tagggcgaaa gaggagttgc ctccacgtaa gatggctttc    720
ttcaacaggg ttatcaccct gaccgtgcct agctctgacg tggtgaacta ctctgaaatc    780
taccaagttg cccctcagta cgtgaaccag gccctgaccc tagccaagta cttccagggt    840
gccattgacg gtagcaccct tagattcgac ttcgagaagg ccctccagat cgccaacgac    900
atcccacagg ccgctgtggt caacaccctc aaccagaccg tgcagcaagg caccgtgcaa    960
gtgagcgtga tgatcgacaa gatcgtggac atcatgaaga acgtgctctc catcgtgatc    1020
gacaacaaga aattctggga ccaagtgacc gccgctatca ccaacacctt caccaacctc    1080
aactcccagg agtccgaggc ttggatcttc tactacaagg aggacgccca caagacctcc    1140
tactattaca acatcctctt cgccatccag gacgaggaaa caggcggtgt gatggctaca    1200
ctccccatcg ctttcgacat ctccgtggac atcgagaagg agaaagtcct cttcgtcacc    1260
atcaaggaca ccgagaacta cgctgtcact gtcaaggcta tcaacgtcgt tcaggctctc    1320
cagtccagcc gcgactccaa agtcgttgac gctttcaagt ctcccaggca cctccctagg    1380
aagaggcaca agatttgcag caacagctga taa                                 1413

<210> SEQ ID NO 51
<211> LENGTH: 469
<212> TYPE: PRT
<213> ORGANISM: Artificial
<220> FEATURE:
<223> OTHER INFORMATION: synthetic

<400> SEQUENCE: 51

Met Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
            20                  25                  30

Ala Tyr Leu Leu Cys Arg Glu Phe Glu Ser Ile Val Asp Pro Thr Thr
        35                  40                  45

Arg Glu Ser Asp Phe Asp Lys Thr Leu Thr Ile Val Lys Ser Asp Ser
    50                  55                  60

Thr Leu Val Thr Val Gly Thr Met Asn Thr Lys Leu Val Asn Ser Gln
65                  70                  75                  80

Glu Ile Leu Val Ser Asp Leu Ile Thr Gln Val Gly Ser Gln Ile Ala
                85                  90                  95

Asp Thr Leu Gly Ile Thr Asp Ile Asp Ala Asn Thr Gln Gln Gln Leu
            100                 105                 110

Thr Glu Leu Ile Gly Asn Leu Phe Val Asn Leu Asn Ser Gln Val Gln
        115                 120                 125

Glu Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175
```

Lys Leu Thr Pro Lys Asp Lys Val Thr Tyr Gly His Val Ser Val Lys
            180                 185                 190

Ala Leu Asn Ile Ile Gln Leu Ile Thr Glu Asp Lys Phe Asn Phe Leu
        195                 200                 205

Ala Thr Leu Lys Lys Ala Leu Lys Thr Leu Lys Pro Ala Leu Leu Lys
    210                 215                 220

Glu Ala Pro Arg Ala Glu Glu Leu Pro Pro Arg Lys Met Ala Phe
225                 230                 235                 240

Phe Asn Arg Val Ile Thr Leu Thr Val Pro Ser Ser Asp Val Val Asn
                245                 250                 255

Tyr Ser Glu Ile Tyr Gln Val Ala Pro Gln Tyr Val Asn Gln Ala Leu
            260                 265                 270

Thr Leu Ala Lys Tyr Phe Gln Gly Ala Ile Asp Gly Ser Thr Leu Arg
        275                 280                 285

Phe Asp Phe Glu Lys Ala Leu Gln Ile Ala Asn Asp Ile Pro Gln Ala
    290                 295                 300

Ala Val Val Asn Thr Leu Asn Gln Thr Val Gln Gln Gly Thr Val Gln
305                 310                 315                 320

Val Ser Val Met Ile Asp Lys Ile Val Asp Ile Met Lys Asn Val Leu
                325                 330                 335

Ser Ile Val Ile Asp Asn Lys Lys Phe Trp Asp Gln Val Thr Ala Ala
            340                 345                 350

Ile Thr Asn Thr Phe Thr Asn Leu Asn Ser Gln Glu Ser Glu Ala Trp
        355                 360                 365

Ile Phe Tyr Tyr Lys Glu Asp Ala His Lys Thr Ser Tyr Tyr Asn
    370                 375                 380

Ile Leu Phe Ala Ile Gln Asp Glu Thr Gly Gly Val Met Ala Thr
385                 390                 395                 400

Leu Pro Ile Ala Phe Asp Ile Ser Val Asp Ile Glu Lys Glu Lys Val
                405                 410                 415

Leu Phe Val Thr Ile Lys Asp Thr Glu Asn Tyr Ala Val Thr Val Lys
            420                 425                 430

Ala Ile Asn Val Val Gln Ala Leu Gln Ser Ser Arg Asp Ser Lys Val
        435                 440                 445

Val Asp Ala Phe Lys Ser Pro Arg His Leu Pro Arg Lys Arg His Lys
    450                 455                 460

Ile Cys Ser Asn Ser
465

<210> SEQ ID NO 52
<211> LENGTH: 57
<212> TYPE: DNA
<213> ORGANISM: Artificial
<220> FEATURE:
<223> OTHER INFORMATION: synthetic

<400> SEQUENCE: 52
aagcctgctt tgcttaagga agctcctagg gcagaagagg agttgcctcc acgtaag        57

<210> SEQ ID NO 53
<211> LENGTH: 19
<212> TYPE: PRT
<213> ORGANISM: Artificial
<220> FEATURE:
<223> OTHER INFORMATION: synthetic

<400> SEQUENCE: 53

```
Lys Pro Ala Leu Leu Lys Glu Ala Pro Arg Ala Glu Glu Glu Leu Pro
1               5                   10                  15

Pro Arg Lys

<210> SEQ ID NO 54
<211> LENGTH: 930
<212> TYPE: DNA
<213> ORGANISM: Artificial
<220> FEATURE:
<223> OTHER INFORMATION: synthetic

<400> SEQUENCE: 54
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttaccttcac ccaccctcgc ttgatcccct acgatcttac tatcccgcag     180
aaccttgaga ccatcttcac cacaacgcag gtgctcacca ataacactga cctccagcaa     240
tcccagaccg tgagctttgc gaagaagacc actaccacga cctcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactacctt ccagcaagca agcactgaca ttgagtggaa cattagccaa     480
ccggtgctgg ttcctccctc taaacaagtt gtcgcgaccc ttgtgatcat gggaggcaac     540
tttaccatcc ctatggactt gatgaccacg attgatagta cagagcacta ctcccactac     600
tccggttacc ctatcctcac ctggatctcg tccccagata actcttactc cggtcccttt     660
atgtcatggt actttgcaaa ctggcctaac cttccgagtg gattcggccc actgaatagt     720
gataacacgg tcacatacac tggctctgtc gtgtcccaag tttcggccgg tgtctacgct     780
accgtccggt tcgatcagta tgacattcac aatctccgta ctatcgagaa gacttggtat     840
gctcgccatg cgacgctgca taatggcaag aagatttcta tcaacaatgt cacggaaatg     900
gctccaacat cccctatcaa gacaaattga                                      930

<210> SEQ ID NO 55
<211> LENGTH: 340
<212> TYPE: PRT
<213> ORGANISM: Bacillus thuringiensis

<400> SEQUENCE: 55

Met Ala Ile Met Asn Asp Ile Ala Gln Asp Ala Ala Arg Ala Trp Asp
1               5                   10                  15

Ile Ile Ala Gly Pro Phe Ile Arg Pro Gly Thr Thr Pro Thr Asn Arg
            20                  25                  30

Gln Leu Phe Asn Tyr Gln Ile Gly Asn Ile Glu Val Glu Pro Gly Asn
        35                  40                  45

Leu Asn Phe Ser Val Val Pro Glu Leu Asp Phe Ser Val Ser Gln Asp
    50                  55                  60

Leu Phe Asn Asn Thr Ser Val Gln Gln Ser Gln Thr Ala Ser Phe Asn
65                  70                  75                  80

Glu Ser Arg Thr Glu Thr Thr Ser Thr Ala Val Thr His Gly Val Lys
                85                  90                  95

Ser Gly Val Thr Val Ser Ala Ser Ala Lys Phe Asn Ala Lys Ile Leu
            100                 105                 110

Val Lys Ser Ile Glu Gln Thr Ile Thr Thr Thr Val Ser Thr Glu Tyr
        115                 120                 125
```

```
Asn Phe Ser Ser Thr Thr Thr Arg Thr Asn Thr Val Thr Arg Gly Trp
    130                 135                 140

Ser Ile Ala Gln Pro Val Leu Val Pro Pro His Ser Arg Val Thr Ala
145                 150                 155                 160

Thr Leu Gln Ile Tyr Lys Gly Asp Phe Thr Val Pro Val Leu Leu Ser
                165                 170                 175

Leu Arg Val Tyr Gly Gln Thr Gly Thr Leu Ala Gly Asn Pro Ser Phe
                180                 185                 190

Pro Ser Leu Tyr Ala Ala Thr Tyr Glu Asn Thr Leu Leu Gly Arg Ile
            195                 200                 205

Arg Glu His Ile Ala Pro Pro Ala Leu Phe Arg Ala Ser Asn Ala Tyr
    210                 215                 220

Ile Ser Asn Gly Val Gln Ala Ile Trp Arg Gly Thr Ala Thr Thr Arg
225                 230                 235                 240

Val Ser Gln Gly Leu Tyr Ser Val Val Arg Ile Asp Glu Arg Pro Leu
                245                 250                 255

Ala Gly Tyr Ser Gly Glu Thr Arg Thr Tyr Tyr Leu Pro Val Thr Leu
                260                 265                 270

Ser Asn Ser Ser Gln Ile Leu Thr Pro Gly Ser Leu Gly Ser Glu Ile
            275                 280                 285

Pro Ile Ile Asn Pro Val Pro Asn Ala Ser Cys Lys Lys Glu Asn Ser
    290                 295                 300

Pro Ile Ile Ile His His Asp Arg Glu Lys His Arg Glu Arg Asp Tyr
305                 310                 315                 320

Asp Lys Glu His Ile Cys His Asp Gln Ala Glu Lys Tyr Glu Arg Asp
                325                 330                 335

Tyr Asp Lys Glu
            340
```